(12) United States Patent
Weitekamp et al.

(10) Patent No.: US 12,036,078 B2
(45) Date of Patent: *Jul. 16, 2024

(54) ORAL PRODUCTS AND METHODS FOR PRODUCING THE SAME

(71) Applicant: POLYSPECTRA, INC., Berkeley, CA (US)

(72) Inventors: Raymond A. Weitekamp, Berkeley, CA (US); Aditya Balasubramanian, Berkeley, CA (US)

(73) Assignee: POLYSPECTRA, INC., Berkeley, CA (US)

( * ) Notice: Subject to any disclaimer, the term of this patent is extended or adjusted under 35 U.S.C. 154(b) by 345 days.

This patent is subject to a terminal disclaimer.

(21) Appl. No.: 17/399,368

(22) Filed: Aug. 11, 2021

(65) Prior Publication Data
US 2022/0110728 A1    Apr. 14, 2022

Related U.S. Application Data

(63) Continuation of application No. PCT/US2021/045094, filed on Aug. 6, 2021.
(Continued)

(51) Int. Cl.
*A61C 13/00*    (2006.01)
*A61K 6/62*     (2020.01)
(Continued)

(52) U.S. Cl.
CPC ...... *A61C 13/0013* (2013.01); *A61C 13/0019* (2013.01); *A61K 6/62* (2020.01);
(Continued)

(58) Field of Classification Search
CPC . A61C 13/0019; A61C 13/0013; B33Y 10/00; B33Y 40/20; B29C 64/124;
(Continued)

(56) References Cited

U.S. PATENT DOCUMENTS

| 7,538,172 B2 | 5/2009 | Moszner et al. |
| 9,045,579 B2 | 6/2015 | Xia et al. |

(Continued)

FOREIGN PATENT DOCUMENTS

| EP | 3063592 A1 | 9/2016 |
| EP | 2903996 B1 | 8/2018 |

(Continued)

OTHER PUBLICATIONS

Horie et al., Poly(thienylvinylene) prepared by ring-opening metathesis polymerization: Performance as a donor in bulk heterojunction organic photovoltaic devices, Polymer51 (2010) 1541-1547.
(Continued)

*Primary Examiner* — Jerzi H Moreno Hernandez
(74) *Attorney, Agent, or Firm* — WILSON SONSINI GOODRICH & ROSATI

(57) ABSTRACT

The present disclosure relates to a method for generating a dental product or an orthodontic product. The method may comprise (a) providing a mixture comprising (i) a latent ruthenium (Ru) complex; (ii) an initiator; (iii) a sensitizer that sensitizes said initiator; and (iv) at least one polymer precursor; and (b) exposing the mixture to electromagnetic radiation to activate the initiator, wherein upon activation, the initiator reacts with the latent Ru complex to generate an activated Ru complex, which activated Ru complex reacts with the at least one polymer precursor to generate at least a portion of a final product of the dental product or the orthodontic product, wherein the at least the portion of the final product of the dental product or the orthodontic product comprises a polymer generated from the at least one polymer precursor.

13 Claims, 18 Drawing Sheets

Related U.S. Application Data

(60) Provisional application No. 63/089,748, filed on Oct. 9, 2020.

(51) Int. Cl.
*A61K 6/887* (2020.01)
*B29C 64/124* (2017.01)
*B29C 64/35* (2017.01)
*B33Y 10/00* (2015.01)
*B33Y 40/20* (2020.01)
*B29L 31/00* (2006.01)

(52) U.S. Cl.
CPC ............ *A61K 6/887* (2020.01); *B29C 64/124* (2017.08); *B29C 64/35* (2017.08); *B33Y 10/00* (2014.12); *B33Y 40/20* (2020.01); *B29L 2031/753* (2013.01); *C08G 2261/418* (2013.01)

(58) Field of Classification Search
CPC ..... B29C 64/129; B29C 64/135; B29C 64/35; A61K 6/62; A61K 6/887; C08G 2261/418
See application file for complete search history.

(56) References Cited

U.S. PATENT DOCUMENTS

| | | |
|---|---|---|
| 9,147,844 B2 | 9/2015 | Grubbs et al. |
| 9,207,532 B2 | 12/2015 | Weitekamp et al. |
| 9,234,985 B2 | 1/2016 | Grubbs et al. |
| 9,382,387 B2 | 7/2016 | Xia et al. |
| 9,453,943 B2 | 9/2016 | Miyake et al. |
| 9,573,125 B2 | 2/2017 | Weitekamp et al. |
| 10,799,613 B2 | 10/2020 | Weitekamp et al. |
| 11,725,077 B2* | 8/2023 | Balasubramanian .. B33Y 70/00 526/171 |
| 2002/0167100 A1 | 11/2002 | Moszner et al. |
| 2006/0004158 A1 | 1/2006 | Moszner et al. |
| 2010/0029801 A1* | 2/2010 | Moszner ................. B33Y 70/10 522/167 |
| 2015/0118188 A1 | 4/2015 | Weitekamp et al. |
| 2018/0059566 A1 | 3/2018 | Tanabe et al. |
| 2018/0067393 A1 | 3/2018 | Weitekamp |
| 2019/0039321 A1* | 2/2019 | Matzner ................ B29C 64/393 |
| 2019/0048130 A1* | 2/2019 | Rhodes ..................... C08K 3/22 |
| 2019/0090984 A1* | 3/2019 | Martz ................... B29C 64/124 |
| 2019/0090995 A1* | 3/2019 | Ruppert ............. A61C 13/0019 |
| 2019/0210354 A1* | 7/2019 | Vidavsky ............... B33Y 30/00 |
| 2019/0336254 A1* | 11/2019 | Hasan .................... B29C 64/40 |
| 2020/0002466 A1* | 1/2020 | Burtovyy ............... B33Y 70/00 |
| 2020/0122388 A1* | 4/2020 | Van Esbroeck .... A61C 13/0019 |
| 2020/0183276 A1 | 6/2020 | Weitekamp |
| 2020/0215811 A1* | 7/2020 | Friedrich ............... B33Y 30/00 |
| 2021/0163676 A1 | 6/2021 | Balasubramanian et al. |
| 2021/0323233 A1* | 10/2021 | Dias ........................ B29C 64/35 |

FOREIGN PATENT DOCUMENTS

| | | |
|---|---|---|
| EP | 3507007 A1 | 7/2019 |
| JP | 2001059018 A | 3/2001 |
| WO | WO-2014055720 A1 | 4/2014 |
| WO | WO-2015065649 A1 | 5/2015 |
| WO | WO-2017068590 A1 | 4/2017 |
| WO | WO-2018045132 A1 | 3/2018 |
| WO | WO-2019032937 A1 | 2/2019 |
| WO | WO-2019147878 A1 | 8/2019 |
| WO | WO-2019212353 A1 | 11/2019 |
| WO | WO-2020006345 A1 | 1/2020 |
| WO | WO-2021072206 A1 | 4/2021 |
| WO | WO-2022076076 A1 | 4/2022 |

OTHER PUBLICATIONS

Joo, et al. Photoinitiated ring-opening metathesis polymerization. Journal of Polymer Science Part A: Polymer Chemistry 57.17 (2019): 1791-1795.

Keitz, et al. A tandem approach to photoactivated olefin metathesis: combining a photoacid generator with an acid activated catalyst. Journal of the American Chemical Society 131.6 (2009): 2038-2039.

Lee, et al. Effect of PAG and matrix structure on PAG acid generation behavior under UV and high-energy radiation exposure. In Advances in Resist Materials and Processing Technology XXV, vol. 6923, p. 69232F. International Society for Optics and Photonics, 2008.

Moon, M. 'Replicator' 3D printer uses light to create structures in one piece. Feb. 1, 2019. Available at https://www.engadget.com/2019-02-01-replicator-3d-printer-uses-light-to-create-structures-in-one-p.html. Accessed on Oct. 8, 2020.

Ogawa, et al. Metal-free ring-opening metathesis polymerization. Journal of the American Chemical Society 137.4 (2015): 1400-1403.

PCT/US20/55003 International Search Report and Written Opinion dated Jan. 27, 2021.

Theunissen, et al. Visible-light-controlled ruthenium-catalyzed olefin metathesis. Journal of the American Chemical Society 141.17 (2019): 6791-6796.

Weitekamp, et al. Photolithographic olefin metathesis polymerization. Journal of the American Chemical Society 135.45 (2013): 16817-16820.

U.S. Appl. No. 17/070,557 Office Action dated Dec. 13, 2022.

PCT/US2021/45094 International Search Report and Written Opinion dated Nov. 29, 2021.

* cited by examiner

*Penetration Depth: 307 μm*
*Critical Exposure: 172 mJ/cm²*
*r² : 0.940*

Top View

Side View

ORAL PRODUCTS AND METHODS FOR PRODUCING THE SAME

CROSS-REFERENCE

This application is a continuation of International Patent Application PCT/US21/45094, filed Aug. 6, 2021, which claims the benefit of U.S. Provisional Application No. 63/089,748, filed Oct. 9, 2020, each of which is entirely incorporated herein by reference for all purposes.

STATEMENT AS TO FEDERALLY SPONSORED RESEARCH

This invention was made with government support under SBIR #1758545 awarded by The National Science Foundation. The government has certain rights in the invention.

BACKGROUND

Printing three-dimensional (3D) objects (e.g., oral products (e.g., dental products or orthodontic products)) that are, for example, strong, durable, and functional remains difficult. For example, 3D printing techniques may be limited to, for example, slow print speeds, high material costs, high processing costs, high printing temperatures, and complex post-processing techniques.

SUMMARY

Provided herein are olefin-metathesis based photopolymerization reactions, which can include, for example, ring opening metathesis polymerization (ROMP) (e.g., a photoinitiated ROMP (P-ROMP) or PhotoLithographic Olefin Metathesis Polymerization (PLOMP)), to produce cyclic olefin photopolymer resins. The application of photo-initiated olefin metathesis to the additive manufacturing of three dimensional (3D) objects (e.g., oral products (e.g., dental products or orthodontic products)) enables significant improvements, for example, to the methods and objects, over other printing techniques. Objects (e.g., oral products (e.g., dental products or orthodontic products)) provided herein may have better characteristics or features, such as, for example, improved working temperature, toughness, impact strength, chemical resistance, biocompatibility, photomodulus coefficient, higher green strength, longer pot life, and longer shelf life than objects printed with other printing techniques. Methods provided herein are more efficient and cost-effective than other (e.g., metathesis-based) printing techniques, such as for, example, providing higher printing accuracy, lower critical exposure, increased print speed, and printability at lower temperatures.

The methods and compositions provided herein can produce a cured cyclic olefin photopolymer with improved features or characteristics over radical- and acid-based photopolymers. The methods and compositions provided herein may produce a (e.g., cured cyclic olefin) photopolymer with improved characteristics than other techniques, such as, for example: improved ductility, improved clarity (e.g., low chroma, low staining), improved biocompatibility, improved chemical resistance, improved processability (e.g., glass transition temperature ($T_g$), high dimensional accuracy, low photopolymer shrinkage, low viscosity, low leaching), improved tear strength, improved impact strength, improved strain at yield, improved strain at break, improved water absorption (e.g., low water absorption), improved organoleptics, improved heat-deflection temperature, or any combination thereof.

The methods and compositions provided herein can provide a photochemical approach that produces a product or body that achieves material properties similar to or better than, for example, a thermoformed (e.g., dental) material, including, for example, an acrylic or polyolefin thermoplastic, a cyclic olefin polymer, or a cyclic olefin copolymer (e.g., Zendura, Biocryl, Essix, or Invisacryl).

The compositions and methods provided herein can provide an approach for using direct additive manufacturing to produce oral products (e.g., dental products or orthodontic products). Such products or bodies may be ductile. Such compositions and methods may not comprise tooling, molding (e.g., thermoforming), computer numerical (CNC) milling, or CNC cutting. Such features may reduce the production cost and time for producing an oral product (e.g., a dental product or an orthodontic product) provided herein. Such features may increase or enhance customization, personalization, or design freedom for producing a product or a body described herein.

The compositions and methods provided herein can provide an approach for incorporating additives into the product or body (e.g., the photopolymer material). Such additives (e.g., pigments, dyes, optical brighteners, fluorescent whitening agents, bluing agents, decorative particles, nanoparticles, dielectric mirrors, photonic crystals, non-linear optical media, white pigments, impact modifiers, or plasticizers) provided herein may modify the features, characteristics, or properties (e.g., optical properties, mechanical properties, chemical properties, or biological properties) provided herein of the, for example, oral product.

The compositions and methods provided herein can provide an approach for manufacturing oral products (e.g., dental products or orthodontic products) with sub-components, component geometries, or a combination thereof. Such sub-components, component geometries, or a combination thereof may be difficult, impractical, or impossible to achieve with other techniques (e.g., molding techniques).

The compositions and methods provided herein can provide an approach to manufacture (e.g., using additive manufacturing) production-grade products or bodies (e.g., dental products, orthodontic products, or components thereof) in a physically-distributed manner, such as, for example, at a point-of-sale, a medical office (e.g., a dental office), a retail store, a hospital, or a clinic.

In certain aspects, the present disclosure provides a method of generating an oral product (e.g., a dental product or an orthodontic product), comprising (a) providing a mixture comprising (i) a latent ruthenium (Ru) complex, (ii) an initiator and (iii) the at least one polymer precursor; and (b) exposing the mixture to electromagnetic radiation to activate the initiator, wherein upon activation, the initiator reacts with the latent Ru complex to generate an activated Ru complex, which activated Ru complex reacts with the at least one polymer precursor to polymerize at least portion of the at least one polymer precursor, thereby forming at least a portion of the oral product (e.g., a dental product or an orthodontic product).

In some embodiments, the latent Ru complex is a Grubbs-type catalyst. In some embodiments, the Grubbs-type catalyst comprises at least one N-heterocyclic carbene (NHC) ligand. In some embodiments, wherein the method further comprises at least two NHC ligands. In some embodiments, the Ru complex comprises a 16-electron species.

In some embodiments, the initiator is a photoacid (PAH), a photoacid generator (PAG), or a combination thereof. In some embodiments, the PAH, PAG, or the combination thereof is selected from the group consisting of sulfonium salts, iodonium salts, triazines, triflates, and oxime sulfonates. In some embodiments, the initiator is bis(4-tert-butylphenyl)iodonium hexafluorophosphate.

In some embodiments, the at least one polymer precursor comprises at least one olefin. In some embodiments, the at least one olefin is a cyclic olefin. In some embodiments, the cyclic olefin is dicyclopentadiene, tricyclopentadiene, or norbornene.

In some embodiments, the electromagnetic radiation has a wavelength from 10 nanometers (nm) to 10 m. In some embodiments, the wavelength is 150 nm to 2000 nm.

In some embodiments, the method further comprises an additive. In some embodiments, the additive is selected from the group consisting of fillers, fibers, polymers, surfactants, inorganic particles, cells, viruses, biomaterials, rubbers, impact modifiers, graphite and graphene, colorants, dyes, pigments, carbon fiber, glass fiber, textiles, lignin, cellulose, wood, and metal particles.

In some embodiments, the method further comprises a stabilizer. In some embodiments, the stabilizer is selected from the group consisting of organic or inorganic Lewis or Bronsted bases, antioxidants, antiozonants, surfactants, oxygen scavengers, ligands, quenchers, and light-absorbers.

In some embodiments, the activated Ru complex comprises at least one N-heterocyclic carbene (NHC) ligand. In some embodiments, the activated Ru complex comprises one NHC ligand. In some embodiments, the active complex comprises a 14-electron species.

In other aspects, the present disclosure provides a method for printing a three-dimensional (3D) oral product (e.g., dental product or orthodontic product), comprising (a) providing a resin comprising (i) a latent ruthenium (Ru) complex, (ii) an initiator and (iii) at least one polymer precursor; and (b) exposing the resin to electromagnetic radiation to activate the initiator, wherein upon activation, the initiator reacts with the latent Ru complex to generate an activated Ru complex, which activated Ru complex reacts with the polymer precursor to generate at least portion of the 3D oral product (e.g., dental product or orthodontic product).

In certain aspects, provided herein is a method for generating a dental product or an orthodontic product, comprising (a) providing a mixture comprising (i) a latent ruthenium (Ru) complex; (ii) an initiator; (iii) a sensitizer that sensitizes said initiator; and (iv) at least one polymer precursor; and (b) exposing said mixture to electromagnetic radiation to activate said initiator, wherein upon activation, said initiator reacts with said latent Ru complex to generate an activated Ru complex, which activated Ru complex reacts with said at least one polymer precursor to generate at least a portion of said dental product or said orthodontic product.

In some embodiments, dental product or said orthodontic product is generated using additive manufacturing.

In some embodiments, sensitizer is configured to transfer or disperse the energy of electromagnetic radiation (e.g., electromagnetic radiation having a wavelength from 300 nanometers (nm) to 3,000 nm (e.g., 350 nm to 465 nm)).

In some embodiments, mixture is activated at a wavelength from 200-800 nanometers (nm) (e.g., 350 nm to 465 nm) at a temperature from 0 degrees Celsius (° C.) to 100° C. (e.g., 20° C. to 50° C.) for 1 nanosecond (ns) to 1 week (e.g., 1 millisecond (ms) to 1 hour).

In some embodiments, the method further comprises cleaning said dental product or said orthodontic product. In some embodiments, the dental product or said orthodontic product is cleaned using a solvent, agitation, sonication, stirring, air drying, air knives, automated washing, or any combination thereof.

In some embodiments, a surface of said dental product or said orthodontic product is smoothed, brightened, coated, sealed, sterilized, or a combination thereof. In some embodiments, the method further comprises post-curing said dental product or said orthodontic product. In some embodiments, the dental product or said orthodontic product is post-cured using ultraviolet radiation, visible (light) radiation, convection heating, conduction heating, radiation heating, or any combination thereof.

In certain aspects, provided herein is a method for generating a dental product or an orthodontic product, comprising (a) providing a mixture comprising (i) a latent ruthenium (Ru) complex; (ii) an initiator; and (iii) at least one polymer precursor, wherein said latent Ru complex is present at a concentration from 0.1 parts per million (ppm) by weight to 1% by weight and said initiator is present at a concentration from 0.1 parts per million (ppm) by weight to 10% by weight; and (b) exposing said mixture to electromagnetic radiation to activate said initiator, wherein upon activation, said initiator reacts with said latent Ru complex to generate an activated Ru complex, which activated Ru complex reacts with said at least one polymer precursor to generate at least a portion of said dental product or said orthodontic product.

In certain aspects, provided herein is a method for generating a dental product or an orthodontic product, comprising (a) providing mixture comprising (i) a latent ruthenium (Ru) complex; (ii) an initiator; and (iii) at least one polymer precursor, wherein said latent Ru complex and said initiator are present at a ratio of said Ru complex to said initiator at a ratio by moles from 0.01:1.0 to 10:1.0; and exposing said mixture to electromagnetic radiation to activate said initiator, wherein upon activation, said initiator reacts with said latent Ru complex to generate an activated Ru complex, which activated Ru complex reacts with said at least one polymer precursor to generate at least a portion of said dental product or said orthodontic product.

In certain aspects, provided herein is a method for generating a dental product or an orthodontic product, comprising (a) providing mixture comprising (i) a latent ruthenium (Ru) complex; (ii) an initiator that is an iodonium salt or a sulfonium salt; and (iii) at least one polymer precursor; and (b) exposing said mixture to electromagnetic radiation to activate said initiator, wherein upon activation, said initiator reacts with said latent Ru complex to generate an activated Ru complex, which activated Ru complex reacts with said at least one polymer precursor to generate at least a portion of said dental product or said orthodontic product.

In certain aspects, proved herein is a method for producing a dental product or an orthodontic product, comprising combining (i) a latent catalyst, (ii) an initiator, and (iii) at least one polymer precursor, wherein said dental product or said orthodontic product has at least one characteristic selected from the group consisting of: impact strength, tear strength, chroma, cytotoxicity, smell, taste, manufacturing speed, dimensional accuracy, geometric freedom of design, hardness, weight, ability to move and rotate teeth, toughness, ability to protect teeth, ability to see teeth, apparent dental aesthetics including tooth whiteness, resistance to staining, durability, weatherability, and colorability.

In certain aspects, provided herein is a method for printing a dental product or an orthodontic product, comprising (a) providing a resin comprising (i) a latent ruthenium (Ru)

complex, (ii) an initiator, and (iii) at least one polymer precursor; and (b) exposing said resin to electromagnetic radiation to activate said initiator, wherein upon activation, said initiator reacts with said latent Ru complex to generate an activated Ru complex, which activated Ru complex reacts with said polymer precursor to print at least portion of said dental product or said orthodontic product.

In some embodiments, the method further comprises printing said dental product or said orthodontic product adjacent to a support. In some embodiments, the dental product or said orthodontic product is removed from said support using robot-assistance, sonication, vibration, chemical swelling, chemical etching, laser ablation, laser cutting, blade cutting, or any combination thereof.

In certain aspects, provided herein is a dental product or an orthodontic product, comprising a body comprising a cyclic olefin polymer. In some embodiments, the dental product or said orthodontic product is selected from the group consisting of an orthodontic aligner, a mouth guard, a surgical guide, a night guard, a splint, a denture, a prosthodontic, a dental prosthetic, an extra-oral appliance, a crown, a grill, dental jewelry, a brace, a surgical stent, a bruxism device (e.g., a bruxism guard), a sleep apnea device, a provisional or temporary restoration product (e.g., a temporary crown or a temporary bridge).

In some embodiments, the dental product or the orthodontic product further comprises an additive. In some embodiments, the additive is selected from the group consisting of a pigment (e.g., a white pigment), a dye (e.g., a fluorophore), an optical brightener, a fluorescent whitening agent, a bluing agent, a decorative particle, a nanoparticle, a dielectric mirror, a photonic crystal, a non-linear optical media, a white pigments, an impact modifier, and a plasticizer. In some embodiments, the additive modifies at least one property or characteristic of said dental product or said orthodontic product.

In some embodiments, the dental product or said orthodontic product comprises at least one sub-component, a component geometry, or any combination thereof. In some embodiments, the at least one sub-component or said component geometry is selected from the group consisting of a void, a lattice structure, a triple periodic minimal surface, a personalized geometry, a stylized geometry, an aesthetic geometry, a digitally-defined surface texture, a ring, a tori, a tube, a fluidic channel, a grip, an anchor, a connector, a hook, a ratchet, a valve, and a clip. In some embodiments, the component geometry includes at least one topology. In some embodiments, the at least one topology is configured to move one or more tooth (e.g., move, rotate, align, or any combination thereof) of an individual wearing said dental product or said orthodontic product.

In some embodiments, the dental product or the orthodontic product has an elongation at break ductility from 2-500%.

In some embodiments, the dental product or the orthodontic product has a tear strength from 1 kiloNewton per meter (kN/m) to 1000 kN/m.

In some embodiments, the dental product or the orthodontic product has an impact strength from 1 Joules per meter (J/m) to 10,000 J/m (e.g., 1 J/m to 1,000 J/m).

In some embodiments, the dental product or the orthodontic product has a strain at yield from 0.1% to 10,000%.

In some embodiments, the dental product or the orthodontic product has a strain at break from 1 percent (%) to 10,000%.

In some embodiments, the dental product or the orthodontic product has a water absorption (e.g., at 24 hours) from about 0.1 parts per billion (ppb) to 50 weight percent (wt %).

In some embodiments, the dental product or the orthodontic product has a glass transition temperature ($T_g$) from −50° C. to 250° C. (e.g., 100° C. to 200° C.).

In some embodiments, the dental product or the orthodontic product has a heat-deflection temperature (HDT) from 0 degrees Celsius (° C.) to 300° C. (e.g., 50° C. to 200° C.).

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

DETAILED DESCRIPTION

Figure 1:
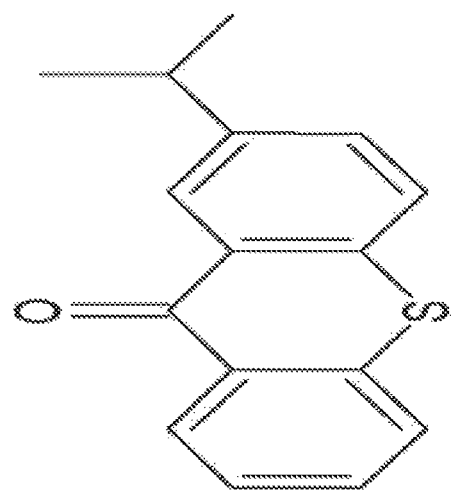
FIG. 1 depicts, from left to right respectively, examples for a latent ruthenium (Ru) complex, an initiator, and a polymer precursor.
Figure 1:
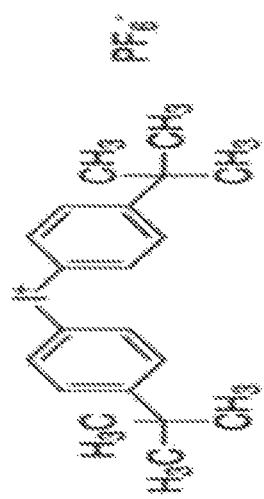
Figure 1:
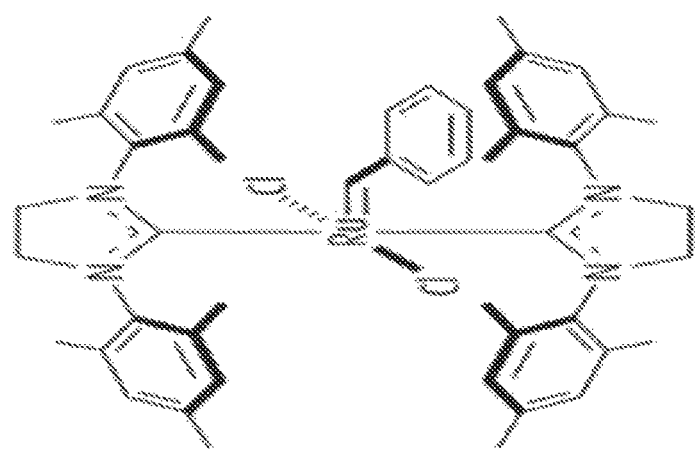

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Provided herein are compositions and methods for producing oral products (e.g., dental products or orthodontic products).

Described herein are compositions of and methods for processing photopolymers based on olefin metathesis. The compositions may comprise a latent ruthenium complex as well as a photoacid generator (PAG) or photoacid (PAH). Certain compositions may further comprise a sensitizer (e.g., to modify the wavelength of activity of the photoacid generator), stabilizers (e.g., to improve the dark stability of the photopolymer), as well as additives (e.g., to modify the performance of the liquid photopolymer and final cured part properties).

The mechanism of action for the compositions described herein may be the photogeneration of an acidic species, which subsequently removes an acid-sensitive ligand from the latent ruthenium complex. The ruthenium complex may undergo olefin metathesis after the dissociation of the ligand. Polymerization may occur via ring-opening metathesis polymerization (ROMP). This polymerization mechanism may be relevant to the photopolymerization of cyclic olefins. This proposed mechanism is presented for clarity; it is not intended to limit the scope of the invention described here.

Certain Terminology

As used herein, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and sub-combinations of ranges and specific embodiments therein are intended to be included. Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the present specification and attached claims are approximations that can vary depending upon the desired properties sought to be obtained by the present application. Generally the term "about," as used herein when referring to a measurable value such as an amount of weight, time, dose, etc. is meant to encompass in one example variations of ±15% or ±10%, in another example ±5%, in another example ±3%, in another example ±2%, in another example ±1%, and in yet another example ±0.1% from the specified amount, as such variations are appropriate to perform the disclosed method. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

The term "latent," as used herein, generally refers to a molecule, or a derivative thereof, that has an active state, but is in a less active or inactive state. For example, a latent catalyst, a latent complex, or a latent Ru complex may be a molecule in a less active than its active form. A latent catalyst, a latent complex, or a latent Ru complex may be in an inactive state. A latent catalyst may be a pre-catalyst.

The term "active" or "activated," as used herein, generally refers to a molecule, or a derivative thereof, that is in an active state. For example, an active catalyst, an active complex, or an active Ru complex may react or configured to react with another molecule, such as, for example, a polymer precursor.

The term "initiator," as used herein, generally refers to a molecule, or a derivative thereof, that interacts with the latent Ru complex, thereby producing the activated Ru complex. The initiator may be, for example, activated by light. The initiator may be a photoacid (PAH), a photoacid generator (PAG), or a combination thereof. The initiator may be, for example, a sulfonium salt, an iodonium salt, a triazine, a triflate, a dicarboximide, a thioxanthone, or an oxime. The initiator may be a sulfonium salt, an iodonium salt, a triazine, a triflate, or an oxime sulfonate. The initiator may be bis(4-tert-butylphenyl)iodonium hexafluorophosphate.

The term "sensitizer," as used herein, generally refers to a molecule, or a derivative thereof, that transfers, disperses or converts the energy of electromagnetic radiation. The sensitizer may transfer, disperse, or convert the energy of electromagnetic radiation towards the initiator. The sensitizer may transfer or disperse the energy of electromagnetic radiation in a way that activates the initiator, for example, in the presence of the electromagnetic radiation. The sensitizer may be configured to disperse, transfer, or convert the energy of electromagnetic radiation such that the initiator is activated at a particular wavelength range, such as, for example, from about 350 nanometers (nm) to about 465 nm.

The term "polymer," as used herein, generally refers to a molecule comprising at least two repeating units. The repeating units may comprise monomers, oligomers, polymers, or any combination thereof. The polymer may be a cyclic polymer, graft polymer, network polymer or branched polymer.

The term "polymerize," "polymerizing," or "polymerization," as used herein, generally refers to the process of reacting at least two polymer sub-units (e.g., monomers) to form a polymer chain or three-dimensional network.

The term "polymer precursor," as used herein, generally refers to a monomer, oligomer, or polymer that can polymerize into a larger polymer than the polymer precursor itself. The polymer precursor may comprise at least one olefin. In some embodiments, a polymer precursor is one or more molecular compound or oligomer, or combination thereof, each comprising at least one olefinic (alkene) or one acetylenic (alkyne) bond per molecule or oligomeric unit. The polymer precursor may comprise cyclic or alicyclic cis- or trans-olefins or cyclic or alicyclic acetylenes, or a structure having both types of bonds (including alicyclic or cyclic enynes).

"Alkyl" generally refers to a straight or branched hydrocarbon chain radical consisting solely of carbon and hydrogen atoms, such as having from one to fifteen carbon atoms (e.g., $C_1$-$C_{15}$ alkyl). Unless otherwise stated, alkyl is saturated or unsaturated (e.g., an alkenyl, which comprises at least one carbon-carbon double bond). Disclosures provided herein of an "alkyl" are intended to include independent recitations of a saturated "alkyl," unless otherwise stated. Alkyl groups described herein are generally monovalent, but may also be divalent (which may also be described herein as "alkylene" or "alkylenyl" groups). In certain embodiments, an alkyl comprises one to eighteen carbon atoms (e.g., $C_1$-$C_{18}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. In general, alkyl groups are each independently substituted or unsubstituted. Each recitation of "alkyl" provided herein, unless otherwise stated, includes a specific and explicit recitation of an unsaturated "alkyl" group. Similarly, unless stated otherwise specifically in the specification, an alkyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —$C(O)R^a$, —$C(O)OR^a$, —$C(O)N(R^a)_2$, —$N(R^a)C(O)OR^a$, —OC(O)—$N(R^a)_2$, —$N(R^a)C(O)R^a$, —$N(R^a)S(O)_tR^a$ (where t is 1 or 2), —$S(O)_tOR^a$ (where t is 1 or 2), —$S(O)_tR^a$ (where t is 1 or 2) and —$S(O)_tN(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is optionally substituted as described for "alkyl" groups.

"Alkylene" or "alkylene chain" generally refers to a straight or branched divalent alkyl group linking the rest of the molecule to a radical group, such as having from one to twelve carbon atoms, for example, methylene, ethylene, propylene, i-propylene, n-butylene, and the like. Unless stated otherwise specifically in the specification, an alkylene chain is optionally substituted as described for alkyl groups herein.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t R^a$ (where t is 1 or 2), —$R^b$—S(O)$_t R^a$ (where t is 1 or 2), —$R^b$—S(O)$_t OR^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Aralkyl" or "aryl-alkyl" refers to a radical of the formula —$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Carbocyclyl" or "cycloalkyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl or cycloalkyl is saturated (i.e., containing single C—C bonds only) or unsaturated (i.e., containing one or more double bonds or triple bonds). Examples of saturated cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t R^a$ (where t is 1 or 2), —$R^b$—S(O)$_t R^a$ (where t is 1 or 2), —$R^b$—S(O)$_t OR^a$ (where t is 1 or 2) and —$R^b$—S(O)N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Carbocyclylalkyl" refers to a radical of the formula —$R^c$-carbocyclyl where $R^c$ is an alkylene chain as defined above. The alkylene chain and the carbocyclyl radical is optionally substituted as defined above.

"Halo" or "halogen" refers to fluoro, bromo, chloro, or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. In some embodiments, the alkyl part of the fluoroalkyl radical is optionally substituted as defined above for an alkyl group.

The term "heteroalkyl" refers to an alkyl group as defined above in which one or more skeletal carbon atoms of the alkyl are substituted with a heteroatom (with the appropriate number of substituents or valencies—for example, —$CH_2$— may be replaced with —NH— or —O—). For example, each substituted carbon atom is independently substituted with a heteroatom, such as wherein the carbon is substituted with a nitrogen, oxygen, selenium, or other suitable heteroatom. In some instances, each substituted carbon atom is independently substituted for an oxygen, nitrogen (e.g. —NH—, —N(alkyl)-, or —N(aryl)- or having another substituent contemplated herein), or sulfur (e.g. —S—, —S(=O)—, or —S(=O)$_2$—). In some embodiments, a heteroalkyl is attached to the rest of the molecule at a carbon atom of the heteroalkyl. In some embodiments, a heteroalkyl is attached to the rest of the molecule at a heteroatom of the heteroalkyl. In some embodiments, a heteroalkyl is a $C_1$-$C_{18}$ heteroalkyl. In some embodiments, a heteroalkyl is a $C_1$-$C_{12}$ heteroalkyl. In some embodiments, a heteroalkyl is a $C_1$-$C_6$ heteroalkyl. In some embodiments, a heteroalkyl is a $C_1$-$C_4$ heteroalkyl. Representative heteroalkyl groups include, but are not limited to —$OCH_2OMe$, or —$CH_2CH_2OMe$. In some embodiments, heteroalkyl includes alkoxy, alkoxyalkyl, alkylamino, alkylaminoalkyl, aminoalkyl, heterocycloalkyl, heterocycloalkyl, and heterocycloalkylalkyl, as defined herein. Unless stated otherwise specifically in the specification, a heteroalkyl group is optionally substituted as defined above for an alkyl group.

"Heteroalkylene" refers to a divalent heteroalkyl group defined above which links one part of the molecule to another part of the molecule. Unless stated specifically otherwise, a heteroalkylene is optionally substituted, as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which optionally includes fused or bridged ring systems. The heteroatoms in the heterocyclyl radical are optionally oxidized. One or more nitrogen atoms, if present, are optionally quaternized. The heterocyclyl radical is partially or fully saturated. The heterocyclyl is attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxothiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$OC(O)$—$R^a$, —$R^b$—$OC(O)$—$OR^a$, —$R^b$—$OC(O)$—$N(R^a)_2$, —$R^b$—$N(R^a)_2$, —$R^b$—$C(O)R^a$, —$R^b$—$C(O)OR^a$, —$R^b$—$C(O)N(R^a)_2$, —$R^b$—$O$—$R^c$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tR^a$ (where t is 1 or 2), —$R^b$—$S(O)_tOR^a$ (where t is 1 or 2) and —$R^b$—$S(O)_tN(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Heterocyclylalkyl" refers to a radical of the formula —$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$OC(O)$—$R^a$, —$R^b$—$OC(O)$—$OR^a$, —$R^b$—$OC(O)$—$N(R^a)_2$, —$R^b$—$N(R^a)_2$, —$R^b$—$C(O)$ $R^a$, —$R^b$—C(O)O$R^a$, —$R^b$—C(O)N($R^a$)$_2$, —$R^b$—O—$R^c$—C(O)N($R^a$)$_2$, —$R^b$—N($R^a$)C(O)O$R^a$, —$R^b$—N($R^a$)C(O)$R^a$, —$R^b$—N($R^a$)S(O)$_t R^a$ (where t is 1 or 2), —$R^b$—S(O)$_t R^a$ (where t is 1 or 2), —$R^b$—S(O)$_t$O$R^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

The compounds disclosed herein, in some embodiments, contain one or more asymmetric centers and thus give rise to enantiomers, diastereomers, and other stereoisomeric forms that are defined, in terms of absolute stereochemistry, as (R)- or (S)—. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

In general, optionally substituted groups are each independently substituted or unsubstituted. Each recitation of an optionally substituted group provided herein, unless otherwise stated, includes an independent and explicit recitation of both an unsubstituted group and a substituted group (e.g., substituted in certain embodiments, and unsubstituted in certain other embodiments). Unless otherwise stated, substituted groups may be substituted by one or more of the following substituents: halo, cyano, nitro, oxo, thioxo, imino, oximo, trimethylsilanyl, —O$R^a$, —S$R^a$, —OC(O)—$R^a$, —N($R^a$)$_2$, —C(O)$R^a$, —C(O)O$R^a$, —C(O)N($R^a$)$_2$, —N($R^a$)C(O)O$R^a$, —OC(O)—N($R^a$)$_2$, —N($R^a$)C(O)$R^a$, —N($R^a$)S(O)$_t R^a$ (where t is 1 or 2), —S(O)$_t$O$R^a$ (where t is 1 or 2), —S(O)$_t R^a$ (where t is 1 or 2) and —S(O)$_t$N($R^a$)$_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

Processes:

In certain aspects, provided herein is a method for producing an oral product (e.g., a dental product or an orthodontic product), comprising (a) providing a mixture comprising (i) a latent ruthenium (Ru) complex, (ii) an initiator and (iii) the at least one polymer precursor; and (b) exposing the mixture to electromagnetic radiation to activate the initiator, wherein upon activation, the initiator reacts with the latent Ru complex to generate an activated Ru complex, which activated Ru complex reacts with the at least one polymer precursor to polymerize at least portion of the at least one polymer precursor, thereby producing the oral product (e.g., the dental product or the orthodontic product).

Provided in certain aspects herein is a method for controlling the reactivity of a mixture to generate oral product (e.g., a dental product or an orthodontic product), comprising (a) providing a mixture comprising (i) a latent ruthenium (Ru) complex; (ii) an initiator; (iii) a sensitizer configured to control the reactivity of said initiator; and (iv) at least one polymer precursor; and (b) exposing the mixture to electromagnetic radiation to activate the initiator, wherein upon activation, the initiator reacts with the latent Ru complex to generate an activated Ru complex, which activated Ru complex reacts with the at least one polymer precursor to generate at least a portion of the dental product or the orthodontic product.

In some aspects, provided herein is a method for generating oral product (e.g., a dental product or an orthodontic product), comprising (a) providing a mixture comprising (i) a latent ruthenium (Ru) complex; (ii) an initiator; (iii) a sensitizer that sensitizes the initiator; and (iv) at least one polymer precursor; and (b) exposing the mixture to electromagnetic radiation to activate the initiator, wherein upon activation, the initiator reacts with the latent Ru complex to generate an activated Ru complex, which activated Ru complex reacts with the at least one polymer precursor to generate at least a portion of the dental product or the orthodontic product.

In certain aspects, provided herein is a method for generating oral product (e.g., a dental product or an orthodontic product), comprising (a) providing a mixture comprising (i) a latent ruthenium (Ru) complex; (ii) an initiator; and (iii) at least one polymer precursor, wherein said latent Ru complex is present at a concentration from 0.1 parts per million (ppm) by weight to 1% by weight and said initiator is present at a concentration from 0.1 parts per million (ppm) by weight to 10% by weight; and (b) exposing the mixture to electromagnetic radiation to activate the initiator, wherein upon activation, the initiator reacts with the latent Ru complex to generate an activated Ru complex, which activated Ru complex reacts with the at least one polymer precursor to generate at least a portion of the dental product or the orthodontic product.

In other aspects, provided herein is a method for generating oral product (e.g., a dental product or an orthodontic product), comprising (a) providing mixture comprising (i) a latent ruthenium (Ru) complex; (ii) an initiator; and (iii) at least one polymer precursor, wherein the latent Ru complex and the initiator are present at a ratio of the Ru complex to the initiator at a ratio by moles from 0.01:1.0 to 10:1.0; and (b) exposing the mixture to electromagnetic radiation to activate the initiator, wherein upon activation, the initiator reacts with the latent Ru complex to generate an activated Ru complex, which activated Ru complex reacts with the at least one polymer precursor to generate at least a portion of the dental product or the orthodontic product.

In certain aspects, provided herein is a method for generating oral product (e.g., a dental product or an orthodontic product), comprising (a) providing mixture comprising (i) a latent ruthenium (Ru) complex; (ii) an initiator that is an iodonium salt or a sulfonium salt; and (iii) at least one polymer precursor; and exposing the mixture to electromagnetic radiation to activate the initiator, wherein upon activation, the initiator reacts with the latent Ru complex to generate an activated Ru complex, which activated Ru complex reacts with the at least one polymer precursor to generate at least a portion of the dental product or the orthodontic product.

In other aspects, provided herein is a method for producing oral product (e.g., a dental product or an orthodontic product), comprising combining (i) a latent catalyst, (ii) an initiator, and (iii) at least one polymer precursor, wherein the dental product or the orthodontic product has at least one characteristic selected from the group consisting of: impact strength, tear strength, chroma, cytotoxicity, smell, taste, manufacturing speed, dimensional accuracy, geometric freedom of design, hardness, weight, ability to move and rotate teeth, toughness, ability to protect teeth, ability to see teeth, apparent dental aesthetics including tooth whiteness, resistance to staining, durability, weatherability, and colorability.

In other aspects, provided herein is a method for producing oral product (e.g., a dental product or an orthodontic product), comprising combining (i) a latent catalyst, (ii) an initiator, and (iii) at least one polymer precursor, wherein the dental product or the orthodontic product has at least one characteristic selected from the group consisting of: improved impact strength, chemical resistance, toughness, shear strength, tear strength, temperature stability, lightweight, biocompatibility, optical performance, dielectric permeability, flexural strength, creep, weathering, durability, glass transition temperature, surface energy, surface adhesion, UV stability, fatigue resistance, flammability, stiffness (tensile, flexural, and compressive modulus), strength (tensile, flexural, and compressive), yield stress and strain, density, abrasion resistance, gas permeability, aesthetics (smell, taste, smoothness), and puncture resistance.

The latent Ru complex may have many structures. The latent Ru complex may be a Grubbs-type catalyst. The Grubbs-type catalyst may be, for example, a first-generation, second-generation, Hoveyda-Grubbs, or third-generation catalyst. The Grubbs-type catalyst may comprise at least one N-heterocyclic carbene (NHC) ligand. The Grubbs-type catalyst may comprise at least two NHC ligands. The Grubbs-type catalyst may comprise two NHC ligands. The latent Ru complex may comprise a 16-electron species.

The latent Ru complex may include, for example:

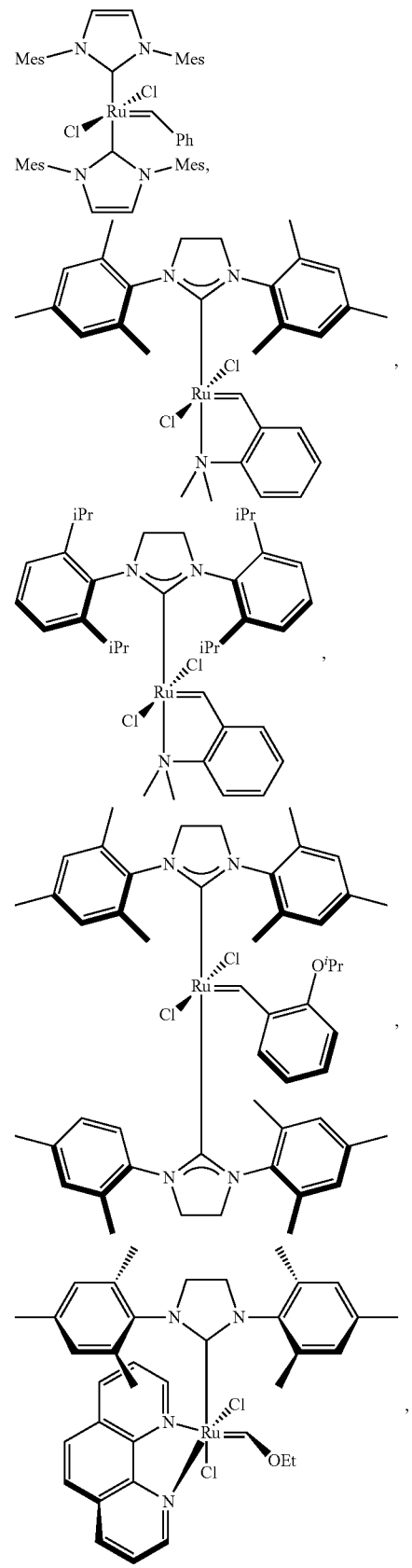

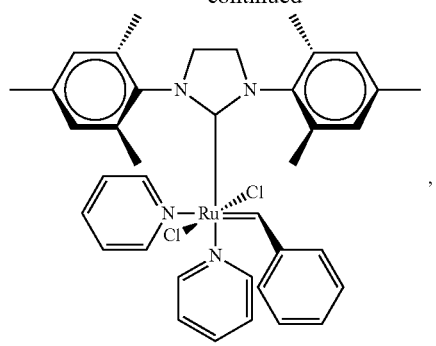
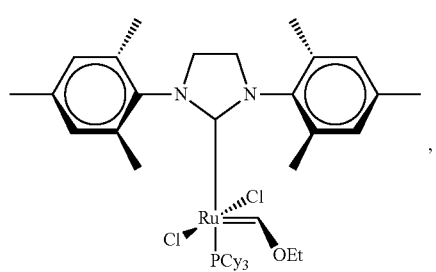
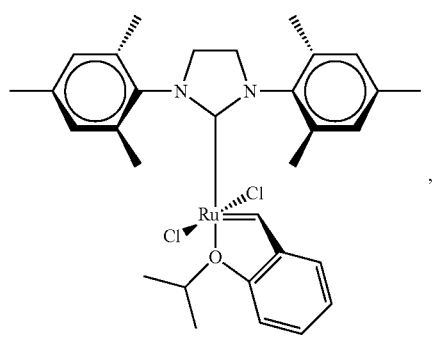
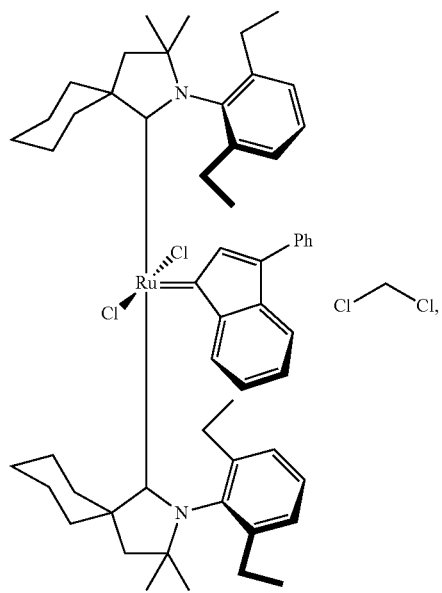
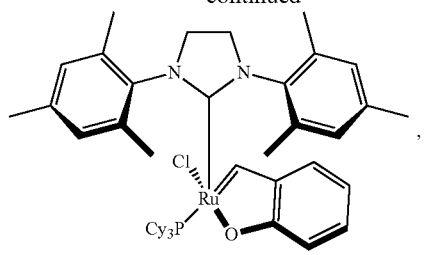
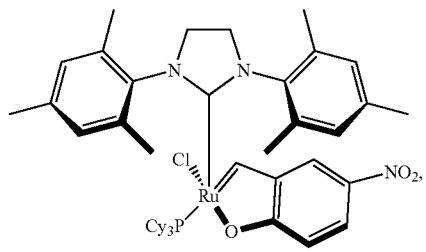
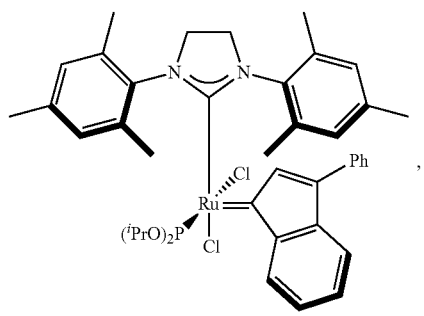
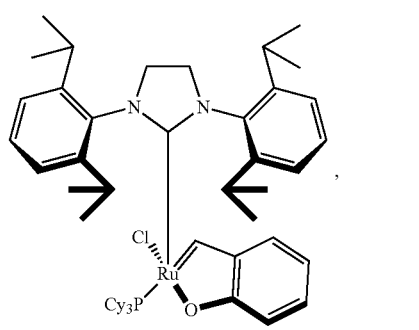
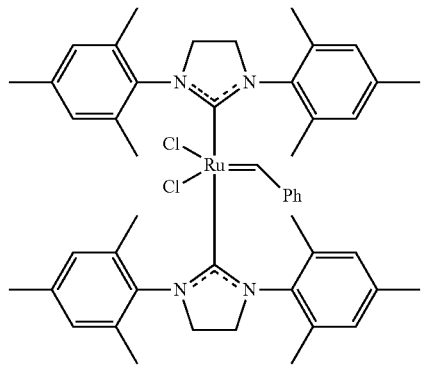

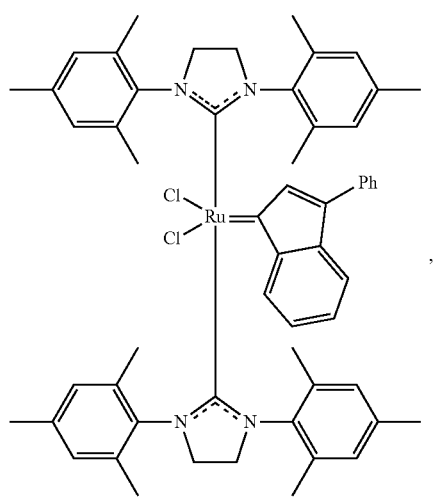
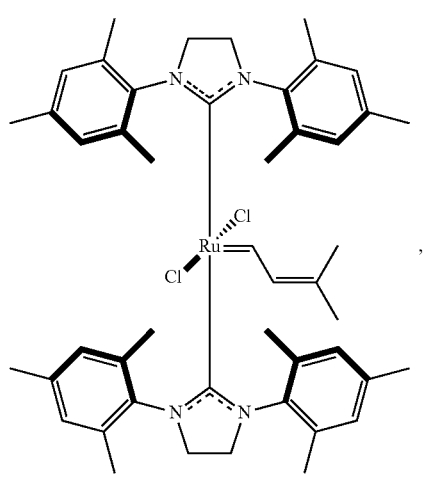
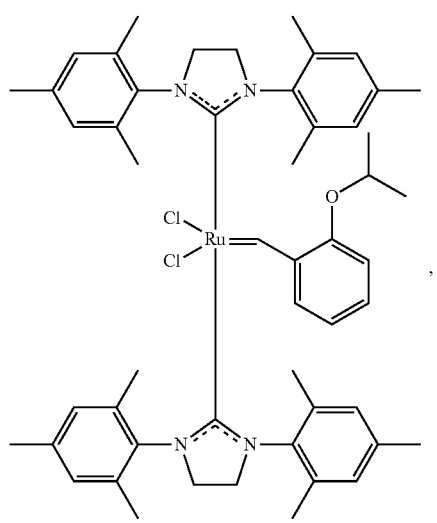
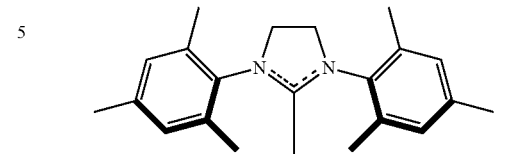
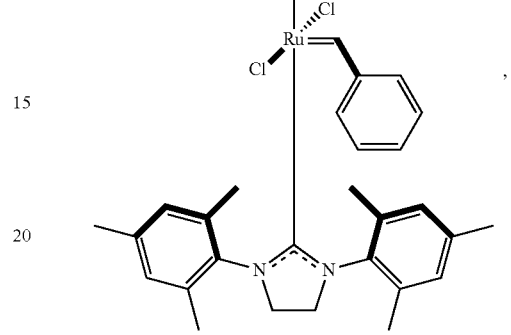
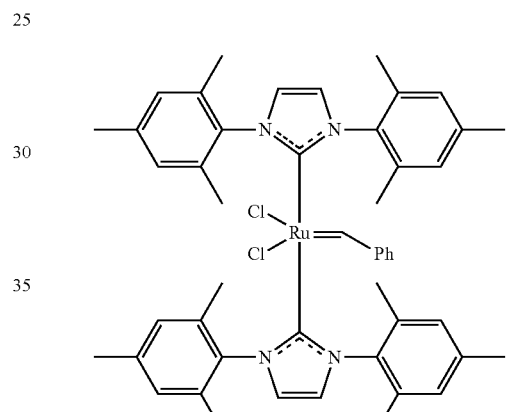
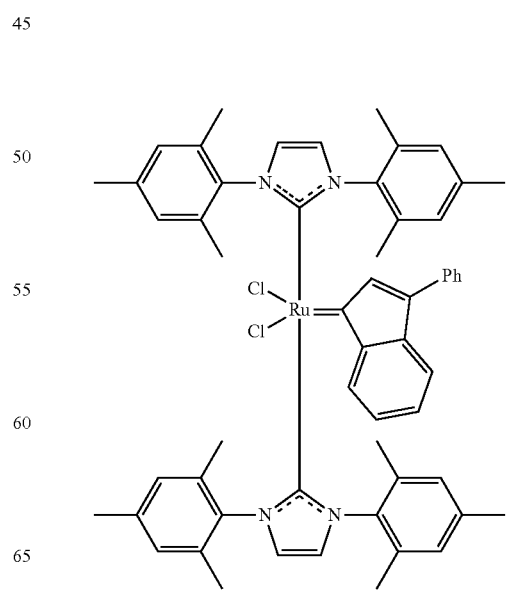

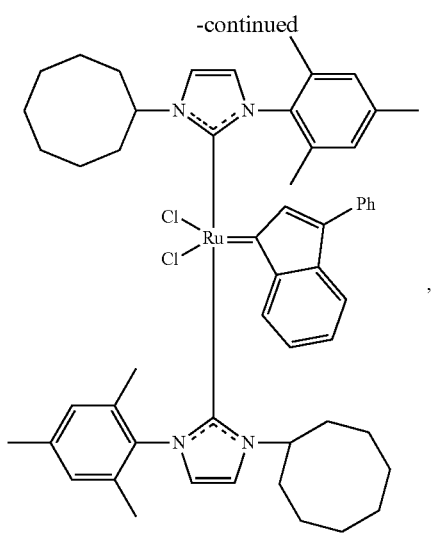
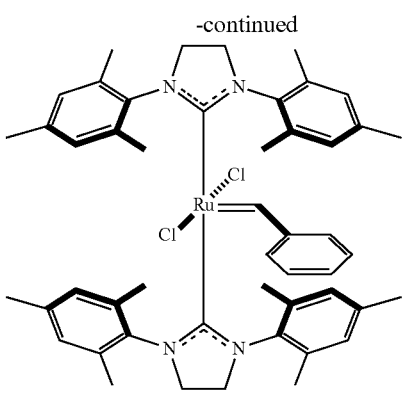
, or
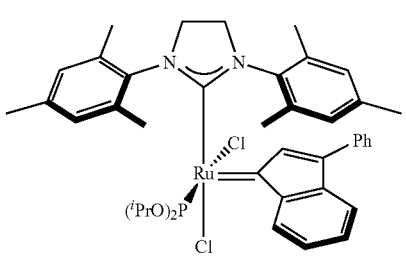
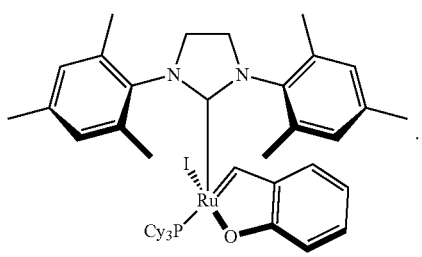
.
The latent Ru complex may include, for example:
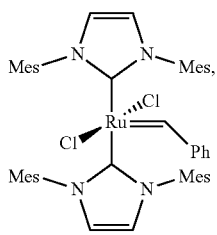
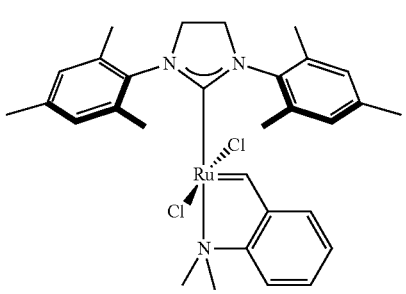
,
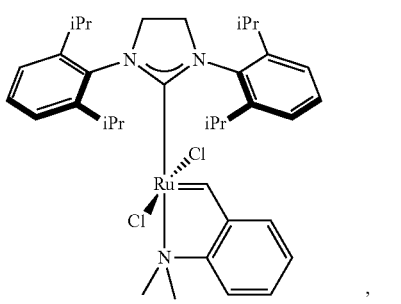
,
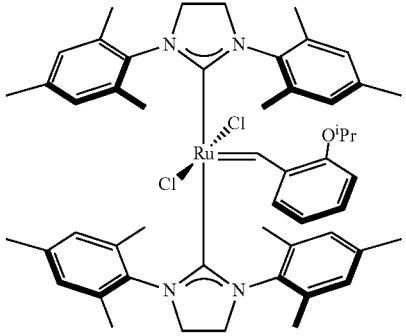
,

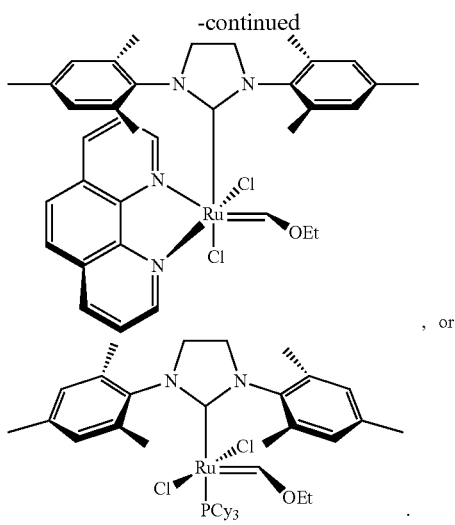

, or

The example of a Grubbs-type catalyst containing two N-heterocyclic carbene (NHC) ligands is presented in FIG. 1 since these ligands are typically the strongest to bind to Ru. Other strong ligands may include, for example, phosphines, phosphites, amines, ethers, thiols, and alcohols. As a result, the 16-electron complexes containing two NHC ligands may be very slow to participate in olefin metathesis. The catalyst may become active upon liberation of one NHC ligand to the 14-electron complex. The activated Ru complex may comprise at least one N-heterocyclic carbene (NHC) ligand. The activated Ru complex may comprise one N-heterocyclic carbene (NHC) ligand. The activated Ru complex may comprise a 14-electron species. Example 1 described herein provides a type of latent catalyst that is embodied by the disclosure.

The latent Ru complex may be present in the mixture at a concentration of at least 1 parts per billion (ppb) (e.g. 0.0000001% by weight), 0.1 parts per million (ppm) (e.g., 0.00001% by weight), 1 ppm (e.g., 0.0001% by weight), 10 ppm (e.g., 0.001% by weight), 100 ppm (e.g., 0.01% by weight), 1,000 ppm (e.g., 0.1% by weight), 10,000 ppm (e.g., 1% by weight), or more. The latent Ru complex may be present within a range defined by any of the two preceding values. The latent Ru complex may be present in the mixture at a concentration of at most 10,000 ppm (e.g., 1% by weight), 1,000 ppm (e.g., 0.1% by weight), 100 ppm (e.g., 0.01% by weight), 10 ppm (e.g., 0.001% by weight), 1 ppm (e.g., 0.0001% by weight), 0.1 ppm (e.g., 0.00001% by weight), 1 ppb (e.g. 0.0000001% by weight), or less. The latent Ru complex may be present within a range defined by any of the two preceding values. The latent Ru complex may be present in the mixture at a concentration from about 1 ppb (e.g., 0.0000001% by weight) to about 10,000 ppm (e.g., 1% by weight).

The initiator may be a photoacid (PAH), a photoacid generator (PAG), or a combination thereof. The initiator may be a PAH or a PAG. The initiator may be a PAH. The initiator may be a PAG. The PAH, PAG, or the combination thereof may be selected from the group consisting of sulfonium salts, iodonium salts, triazines, triflates, and oxime sulfonates. The initiator may be an iodonium salt. The initiator may be (4-tert-butylphenyl)iodonium hexafluorophosphate.

The initiator may activate the latent catalyst by displacing a first bound ligand or a first coordinated ligand (e.g., of the latent Ru complex). the first bound ligand or said first coordinated ligand (e.g., of the latent Ru complex) may be displaced with a second ligand. The second ligand may derive from the initiator. The second ligand may be the initiator. A ratio of coordination or bond strength of said first ligand and said second ligand may be less than 1, or more than 1.

The initiator may be present in the mixture at a concentration of at least 1 parts per billion (ppb) (e.g. 0.0000001% by weight), 0.1 parts per million (ppm) (e.g., 0.00001% by weight), 1 ppm (e.g., 0.0001% by weight), 10 ppm (e.g., 0.001% by weight), 100 ppm (e.g., 0.01% by weight), 1,000 ppm (e.g., 0.1% by weight), 10,000 ppm (e.g., 1% by weight), 100,000 ppm (e.g., 10% by weight), 150,000 ppm (e.g., 15% by weight), 200,000 ppm (e.g., 20% by weight), or more. The initiator may be present in the mixture at a concentration of at most 200,000 ppm (e.g., 25% by weight), 150,000 ppm (e.g., 15% by weight), 100,000 ppm (e.g., 10% by weight), 10,000 ppm (e.g., 1% by weight), 1,000 ppm (e.g., 0.1% by weight), 100 ppm (e.g., 0.01% by weight), 10 ppm (e.g., 0.001% by weight), 1 ppm (e.g., 0.0001% by weight), 0.1 ppm (e.g., 0.00001% by weight), 1 ppb (0.0000001% by weight), or less. The initiator may be present in the mixture at a concentration from about 0.1 ppm (e.g., 0.00001% by weight) to about 100,000 ppm (e.g., 10% by weight). The initiator may be present in the mixture at a concentration from about 1 ppm (e.g., 0.0001% by weight) to about 50,000 ppm (e.g., 5% by weight). The initiator may be present in the mixture at a concentration from about 1 ppm (e.g. 0.001% by weight) to about 25,000 ppm (e.g. 2.5% by weight). The initiator may be present in the mixture at a concentration within a range defined by any of the two preceding values.

The latent Ru complex and the initiator may be present in the mixture at a ratio of the Ru complex to the initiator at a ratio by moles of at least 0.00001:1.0, 0.0001:1.0, 0.001:1.0, 0.01:1.0, 0.025:1.0, 0.05:1.0, 0.075:1.0, 0.1:1.0, 0.5:1.0, 1.0:1.0, 1.5:1.0, 2.0:1.0, 3.0:1.0, 4.0:1.0, 5.0:1.0, 6.0:1.0, 7.0:1.0, 8.0:1.0, 9.0:1.0, 10:1.0, 15:1.0, 20:1.0, 25:1.0, or more of the Ru complex. The latent Ru complex and the initiator may be present in the mixture at a ratio of the Ru complex to the initiator at a ratio by moles of at most 25:1.0, 15:1.0, 10:1.0, 9.0:1.0, 8.0:1.0, 7.0:1.0, 6.0:1.0, 5.0:1.0, 6.0:1.0, 4.0:1.0, 3.0:1.0, 2.0:1.0, 1.0:1.0, 0.5:1.0, 0.1:1.0, 0.075:1.0, 0.05:1.0, 0.025:1.0, 0.01:1.0, 0.001:1.0, 0.0001:1.0, 0.00001:1.0, or less of the Ru complex. The latent Ru complex and the initiator may be present in the mixture at a ratio of the Ru complex to the initiator at a ratio by moles from 0.00001:1.0 to 10:1.0. The latent Ru complex and the initiator may be present in the mixture at a ratio of the Ru complex to the initiator at a ratio by moles from 0.02:1.0 to 1.0:1.0.

The activity of PAGs or PAHs to specific wavelengths of light may be modified by other light scattering moieties, such as, for example, sensitizers, such as 2-Isopropylthioxanthone (ITX), 1-chloro-4-propoxythioxanthone, 2,5-Bis(5-tert-butyl-benzoxazol-2-yl)thiophene, and aromatic organics such as naphthalene and perylene. Sensitizers, up-converters, down-converters, quantum dots, dyes, fluorophores or other light scattering moieties may be used to modulate the absorbance and activity of the photo-polymers described herein.

A stabilizer may be included to improve the dark stability of the compositions described herein. The stabilizer may include, for example, organic or inorganic Lewis or Bronsted bases, antioxidants, antiozonants, surfactants, oxygen scavengers, ligands, quenchers, light-absorbers, hindered-amine light stabilizers (HALS), amines, phosphines, phosphites, or any combination thereof.

The at least one polymer precursor may comprise a monomer. The at least one polymer precursor may comprise at least one olefin. The at least one olefin may be a cyclic olefin. The at least one olefin may be a norbornane-based olefin. Monomers may be, for example, norbornene, dicyclopentadiene, tricyclopentadiene, cyclooctene, cyclooctadiene, and alkyl norbornenes such as octylnorbornene. The cyclic olefin may be dicyclopentadiene or tricyclopentadiene. Higher molecular weight monomers include, for example, end-functionalized or side-chain functionalized polymers or oligomers or crosslinkers containing a metathesis-active end-group.

The electromagnetic radiation may have a wavelength of at least about 1 nanometers (nm), 10 nm, at least about 50 nm, at least about 100 nm, at least about 200 nm, at least about 300 nm, at least about 400 nm, at least about 500 nm, at least about 600 nm, at least about 700 nm, at least about 800 nm, at least about 900 nm, at least about 1 micrometer (µm), at least about 10 µm, at least about 50 µm, at least about 100 µm, at least about 200 µm, at least about 300 µm, at least about 400 µm, at least about 500 µm, at least about 600 µm, at least about 700 µm, at least about 800 µm, at least about 900 µm, at least about 1 millimeter (mm), at least about 10 mm, at least about 50 mm, at least about 100 mm, at least about 200 mm, at least about 300 mm, at least about 400 mm, at least about 500 mm, at least about 600 mm, at least about 700 mm, at least about 800 mm, at least about 900 mm, at least about 1 meter (m), at least about 10 m, at least about 100 m, at least about 200 m, at least about 300 m, at least about 400 m, at least about 500 m, at least about 600 m, at least about 700 m, at least about 800 m, at least about 900 m, at least about 1 kilometer (km), at least about 2 km, at least about 3 km, at least about 4 km, at least about 5 km, at least about 6 km, at least about 7 km, at least about 8 km, at least about 9 km, or more. The electromagnetic radiation may have a wavelength of at most about 10 km, at most about 9 km, at most about 8 km, at most about 7 km, at most about 6 km, at most about 5 km, at most about 4 km, at most about 3 km, at most about 2 km, at most about 1 km, at most about 900 m, at most about 800 m, at most about 700 m, at most about 600 m, at most about 500 m, at most about 400 m, at most about 300 m, at most about 200 m, at most about 100 m, at most about 10 m, at most about 1 m, at most about 900 mm, at most about 800 mm, at most about 700 mm, at most about 600 mm, at most about 500 mm, at most about 400 mm, at most about 300 mm, at most about 200 mm, at most about 100 mm, at most about 50 mm, at most about 10 mm, at most about 1 mm, at most about 900 µm, at most about 800 µm, at most about 700 µm, at most about 600 µm, at most about 500 µm, at most about 400 µm, at most about 300 µm, at most about 200 µm, at most about 100 µm, at most about 50 µm, at most about 10 µm, at most about 1 µm, at most about 900 nm, at most about 800 nm, at most about 700 nm, at most about 600 nm, at most about 500 nm, at most about 400 nm, at most about 300 nm, at most about 200 nm, at most about 100 nm, at most about 50 nm, at most about 10 nm, at most about 1 nm, or less. The electromagnetic radiation may have a wavelength from about 1 nanometers (nm) to about 10 kilometers (km). The electromagnetic radiation may have a wavelength from about 150 nm to about 2000 nm.

The electromagnetic radiation may derive from, for example, a laser beam, an incandescent light source, a fluorescent light source, an ultraviolet light source, which may derive from, for example, lamps, lasers, light emitting diodes (LEDs), sunlight and other photon sources. The electromagnetic radiation may be emitted from a laser, a digital light processing (DLP) projector, a lamp, a LED, a mercury arc lamp, a fiber optic, or liquid crystal display (LCD).

The method may be automated.

The oral product (e.g., a dental product or an orthodontic product) may be generated using anti-aliasing techniques. The oral product (e.g., a dental product or an orthodontic product) may be generated using greyscale pixels. The oral product (e.g., a dental product or an orthodontic product) may be generated top down. The oral product (e.g., a dental product or an orthodontic product) may be generated bottom up.

The oral product (e.g., a dental product or an orthodontic product) may be generated on a window material. The window material may be permeable to a gas. The window material may be permeable to oxygen ($O_2$). The window material may have a dead zone at the window interface. The window material may have a low surface energy (e.g., a surface free energy of at most 37 milliNewton per meter (mN/m) or less (e.g., at most 25 mN/m or less). The window material may have a surface free energy of at least 37 mN/m or more. The window material may comprise a transparent fluoropolymer.

The oral product (e.g., a dental product or an orthodontic product) may be generated in an atmosphere of substantially inert gas. The oral product (e.g., a dental product or an orthodontic product) may be generated in an atmosphere comprising less than or equal to 1% oxygen ($O_2$) 2% oxygen, 3% oxygen, 4% oxygen, 5% oxygen, 6% oxygen, 7% oxygen, 8% oxygen, 9% oxygen, 10% oxygen, 12% oxygen, 15% oxygen, 17% oxygen, 20% oxygen, or more. The oral product (e.g., a dental product or an orthodontic product) may be generated in an atmosphere comprising less than or equal to 1% oxygen, 0.8% oxygen, 0.6% oxygen, 0.4% oxygen, or 0.2% oxygen. The oral product (e.g., a dental product or an orthodontic product) may be generated in an atmosphere of inert gas. The oral product (e.g., a dental product or an orthodontic product) may be generated in an atmosphere nitrogen ($N_2$) or argon ($Ar_2$). The oral product (e.g., a dental product or an orthodontic product) may be generated in an atmosphere nitrogen ($N_2$). The oral product (e.g., a dental product or an orthodontic product) may be generated in an atmosphere argon ($Ar_2$).

The oral product (e.g., a dental product or an orthodontic product) may be generated at a temperature of 0° C., 10° C., 20° C., 30° C., 40° C., 50° C., 60° C., 70° C., 80° C., 90° C., 100° C., 110° C., 120° C., 130° C., 140° C., 150° C., 160° C., 170° C., 180° C., 190° C., 200° C., 220° C., 250° C., 300° C., or more. The oral product (e.g., a dental product or an orthodontic product) may be generated at a temperature of 300° C., 250° C., 220° C., 200° C., 190° C., 180° C., 170° C., 160° C., 150° C., 140° C., 130° C., 120° C., 110° C., 100° C., 90° C., 80° C., 70° C., 60° C., 50° C., 40° C., 30° C., 20° C., 10° C., 0° C., or less. The oral product (e.g., a dental product or an orthodontic product) may be printed at a temperature from 0° C. to 300° C. The oral product (e.g., a dental product or an orthodontic product) may be generated at a temperature from 20° C. to 50° C. The oral product (e.g., a dental product or an orthodontic product) may be generated at a temperature range defined by any of the two preceding values. The oral product (e.g., a dental product or an orthodontic product) may be generated at a temperature provided herein for the duration of the printing process.

The mixture may be exposed to electromagnetic radiation of an amount of at least 1 milliJoules/centimeters$^2$ (mJ/cm$^2$), 10 (mJ/cm²), 50 mJ/cm², 100 mJ/cm², 200 mJ/cm², 300 mJ/cm², 400 mJ/cm², 500 mJ/cm², 1,000 mJ/cm², 2,500 mJ/cm², 5,000 mJ/cm², 7,500 mJ/cm², 10,000 mJ/cm², 15,000 mJ/cm², 20,000 mJ/cm², 30,000 mJ/cm², 40,000 mJ/cm², 50,000 mJ/cm², 60,000 mJ/cm², 70,000 mJ/cm², 80,000 mJ/cm², 90,000 mJ/cm², 100,000 mJ/cm², or more. The mixture may be exposed to electromagnetic radiation of an amount of at most 100,000 mJ/cm², 90,000 mJ/cm², 80,000 mJ/cm², 70,000 mJ/cm², 60,000 mJ/cm², 50,000 mJ/cm², 40,000 mJ/cm², 30,000 mJ/cm², 20,000 mJ/cm², 15,000 mJ/cm², 10,000 mJ/cm², 7,500 mJ/cm², 5,000 mJ/cm², 2,500 mJ/cm², 1,000 mJ/cm², 500 mJ/cm², 400 mJ/cm², 300 mJ/cm², 200 mJ/cm², 100 mJ/cm², 50 mJ/cm², 10 mJ/cm², 1 mJ/cm², or less. The mixture may be exposed to electromagnetic radiation from 1 milliJoules/centimeters² mJ/cm² to about 100,000 mJ/cm². The mixture may be exposed to electromagnetic radiation from 100 milliJoules/centimeters² mJ/cm² to about 1,000 mJ/cm².

The composition described herein may further comprise an additive. Many types of additives may be used to modify the performance of the photopolymer, such as, for example (i) liquid properties (e.g., viscosity, stability, activity, cure speed, absorbance, surface energy, odor, etc.) and (ii) final cure polymer properties (e.g., modulus, toughness, impact strength, color, UV-stability, ductility, glass transition temperature, weather resistance, etc). These additives may include, for example, fillers, fibers, polymers, surfactants, inorganic particles, cells, viruses, biomaterials, rubbers, impact modifiers, graphite and graphene, colorants, dyes, pigments, carbon fiber, glass fiber, textiles, lignin, cellulose, wood, metal particles, or any combination thereof.

The compositions and methods described herein may vary depending on the application, material properties, and processing mechanism. Examples include: viscosities from about 5 centipoise (cP) to about 50,000 cP, latent catalyst loadings from about 0.5 ppm to about 1 wt %, PAG or PAH loadings from about 1 ppm to about 2 wt %, sensitizer loadings from about 0 (not present in mixture) to about 3 wt %, stabilizers from about 0 (not present in mixture) to about 5 wt % (e.g., 0.1 ppm to about 5 wt %), antioxidants from about 0 (not present in mixture) to about 5 wt % (e.g., 0.1 ppm to about 5 wt %), solvents from about 0 to about 90%, impact modifiers from about 0 (not present in mixture) to about 20 wt % (e.g., 10 ppm to about 20 wt %), and plasticizers from about 0 (not present in mixture) to about 3 wt % (e.g., 1 ppm to about 3 wt %), process temperatures from about −10° C. to about 220° C., oxygen concentrations from about 1 ppb to about 50%, exposure doses from about 1 milliJoules per centimeter² mJ/cm² to about 1 kiloJoules per centimeter² kJ/cm², irradiances from about 1 milliWatt per centimeter² mW/cm² to about 1 kiloWatt per centimeter² kW/cm², final Young's modulus from about 1 MegaPascals (MPa) to about 20 GigaPascals (GPa).

The photopolymers described herein may be relevant to many industrial processes, such as, for example, photolithography, stereolithography, inkjet printing, ultraviolet (UV) light-cured materials and adhesives, visible light-cured materials and adhesives, electron beam curing and lithography, multiphoton lithography, computed axial lithography, vat photopolymerization, nanoimprint lithography, additive manufacturing, direct write lithography, and other processes where directed energy is used to trigger polymerization. The photopolymerization may occur in a mold, on a substrate, in contact with another liquid, in a rotating container, on an actuated build platform, via an extrusion nozzle, or in any of the other myriad forms of controlling photopolymerizations. Heat or other forms of electromagnetic radiation may be used before, during or after curing to modify the kinetics of reactivity, tune the materials properties, or otherwise improve the photopolymerization process. The atmosphere of the curing or post-curing environment may be modified as well, including using, for example, nitrogen, argon or vacuum to eliminate oxygen and other unwanted reactive species.

Applications of this invention may include, for example, the manufacturing, processing, printing, lithography, molding, additive manufacturing, deposition, or production of an oral product (e.g., a dental product or an orthodontic product), including, for example, thermosets, thermoplastics, elastomers, resists, resins, waxes, rubbers, aerogels, glasses, composites and metamaterials. Possible use cases include, for example, the manufacturing of products, components, parts, tools, molds, bulk materials and intermediates for an oral product (e.g., a dental product or an orthodontic product), including, for example, an orthodontic aligner, a mouth guard, a surgical guide, a night guard, a splint, a denture, a prosthodontic, a dental prosthetic, an extra-oral appliance, a crown, a grill, dental jewelry, a brace, a surgical stent, a bruxism device (e.g., a bruxism guard), a sleep apnea device, a provisional or temporary restoration product (e.g., a temporary crown or a temporary bridge).

Printing:

In certain aspects, provided herein is a method for generating or printing an oral product (e.g., a dental product or an orthodontic product), comprising (a) providing a resin comprising (i) a latent ruthenium (Ru) complex, (ii) an initiator, and (iii) at least one polymer precursor; and (b) exposing the resin to electromagnetic radiation to activate the initiator, wherein upon activation, the initiator reacts with the latent Ru complex to generate an activated Ru complex, which activated Ru complex reacts with the polymer precursor to generate or print at least portion of the oral product (e.g., a dental product or an orthodontic product).

Provided in some embodiments herein is a method for producing an oral product (e.g., a dental product or an orthodontic product), comprising combining (i) a latent catalyst, (ii) an initiator, and (iii) at least one polymer precursor, wherein the oral product (e.g., a dental product or an orthodontic product) comprises at least one characteristic selected from the group consisting of: improved impact strength, chemical resistance, toughness, shear strength, tear strength, temperature stability, lightweight, biocompatibility, optical performance, dielectric permeability, flexural strength, creep, weathering, durability, and glass transition temperature.

The method may further comprise altering at least one characteristic of the oral product (e.g., a dental product or an orthodontic product) by subjecting the oral product (e.g., a dental product or an orthodontic product) to electromagnetic radiation (e.g., heat or light) after generating the oral product (e.g., a dental product or an orthodontic product).

Subsequent to subjecting the oral product (e.g., a dental product or an orthodontic product) to electromagnetic radiation (e.g., heat or light), at least one characteristic selected from the group consisting of modulus, tensile strength, crosslinking density, outgassing, leachability, biocompatibility, chemical resistance, color, biocompatibility, glass transition temperature, and viscosity, may be altered.

The oral product (e.g., a dental product or an orthodontic product) can be printed using any 3D printing method. The oral product (e.g., a dental product or an orthodontic product) can be printed using any 3D printing method that uses light (e.g., UV or visible light). The oral product (e.g., a dental product or an orthodontic product) can be printed using additive manufacturing, stereolithography, computed axial lithography, ink jetting, sintering, vat photopolymerization, multiphoton lithography, holographic lithography, hot lithography, IR lithography, direct writing, masked stereolithography, drop-on-demand printing, polyjet, digital-light projection (DLP), projection micro-stereolithography, nanoimprint lithography, photolithography. The oral product (e.g., a dental product or an orthodontic product) can be printed using additive manufacturing. The oral product (e.g., a dental product or an orthodontic product) can be printed using photo-activated additive manufacturing.

The printing method may be automated.

The oral product (e.g., a dental product or an orthodontic product) can be generated or printed adjacent to a support. The oral product (e.g., a dental product or an orthodontic product) can be removed from the support using robot-assistance, sonication, vibration, chemical swelling, chemical etching, laser ablation, laser cutting, blade cutting, or any combination thereof.

Figure 8:
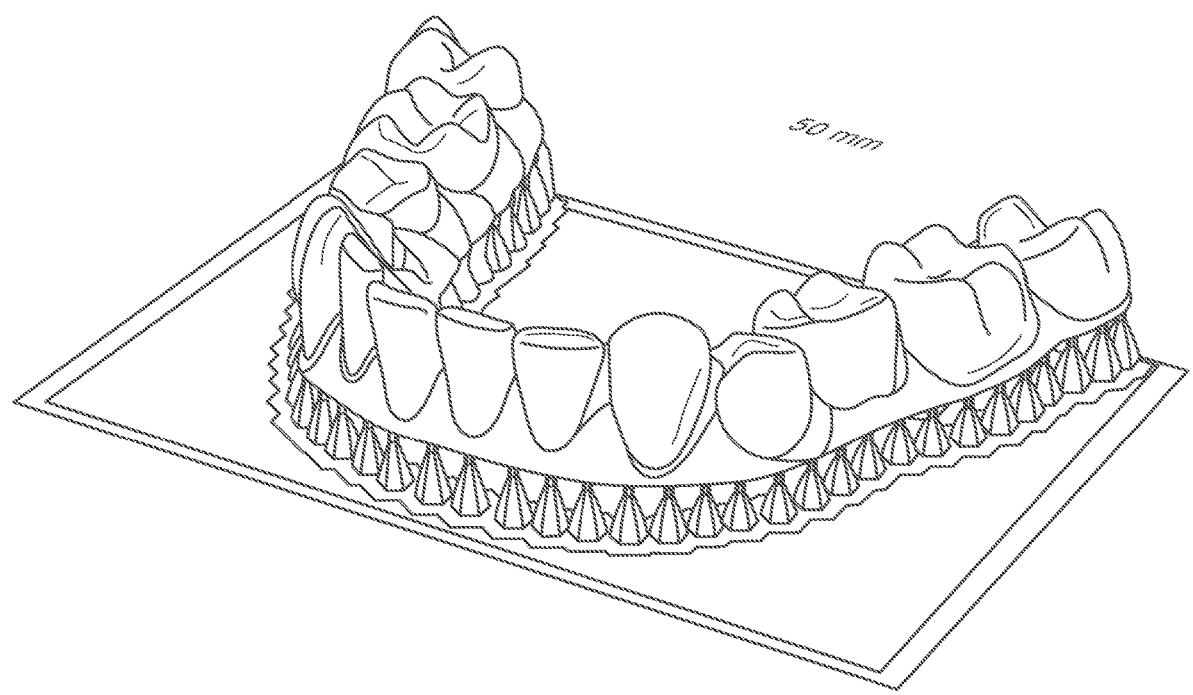
FIG. 8 shows an example of a digital rendition of an oral product made using a photopolymer.

The methods provided herein may provide control of digital variables of the printing process for the products provided herein. Such variables may include, for example, layer thickness, print orientation, support structures, wall thickness, shell thickness, or any combination thereof. An example of a digital rendition of a product provided herein is shown in FIG. 8.

The electromagnetic radiation may be emitted from a laser, a digital light processing (DLP) projector, a lamp, a light emitting diode (LED), a mercury arc lamp, a fiber optic, or liquid crystal display (LCD).

The oral product (e.g., a dental product or an orthodontic product) may be printed using anti-aliasing techniques. The oral product (e.g., a dental product or an orthodontic product) may be printed using greyscale pixels. The oral product (e.g., a dental product or an orthodontic product) may be printed top down. The oral product (e.g., a dental product or an orthodontic product) may be printed bottom up.

The oral product (e.g., a dental product or an orthodontic product) may be printed on a window material. The window material may allow for a gas to permeate to the object being printed. The window material may have a low surface energy. The window material may comprise a transparent fluoropolymer.

The oral product (e.g., a dental product or an orthodontic product) may be printed in an atmosphere of substantially inert gas. The oral product (e.g., a dental product or an orthodontic product) may be printed in an atmosphere comprising less than or equal to 1% oxygen ($O_2$). The oral product (e.g., a dental product or an orthodontic product) may be printed in an atmosphere comprising less than or equal to 0.2% $O_2$. The oral product (e.g., a dental product or an orthodontic product) may be printed in an atmosphere of inert gas. The oral product (e.g., a dental product or an orthodontic product) may be printed in an atmosphere nitrogen ($N_2$) or argon ($Ar_2$). The 3D object may be printed in an atmosphere nitrogen ($N_2$). The oral product (e.g., a dental product or an orthodontic product) may be printed in an atmosphere argon ($Ar_2$).

The oral product (e.g., a dental product or an orthodontic product) may be printed at a temperature of about −30° C., −20° C., −10° C., 0° C., 10° C., 20° C., 30° C., 40° C., 50° C., 60° C., 70° C., 80° C., 90° C., 100° C., 110° C., 120° C., 130° C., 140° C., 150° C., 160° C., 170° C., 180° C., 190° C., 200° C., 220° C., 250° C., 270° C., 300° C., or more. The oral product (e.g., a dental product or an orthodontic product) may be printed at a temperature of about 300° C., 270° C., 250° C., 220° C., 200° C., 190° C., 180° C., 170° C., 160° C., 150° C., 140° C., 130° C., 120° C., 110° C., 100° C., 90° C., 80° C., 70° C., 60° C., 50° C., 40° C., 30° C., 20° C., 10° C., 0° C., −10° C., −20° C., −30° C., or less. The oral product (e.g., a dental product or an orthodontic product) may be printed at a temperature from about −30° C. to about 300° C. The oral product (e.g., a dental product or an orthodontic product) may be printed at a temperature from 20° C. to 50° C. The oral product (e.g., a dental product or an orthodontic product) may be printed at a temperature provided herein for the duration of the printing process.

The mixture may be exposed to electromagnetic radiation of an amount of at least 1 milliJoules/centimeters$^2$ (mJ/cm$^2$), 10 mJ/cm$^2$, 20 mJ/cm$^2$, 30 mJ/cm$^2$, 40 mJ/cm$^2$, 50 mJ/cm$^2$, 100 mJ/cm$^2$, 200 mJ/cm$^2$, 300 mJ/cm$^2$, 400 mJ/cm$^2$, 500 mJ/cm$^2$, 1,000 mJ/cm$^2$, 2,500 mJ/cm$^2$, 5,000 mJ/cm$^2$, 7,500 mJ/cm$^2$, 10,000 mJ/cm$^2$, 15,000 mJ/cm$^2$, 20,000 mJ/cm$^2$, 30,000 mJ/cm$^2$, 40,000 mJ/cm$^2$, 50,000 mJ/cm$^2$, 60,000 mJ/cm$^2$, or more. The mixture may be exposed to electromagnetic radiation of an amount of at most 60,000 mJ/cm$^2$, 50,000 mJ/cm$^2$, 40,000 mJ/cm$^2$, 30,000 mJ/cm$^2$, 20,000 mJ/cm$^2$, 15,000 mJ/cm$^2$, 10,000 mJ/cm$^2$, 7,500 mJ/cm$^2$, 5,000 mJ/cm$^2$, 2,500 mJ/cm$^2$, 1,000 mJ/cm$^2$, 500 mJ/cm$^2$, 400 mJ/cm$^2$, 300 mJ/cm$^2$, 200 mJ/cm$^2$, 100 mJ/cm$^2$, 50 mJ/cm$^2$, 40 mJ/cm$^2$, 30 mJ/cm$^2$, 20 mJ/cm$^2$, 10 mJ/cm$^2$, 1 mJ/cm$^2$, or less. The mixture may be exposed to electromagnetic radiation within a range defined by any two of the preceding values. The mixture may be exposed to electromagnetic radiation from 1 milliJoules/centimeters$^2$ mJ/cm$^2$ to about 60,000 mJ/cm$^2$. The mixture may be exposed to electromagnetic radiation from 100 milliJoules/centimeters$^2$ mJ/cm$^2$ to about 1,000 mJ/cm$^2$.

The oral product (e.g., a dental product or an orthodontic product) may be printed by slicing. The oral product (e.g., a dental product or an orthodontic product) may be printed by slicing at a slice width of at least 1 micron (μm), 5 μm, 10 μm, 25 μm, 30 μm, 35 μm, 40 μm, 45 μm, 50 μm, 75 μm, 100 μm, 150 μm, 200 μm, 250 μm, 300 μm, 350 μm, 400 μm, 450 μm, 500 μm, 600 μm, 700 μm, 800 μm, 900 μm, 1,000 μm, 2,000 μm, 3,000 μm, 4,000 μm, 5,000 μm, 6,000 μm, 7,000 μm, 8,000 μm, 9,000 μm, 10,000 μm, or more. The oral product (e.g., a dental product or an orthodontic product) may be printed by slicing at a slice width of at most 10,000 μm, 9,000 μm, 8,000 μm, 7,000 μm, 6,000 μm, 5,000 μm, 4,000 μm, 3,000 μm, 2,000 μm, 1,000 μm, 900 μm, 800 μm, 700 μm, 600 μm, 500 μm, 450 μm, 400 μm, 350 μm, 300 μm, 250 μm, 200 μm, 150 μm, 100 μm, 75 μm, 50 μm, 45 μm, 40 μm, 35 μm, 30 μm, 25 μm, 10 μm, 5 μm, 1 μm, or less. The oral product (e.g., a dental product or an orthodontic product) may be printed by slicing at a slice width within a range defined by any two of the preceding values. The oral product (e.g., a dental product or an orthodontic product) may be printed by slicing at a slice width from 1 μm to 10,000 μm. The oral product (e.g., a dental product or an orthodontic product) may be printed by slicing at a slice width from 1 μm to 1,000 μm. The oral product (e.g., a dental product or an orthodontic product) may be printed by slicing at a slice width from 10 μm to 300 μm.

The oral product (e.g., a dental product or an orthodontic product) may be printed at a pixel size of at least 0.01 micron (μm), 0.05 μm, 0.1 μm, 0.5 μm, 1 μm, 2 μm, 3 μm, 4 μm, 5 μm, 6 μm, 7 μm, 8 μm, 9 μm, 10 μm, 15 μm, 20 μm, 25 μm, 50 μm, 75 μm, 100 μm, 150 μm, 200 μm, or more. The oral product (e.g., a dental product or an orthodontic product) may be printed at a pixel size of at most 200 μm, 150 μm, 100 μm, 75 μm, 50 μm, 25 μm, 20 μm, 15 μm, 10 μm, 9 μm, 8 μm, 7 μm, 6 μm, 5 μm, 4 μm, 3 μm, 2 μm, 1 μm, 0.5 μm, 0.1 μm, 0.05 μm, 0.01 μm, or less. The oral product (e.g., a dental product or an orthodontic product) may be printed at a pixel size from 0.01 μm to 200 μm. The oral product (e.g., a dental product or an orthodontic product) may be printed at a pixel size within a range defined by any two of the preceding values. The oral product (e.g., a dental product or an orthodontic product) may be printed at a pixel size from 5 μm to 100 μm.

The oral product (e.g., a dental product or an orthodontic product) may have a dimensional accuracy of at least 1 nanometer (nm), 10 nm, 50 nm, 100 nm, 500 nm, 1,000 nm, 2,000 nm, 3,000 nm, 4,000 nm, 5,000 nm, 10,000 nm, 15,000 nm, 25,000 nm, 50,000 nm, 75,000 nm, 100,000 nm, 200,000 nm, 300,000 nm, 400,000 nm, 500,000 nm, 600,000 nm, 700,000 nm, 800,000 nm, 900,000 nm, 1,000,000 nm, 2,000,000 nm, 3,000,000 nm, 4,000,000 nm, 5,000,000 nm, 10,000,000 nm, or more. The oral product (e.g., a dental product or an orthodontic product) may have a dimensional accuracy of at most 10,000,000 nm, 5,000,000 nm, 4,000,000 nm, 3,000,000 nm, 2,000,000 nm, 1,000,000 nm, 900,000 nm, 800,000 nm, 700,000 nm, 600,000 nm, 500,000 nm, 400,000 nm, 300,000 nm, 200,000 nm, 100,000 nm, 75,000 nm, 50,000 nm, 25,000 nm, 15,000 nm, 10,000 nm, 5,000 nm, 4,000 nm, 3,000 nm, 2,000 nm, 1,000 nm, 500 nm, 100 nm, 50 nm, 10 nm, 1 nm, or less. The oral product (e.g., a dental product or an orthodontic product) may have a dimensional accuracy within a range defined by any two of the preceding values. The oral product (e.g., a dental product or an orthodontic product) may have a dimensional accuracy from about 1 nm to about 10,000,000 nm. The oral product (e.g., a dental product or an orthodontic product) may have a dimensional accuracy from about 1,000 nm to about 1,000,000 nm. The dimensional accuracy may be a percentage deviation from the predetermined dimension. The oral product (e.g., a dental product or an orthodontic product) may have a dimensional accuracy of at least +/−0.0001%, +/−0.001%, +/−0.01%, +/−0.1%, +/−1%, +/−10%, or +/−100%. The oral product (e.g., a dental product or an orthodontic product) may have a dimensional accuracy of at most +/−100%, +/−10%, +/−1%, +/−0.1%, +/−0.01%, +/−0.001%, +/−0.0001%, or less. The oral product (e.g., a dental product or an orthodontic product) may have a dimensional accuracy within a range defined by any two of the preceding values. The oral product (e.g., a dental product or an orthodontic product) may have a dimensional accuracy from about +/−0.0001% to about +/−100%. The oral product (e.g., a dental product or an orthodontic product) may have a dimensional accuracy of less than or equal to +/−1%. The oral product (e.g., a dental product or an orthodontic product) may have a dimensional accuracy from about +/−0.0001% to about +/−1%.

The oral product (e.g., a dental product or an orthodontic product) may have a photopolymer shrinkage or expansion of at least +/−0.0001%, +/−0.001%, +/−0.01%, +/−0.1%, +/−1%, +/−10%, +/−25%, +/−50%, +/−100% or more. The oral product (e.g., a dental product or an orthodontic product) may have a photopolymer shrinkage or expansion of at most +/−100%, +/−50%, +/−25%, +/−10%, +/−1%, +/−0.1%, +/−0.01%, +/−0.001%, +/−0.0001% or less. The oral product (e.g., a dental product or an orthodontic product) may have a photopolymer shrinkage or expansion within a range defined by any two of the preceding values. The oral product (e.g., a dental product or an orthodontic product) may have a photopolymer shrinkage or expansion from about +/−0.0001% to about 100%. The oral product (e.g., a dental product or an orthodontic product) may have a photopolymer shrinkage or expansion of less than or equal to +/−4%. The oral product (e.g., a dental product or an orthodontic product) may have a photopolymer shrinkage or expansion from about +/−0.001% to about +/−4%.

The oral product (e.g., a dental product or an orthodontic product) may be any polymer or object provided herein.

Figure 9A:
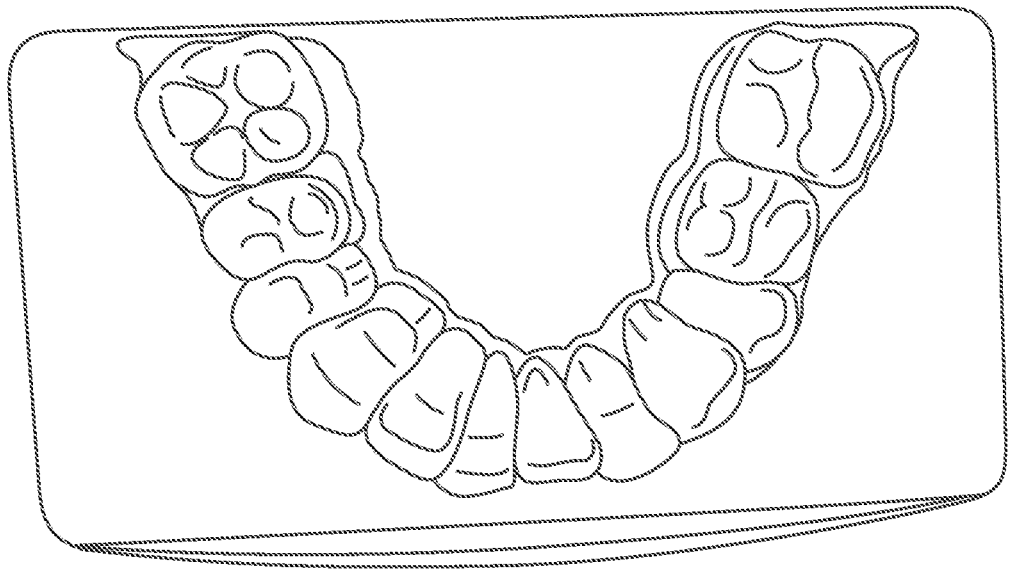
FIG. 9A shows a top view of an example of an oral product (e.g., green part) made using a photopolymer.
Figure 9B:
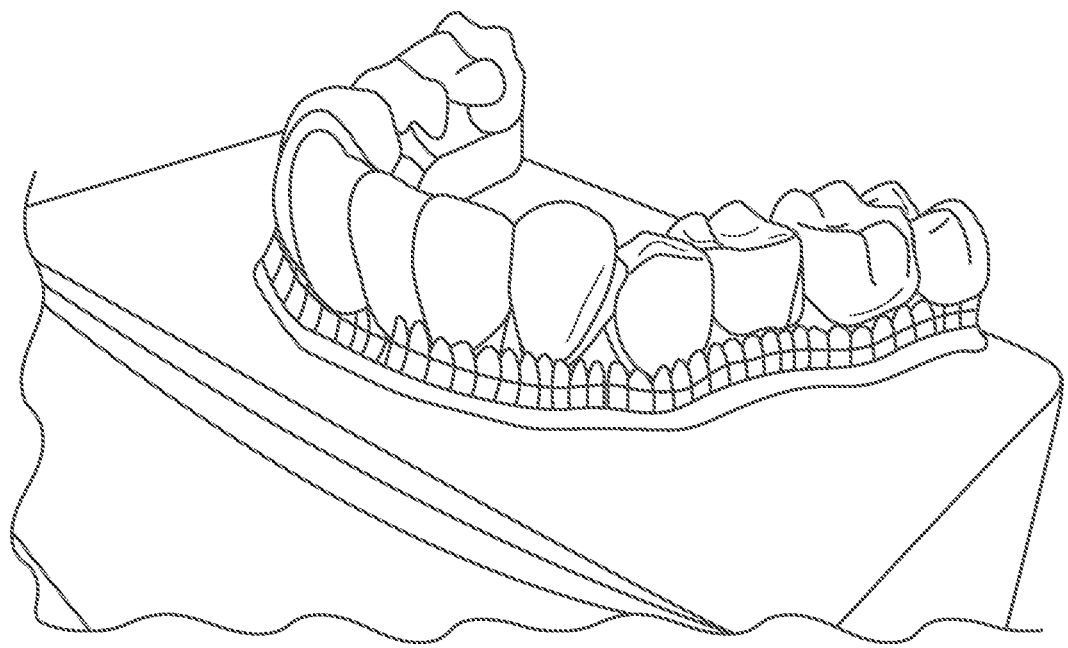
FIG. 9B shows a side view of an example of an oral product (e.g., green part) made using a photopolymer.
Figure 10:
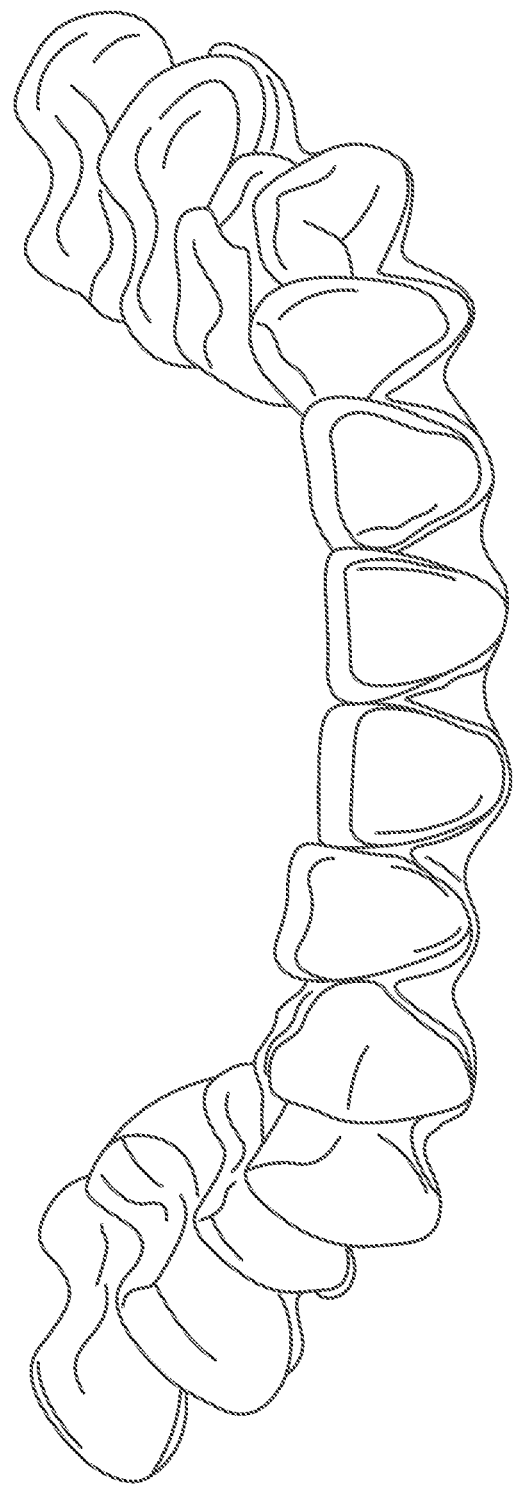
FIG. 10 shows an example of an orthodontic aligner made using a photopolymer.

Example oral products (e.g., a dental product or an orthodontic product) produced using the methods and compositions provided herein are shown in FIG. 9A, FIG. 9B (e.g., green part of dental aligner), and FIG. 10 (e.g., orthodontic aligner).

Post-Processing:

A oral product (e.g., a dental product or an orthodontic product), or a portion thereof, provided herein can be treated to further processes after printing at least a portion of the oral product (e.g., a dental product or an orthodontic product) (e.g., a green part). The method may further comprise altering at least one characteristic of oral product (e.g., a dental product or an orthodontic product) by subjecting the oral product (e.g., a dental product or an orthodontic product) to electromagnetic radiation (e.g., heat or light) after generating the oral product (e.g., a dental product or an orthodontic product). Subsequent to subjecting the oral product (e.g., a dental product or an orthodontic product), or a portion thereof, to electromagnetic radiation (e.g., heat or light), at least one characteristic selected from the group consisting of modulus, tensile strength, crosslinking density, outgassing, leachability, biocompatibility, chemical resistance, color, biocompatibility, glass transition temperature, and viscosity, may be altered.

In some embodiments, the method further comprises curing the oral product (e.g., a dental product or an orthodontic product), or a portion thereof. The curing may take place after any one of (a), (b), or both (a) and (b) provided herein. The curing may take place after (a) and (b) provided herein. In some embodiments, the method further comprises post-curing the oral product (e.g., a dental product or an orthodontic product), or a portion thereof.

Post-curing the oral product (e.g., a dental product or an orthodontic product), or a portion thereof, can comprise subjecting the the oral product (e.g., a dental product or an orthodontic product), or a portion thereof, to electromagnetic radiation (e.g., light or heat). The oral product (e.g., a dental product or an orthodontic product), or a portion thereof, be subjected to ultraviolet radiation, visible (light) radiation, convection heating, conduction heating, radiation heating, or any combination thereof. The electromagnetic radiation may have a wavelength of at least 1 nanometer (nm) 10 nm, 50 nm, 100 nm, 500 nm, 1,000 nm, 2,000 nm, 3,000 nm, 4,000 nm, 5,000 nm, 10,000 nm, 15,000 nm, 25,000 nm, 50,000 nm, 75,000 nm, 100,000 nm, 200,000 nm, 300,000 nm, 400,000 nm, 500,000 nm, 600,000 nm, 700,000 nm, 800,000 nm, 900,000 nm, 1,000,000 nm, 2,000,000 nm, 3,000,000 nm, 4,000,000 nm, 5,000,000 nm, 10,000,000 nm, or more. The electromagnetic radiation may have a wavelength of at most 10,000,000 nm, 5,000,000 nm, 4,000,000 nm, 3,000,000 nm, 2,000,000 nm, 1,000,000 nm, 900,000 nm, 800,000 nm, 700,000 nm, 600,000 nm, 500,000 nm, 400,000 nm, 300,000 nm, 200,000 nm, 100,000 nm, 75,000 nm, 50,000 nm, 25,000 nm, 15,000 nm, 10,000 nm, 5,000 nm, 4,000 nm, 3,000 nm, 2,000 nm, 1,000 nm, 500 nm, 100 nm, 50 nm, 10 nm, 1 nm, or less. The electromagnetic radiation may have a wavelength within a range defined by any two of the preceding values. The electromagnetic radiation may have a wavelength from about 1 nm to about 10,000,000 nm. The electromagnetic radiation may have a wavelength from about 1,000 nm to about 1,000,000 nm. The electromagnetic radiation may have a wavelength of at most 1,000,000 nm. The electromagnetic radiation may have a wavelength from 1 nanometer (nm) to 1,00,000 nm.

Post-curing the oral product (e.g., a dental product or an orthodontic product), or a portion thereof, may alter at least one characteristic of the the oral product (e.g., a dental product or an orthodontic product), or a portion thereof. Post-curing the dental product or the orthodontic product may alter the impact strength, chemical resistance, toughness, shear strength, tear strength, temperature stability, lightweight, biocompatibility, optical performance, dielectric permeability, flexural strength, creep, weathering, durability, glass transition temperature, or any combination thereof.

In some embodiments, the method further comprises cleaning the oral product (e.g., a dental product or an orthodontic product). The cleaning may take place after any one of (a), (b), or both (a) and (b) provided herein. The cleaning may take place after (b) provided herein. The cleaning may take place after (a) and (b) provided herein. The oral product (e.g., a dental product or an orthodontic product) can be cleaned using a solvent, agitation, sonication, stirring, air drying, air knives, automated washing, or any combination thereof. The oral product (e.g., a dental product or an orthodontic product) can be cleaned using air, sonication, solvent, or a combination thereof. The cleaning solution may comprise additives to modify the properties of the oral product (e.g., a dental product or an orthodontic product). The cleaning may alter the dimensional accuracy, modulus, surface roughness, impact strength, chemical resistance, toughness, shear strength, tear strength, temperature stability, lightweight, biocompatibility, optical performance, dielectric permeability, flexural strength, creep, weathering, durability, glass transition temperature, or any combination thereof.

A surface of the oral product (e.g., a dental product or an orthodontic product) can be smoothed, brightened, coated, sealed, sterilized, or a combination thereof. The surface of the oral product (e.g., a dental product or an orthodontic product) can be smoothed or sterilized during, before or subsequent to cleaning the oral product (e.g., a dental product or an orthodontic product). The surface of the oral product (e.g., a dental product or an orthodontic product) can be smoothed or sterilized during or subsequent to cleaning the oral product (e.g., a dental product or an orthodontic product).

A surface of the oral product (e.g., a dental product or an orthodontic product) can be cleaned, smoothed, brightened, coated, sealed, or sterilized using ethylene oxide, cold sterilization, alcohol, autoclaving, soap, ultraviolet sterilization, plasma treatment, coating deposition, etching, polishing (e.g., vibration polishing, tumbling, or solvent polishing), or any combination thereof.

Oral Products:

The oral product (e.g., a dental product or an orthodontic product) may be a body, a product, a component, a part, a tool, a mold, a bulk material, an intermediate, or any combination thereof for many oral (e.g., dental) applications. The oral product (e.g., a dental product or an orthodontic product) may be a component of an oral product (e.g., a dental product or an orthodontic product) provided herein. The oral product (e.g., a dental product or an orthodontic product) may be, for example, an orthodontic aligner, a mouth guard, a surgical guide, a night guard, a splint, a denture, a prosthodontic, a dental prosthetic, an extra-oral appliance, a crown, a grill, dental jewelry, a brace, a surgical stent, a bruxism device (e.g., a bruxism guard), a sleep apnea device, a provisional or temporary restoration product (e.g., a temporary crown or a temporary bridge).

The oral product may be a dental product or an orthodontic product.

The oral product (e.g., a dental product or an orthodontic product) may be a green part provided herein.

In certain aspects, provided herein is an oral product (e.g., a dental product or an orthodontic product), comprising a body comprising a polymer (e.g., a cyclic olefin polymer), a (e.g., deactivated) Ru complex, a (e.g., deactivated) initiator, a sensitizer, or any combination thereof. In certain aspects, provided herein is an oral product (e.g., a dental product or an orthodontic product), comprising a body comprising a cyclic olefin polymer.

A body provided herein may comprise one or more additive. The additive may modify at least one property or characteristic of oral product (e.g., a dental product or an orthodontic product). The additive may modify the modulus, toughness, impact strength, color, UV-stability, ductility, glass transition temperature, weather resistance, flammability or surface energy of oral product (e.g., a dental product or an orthodontic product). The additive may modify at least one property, feature, or characteristic of the oral product (e.g., a dental product or an orthodontic product). The additive may modify the photomodulus coefficient, green strength, pot life, shelf life, printing accuracy, critical exposure, penetration depth, print speed or optimal print environment or temperature of the oral product (e.g., a dental product or an orthodontic product).

The additive may be selected from the group consisting of a pigment (e.g., a white pigment), a dye (e.g., a fluorophore), an optical brightener, a fluorescent whitening agent, a bluing agent, a decorative particle, a nanoparticle, a dielectric mirror, a photonic crystal, a non-linear optical media, a white pigments, an impact modifier, and a plasticizer.

The dental product or the orthodontic product may be selected from the group consisting of a orthodontic aligner, a mouth guard, a surgical guide, a night guard, a splint, a denture, a prosthodontic, a dental prosthetic, an extra-oral appliance, a crown, a grill, dental jewelry, a brace, a surgical stent, a bruxism device (e.g., a bruxism guard), a sleep apnea device, a provisional or temporary restoration product (e.g., a temporary crown or a temporary bridge). In some embodiments, the dental product or the orthodontic product is an orthodontic aligner.

The oral product (e.g., a dental product or an orthodontic product) can comprise at least one sub-component. The oral product (e.g., a dental product or an orthodontic product) can have a component geometry. The oral product (e.g., a dental product or an orthodontic product) may comprise at least one sub-component, a component geometry, or any combination thereof.

The sub-component may be a functional sub-component, an aesthetic sub-component, or a combination thereof. The sub-component may be a functional sub-component. The sub-component may be an aesthetic sub-component.

The component geometry can be a spatial gradient. The spatial gradient can be a spatial variability in thickness, modulus, ductility, color, or any combination thereof.

The component geometry may comprise at least one topology. The at least one topology can be configured to move one or more tooth (e.g., move, rotate, align, or any combination thereof) of an individual wearing the oral product (e.g., a dental product or an orthodontic product). The at least one topology can allow the oral product (e.g., a dental product or an orthodontic product) to move teeth, rotate teeth, align teeth, or any combination thereof. The at least one topology may allow the oral product (e.g., a dental product or an orthodontic product) to move, rotate, or a combination thereof.

The at least one sub-component or the component geometry may be selected from the group consisting of a void, a lattice structure, a triple periodic minimal surface, a personalized geometry, a stylized geometry, an aesthetic geometry, a digitally-defined surface texture, a ring, a tori, a tube, a fluidic channel, a grip, an anchor, a connector, a hook, a ratchet, a valve, and a clip.

The oral product (e.g., a dental product or an orthodontic product) may have a modulus of at least 0.00001 megapascal (MPa), 0.0001 MPa, 0.001 MPa, 0.01 MPa, 0.1 MPa, 1 MPa, 50 MPa, 100 MPa, 250 MPa, 500 MPa, 1,000 MPa, 2,000 MPa, or more. The oral product (e.g., a dental product or an orthodontic product) may have a modulus of at most 2,000 MPa, 1,000 MPa, 500 MPa, 250 MPa, 100 MPa, 50 MPa, 1 MPa, 0.1 MPa, 0.01 MPa, 0.001 MPa, 0.0001 MPa, 0.00001 MPa, or less. The oral product (e.g., a dental product or an orthodontic product) may have a modulus within a range defined by any two of the preceding values. The oral product (e.g., a dental product or an orthodontic product) may have a modulus from about 100 kilopascals (KPa) to about 10 gigapascal (GPa). The oral product (e.g., a dental product or an orthodontic product) may have a modulus from 1 MPa to 20 GPa. The modulus may be from 10 MPa to 10 GPa.

The oral product (e.g., a dental product or an orthodontic product) may have a flexural modulus of at least 0.0001 megapascal (MPa), 0.001 MPa, 0.01 MPa, 0.1 MPa, 1 megapascal (MPa), 50 MPa, 100 MPa, 250 MPa, 500 MPa, 1,000 MPa, 2,000 MPa, or more. The oral product (e.g., a dental product or an orthodontic product) may have a flexural modulus of at most 2,000 MPa, 1,000 MPa, 500 MPa, 250 MPa, 100 MPa, 50 MPa, 1 MPa, 0.1 MPa, 0.01 MPa, 0.001 MPa, 0.0001 MPa, or less. The oral product (e.g., a dental product or an orthodontic product) may have a flexural modulus within a range defined by any two of the preceding values. The oral product (e.g., a dental product or an orthodontic product) may have a flexural modulus from 1 MPa to 20 GPa. The flexural modulus may be from 10 MPa to 10 GPa.

The oral product (e.g., a dental product or an orthodontic product) may have a heat-deflection temperature (HDT) of at least 0 degrees Celsius (° C.), 10° C., 15° C., 20° C., 25° C., 50° C., 60° C., 70° C., 80° C., 90° C., 100° C., 110° C., 120° C., 130° C., 140° C., 150° C., 160° C., 170° C., 180° C., 190° C., 200° C., 210° C., 220° C., 230° C., 240° C., 250° C., 260° C., 270° C., 280° C., 290° C., 300° C., 350° C., 400° C., or more. The oral product (e.g., a dental product or an orthodontic product) may have a HDT of at most 400° C., 350° C., 300° C., 290° C., 280° C., 270° C., 260° C., 250° C., 240° C., 230° C., 220° C., 210° C., 200° C., 190° C., 180° C., 170° C., 160° C., 150° C., 140° C., 130° C., 120° C., 110° C., 100° C., 90° C., 80° C., 70° C., 60° C., 50° C., 25° C., 20° C., 15° C., 10° C., 0° C., or less. The oral product (e.g., a dental product or an orthodontic product) may have a HDT within a range defined by any two of the preceding values. The oral product (e.g., a dental product or an orthodontic product) may have a HDT from 0° C. to 400° C. The HDT may be from 50° C. to 200° C.

The oral product (e.g., a dental product or an orthodontic product) may have a glass transition temperature ($T_g$) of at least −100 degrees Celsius (° C.), −50° C., 0° C., 50 degrees ° C., 50° C., 100° C., 150° C., 200° C., 250° C., 300° C., 350° C., 400° C., or more. The oral product (e.g., a dental product or an orthodontic product) may have a $T_g$ of at most 400° C., 350° C., 300° C., 250° C., 200° C., 150° C., 100° C., 50° C., 0° C., −50° C., −100° C., or less. The oral product (e.g., a dental product or an orthodontic product) may have a $T_g$ within a range defined by any two of the preceding values. The oral product (e.g., a dental product or an orthodontic product) may have a $T_g$ from −100° C. to 400° C. The oral product (e.g., a dental product or an orthodontic product) may have a $T_g$ from −50° C. to 250° C. The $T_g$ may be from 100° C. to 200° C.

The oral product (e.g., a dental product or an orthodontic product) may have an impact strength of at least 1 Joule per meter (J/m), 10 J/m, 20 J/m, 50 J/m, 70 J/m, 100 J/m, 120 J/m, 140 J/m, 150 J/m, 170 J/m, 200 J/m, 220 J/m, 250 J/m, 300 J/m, 500 J/m, 1,000 J/m, 2,000 J/m, 3,000 J/m, 4,000 J/m, 5,000 J/m, 6,000 J/m, 7,000 J/m, 8,000 J/m, 9,000 J/m, 10,000 J/m, or more. The oral product (e.g., a dental product or an orthodontic product) may have an impact strength of at most 10,000 J/m, 9,000 J/m, 8,000 J/m, 7,000 J/m, 6,000 J/m, 5,000 J/m, 4,000 J/m, 3,000 J/m, 2,000 J/m, 1,000 J/m, 500 J/m, 300 J/m, 270 J/m, 250 J/m, 220 J/m, 200 J/m, 170 J/m, 150 J/m, 140 J/m, 120 J/m, 100 J/m, 70 J/m, 50 J/m, 20 J/m, 10 J/m, 1 J/m, or less. The oral product (e.g., a dental product or an orthodontic product) may have an impact strength within a range defined by any two of the preceding values. The oral product (e.g., a dental product or an orthodontic product) may have an impact strength from 1 J/m to 10,000 J/m. The impact strength may be from 10 J/m to 1,000 J/m. The impact strength may be from 30 J/m to 700 J/m. The impact strength of the oral product (e.g., a dental product or an orthodontic product) may be obtained using a notched Izod impact strength test.

The oral product (e.g., a dental product or an orthodontic product) may have an impact strength retention of at least 1%, 10%, 20%, 30%, 40%, 50%, 60%, 70%, 80%, 90%, or 100%. The oral product (e.g., a dental product or an orthodontic product) may have an impact strength retention of at most 100%, 90%, 80%, 70%, 60%, 50%, 40%, 30%, 20%, 10%, 1%, or less. The oral product (e.g., a dental product or an orthodontic product) may have an impact strength retention within a range defined by any two of the preceding values. The oral product (e.g., a dental product or an orthodontic product) may have an impact strength retention from 10% to 100%. The impact strength retention may be at a temperature of at least −273 degrees Celsius (° C.), −200° C., −100° C., −50° C., 0° C., 50° C., 100° C., 200° C., 300° C., or more. The impact strength retention may be at a temperature of at least 300° C., 200° C., 100° C., 50° C., 0° C., −50° C., −100° C., −200° C., or less. The impact strength retention may be at a temperature within a range defined by any two of the preceding values.

The oral product (e.g., a dental product or an orthodontic product) may have a tensile strength of at least 0.00001 megapascal (MPa), 0.0001 MPa, 0.001 MPa, 0.01 MPa, 0.1 MPa, 1 MPa, 50 MPa, 100 MPa, 250 MPa, 500 MPa, 1,000 MPa, or more. The oral product (e.g., a dental product or an orthodontic product) may have a tensile strength of at most 1,000 MPa, 500 MPa, 250 MPa, 100 MPa, 50 MPa, 1 MPa, 0.1 MPa, 0.01 MPa, 0.001 MPa, 0.0001 MPa, 0.00001 MPa, or less. The oral product (e.g., a dental product or an orthodontic product) may have a tensile strength within a range defined by any two of the preceding values. The oral product (e.g., a dental product or an orthodontic product) may have a tensile strength from about 100 kilopascals (KPa) to about 10 gigapascal (GPa). The oral product (e.g., a dental product or an orthodontic product) may have a tensile strength from 1 MPa to 20 GPa. The tensile strength may be from 10 MPa to 10 GPa.

The oral product (e.g., a dental product or an orthodontic product) may have a flexural strain at max stress of at least 0.00001 megapascal (MPa), 0.0001 MPa, 0.001 MPa, 0.01 MPa, 0.1 MPa, 1 MPa, 50 MPa, 100 MPa, 250 MPa, 500 MPa, 1,000 MPa, 1,500 MPa, or more. The oral product (e.g., a dental product or an orthodontic product) may have a flexural strain at max stress of at most 1,500 MPa, 1,000 MPa, 500 MPa, 250 MPa, 100 MPa, 50 MPa, 1 MPa, 0.1 MPa, 0.01 MPa, 0.001 MPa, 0.0001 MPa, 0.00001 MPa, or less. The oral product (e.g., a dental product or an orthodontic product) may have a flexural strain at max stress within a range defined by any two of the preceding values. The oral product (e.g., a dental product or an orthodontic product) may have a flexural strain at max stress from about 100 kilopascals (KPa) to about 1500 megapascals (KPa). The oral product (e.g., a dental product or an orthodontic product) may have a flexural strain at max stress from 1 MPa to 350 MPa.

The oral product (e.g., a dental product or an orthodontic product) may have a strain at yield of at least 0.1%, 1%, 5%, 50%, 100%, 200%, 300%, 400%, 500%, 1,000%, 2,000%, 3,000%, 4,000%, 5,000%, 6,000%, 7,000%, 8,000%, 9,000%, 10,000%, or more. The oral product (e.g., a dental product or an orthodontic product) may have a strain at yield of at most 10,000%, 9,000%, 8,000%, 7,000%, 6,000%, 5,000%, 4,000%, 3,000%, 2,000%, 1,000%, 500%, 400%, 300%, 200% 100%, 50%, 5%, 1%, 0.1%, or less. The oral product (e.g., a dental product or an orthodontic product) may have a strain at yield within a range defined by any two of the preceding values. The oral product (e.g., a dental product or an orthodontic product) may have a strain at yield from 0.1% to 10,000%. The strain at yield may be from 1% to 500%.

The oral product (e.g., a dental product or an orthodontic product) may have an elongation at break of at least 1%, 2% 5%, 50%, 100%, 200%, 300%, 400%, 500%, 1,000%, 2,000%, 3,000%, 4,000%, 5,000%, 6,000%, 7,000%, 8,000%, 9,000%, 10,000%, or more. The oral product (e.g., a dental product or an orthodontic product) may have an elongation at break of at most 10,000%, 9,000%, 8,000%, 7,000%, 6,000%, 5,000%, 4,000%, 3,000%, 2,000%, 1,000%, 500%, 400%, 300%, 200% 100%, 50%, 5%, 2%, 1%, or less. The oral product (e.g., a dental product or an orthodontic product) may have an elongation at break within a range defined by any two of the preceding values. The oral product (e.g., a dental product or an orthodontic product) may have elongation at break from 1% to 10,000%. The elongation at break may be from 1% to 1,000%. The elongation at break may be from 2% to 500%.

The oral product (e.g., a dental product or an orthodontic product) may have a strain at break of at least 1%, 5%, 50%, 100%, 200%, 300%, 400%, 500%, 1,000%, 2,000%, 3,000%, 4,000%, 5,000%, 6,000%, 7,000%, 8,000%, 9,000%, 10,000%, or more. The oral product (e.g., a dental product or an orthodontic product) may have a strain at break of at most 10,000%, 9,000%, 8,000%, 7,000%, 6,000%, 5,000%, 4,000%, 3,000%, 2,000%, 1,000%, 500%, 400%, 300%, 200% 100%, 50%, 5%, 1%, or less. The oral product (e.g., a dental product or an orthodontic product) may have a strain at break within a range defined by any two of the preceding values. The oral product (e.g., a dental product or an orthodontic product) may have a strain at break from 1% to 10,000%. The strain at break may be from 1% to 1,000%.

The oral product (e.g., a dental product or an orthodontic product) may have a tear strength of at least about 1 kiloNewton per meter (kN/m), 10 kN/m, 50 kN/m, 100 kN/m, 200, kN/m, 300 kN/m, 400 kN/m, 500 kN/m, 600 kN/m, 700 kN/m, 800 kN/m, 900 kN/m, 1,000 kN/m, or more. The dental product or orthodontic product may have a tear strength of at most about 1,000 kN/m, 900 kN/m, 800 kN/m, 700 kN/m, 600 kN/m, 500 kN/m, 400 kN/m, 300 kN/m, 200 kN/m, 100 kN/m, 50 kN/m, 10 kN/m, 1 kN/m, or less. The oral product (e.g., a dental product or an orthodontic product) may have a tear strength within a range defined by any two of the preceding values. The dental product or orthodontic product may have a tear strength from 1 kN/m to 1,000 kN/m.

The oral product (e.g., a dental product or an orthodontic product) may have a hardness from Shore 00 of 10 to Shore D of 100. The oral product (e.g., a dental product or an orthodontic product) may have a hardness from Shore A of 10 to Shore D of 100. The oral product (e.g., a dental product or an orthodontic product) may have a hardness within a range defined between Shore A of 10 to Shore D of 100.

The oral product (e.g., a dental product or an orthodontic product) may absorb water (e.g., at 24 hours). The oral product (e.g., a dental product or an orthodontic product) may have a water absorption (e.g., at 24 hours) of at least 0.1 parts per billion (ppb), 1 ppb, 2 ppb, 5 ppb, 10 ppb, 1 wt %, 10 wt %, 20 wt %, 30%, 40 wt %, or more. The oral product (e.g., a dental product or an orthodontic product) may have a water absorption (e.g., at 24 hours) of at most 50 wt %, 40 wt %, 30 wt %, 20 wt %, 10 wt %, 1 wt %, 10 ppb, 5 ppb, 2 ppb, 1 pbb or less. The oral product (e.g., a dental product or an orthodontic product) may have a water absorption (e.g., at 24 hours) within a range defined by any two of the preceding values. The oral product (e.g., a dental product or an orthodontic product) may have a water absorption (e.g., at 24 hours) from about 0.1 ppb to 50 wt %.

The oral product (e.g., a dental product or an orthodontic product) may be smooth, rough, slippery, sticky, tacky, or any combination thereof. The texture may be modified digitally, mechanically, physically, chemically, or any combination thereof (e.g., using techniques, such as, for example, anti-aliasing, polishing, coating, painting, annealing, sanding, digital texturing, or any combination thereof.

The oral product (e.g., a dental product or an orthodontic product) may be colorless, clear, tinted, opaque, colored (e.g., black, white, orange, yellow, amber, or grey), or any combination thereof.

The oral product (e.g., a dental product or an orthodontic product) may be chemically resistant.

The oral product (e.g., a dental product or an orthodontic product) may be non-toxic. The oral product (e.g., a dental product or an orthodontic product) may be safe for human use. The oral product (e.g., a dental product or an orthodontic product) may be 10993-5 Grade 0.

oral product (e.g., a dental product or an orthodontic product) provided herein can have properties that are significantly improved compared to acid- and radical-based polymers (e.g., see FIG. 3, FIG. 5A, FIG. 5B, FIG. 5C, FIG. 6A, FIG. 6B, FIG. 6C, FIG. 7A, FIG. 7B). An oral product (e.g., a dental product or an orthodontic product) provided herein can have thermomechanical properties which are significantly improved over polymers (e.g., acid- and radical-based photopolymers) produced using other 3D printing methods (e.g., stereolithography and related processes).

Compositions:

Provided in certain embodiments herein is a composition for generating an oral product (e.g., a dental product or an orthodontic product), comprising (i) a latent ruthenium (Ru) complex; (ii) an initiator that is configured to undergo activation upon exposure of the composition to electromagnetic radiation to yield an activated initiator that reacts with the latent Ru complex to yield an activated Ru complex; (iii) a sensitizer that is configured to sensitize the initiator; and (iv) at least one polymer precursor that is configured to react with the activated Ru complex to yield at least a portion of the oral product (e.g., a dental product or an orthodontic product).

In certain aspects, provided herein is a composition for polymerizing a polymer precursor to produce an oral product (e.g., a dental product or an orthodontic product), the composition comprising (i) a latent ruthenium (Ru) complex; (ii) a photo-initiator configured to, upon receiving an electromagnetic radiation, react with said latent Ru complex to yield an activated Ru complex configured to polymerize said polymer precursor; and (iii) a sensitizer that aids in sensitizing said initiator in said composition, thereby producing the oral product (e.g., a dental product or an orthodontic product).

In certain aspects, provided herein is a mixture for use in a system for making an oral product (e.g., a dental product or an orthodontic product), the mixture comprising (i) a polymerizable component including one or more monomers that comprise at least one olefin; (ii) a ruthenium (Ru) complex; and (iii) an initiator that is activatable upon exposure to electromagnetic radiation, wherein the initiator is a photoacid or a photoacid generator. The mixture may be configured to solidify to a green part upon exposure to electromagnetic radiation from a source of the system for making the oral product (e.g., a dental product or an orthodontic product).

The mixture provided herein may be activated at a wavelength from 100-1000 nanometers (nm) (e.g., 350 nm to 465 nm) at a temperature from −30° C. to 300° C. (e.g., 20° C. to 50° C.) for 1 nanosecond (ns) to 1 week (e.g., 1 millisecond (ms) to 1 hour).

The mixture provided herein may have a viscosity of at least 1 centipoise (cP), 50 cP, 100 cP, 500 cP, 1,000 cP, 5,000 cP, 10,000 cP, 50,000 cP, 100,000 cP, 500,000 cP, or more. The mixture provided herein may have a viscosity of at most 500,000 centipoise (cP), 100,000 cP, 50,000 cP, 10,000 cP, 5,000 cP, 1,000 cP, 500 cP, 100 cP, 50 cP, 1 cP, or less. The mixture provided herein may have a viscosity within a range defined by any two of the preceding values. The mixture provided herein may have a viscosity from 1 cP to 500,000 cP. The mixture provided herein may have a viscosity from 2 cP to 10,000 cP.

The photosensitive, polymerizable compositions provided herein may be dissolved or admixed within polymerizable material matrix. Such matrices can include polymers, polymer precursors, or a combination thereof. The matrix may contain at least one olefinic (alkene) or one acetylenic (alkyne) bond per molecule, oligomeric unit, or polymeric unit. Such compositions may include crosslinking polymers. The mixture of polymerized and non-polymerized materials may result from the incomplete polymerization of the polymer precursor. The polymerized and non-polymerized materials may be chemically unrelated.

Catalyst:

The catalyst may be a latent catalyst. The catalyst may be a ruthenium (Ru) catalyst or a Ru complex. The Ru complex may be a latent Ru complex. The latent Ru complex can be a Grubb's catalyst or a Grubb's-type catalyst. The Grubb's catalyst may be a first-generation catalyst, a second-generation catalyst, a Hoveyda-Grubb's catalyst, or a third-generation Grubb's catalyst (e.g., see FIG. 1, FIG. 4A, FIG. 4B, FIG. 4C, and FIG. 4D). The Grubb's-type catalyst may comprise at least one N-heterocyclic carbene (NHC) ligand. The Ru complex may be a 16-electron species.

The latent Ru complex may be a compound selected from the group consisting of:

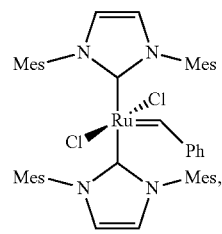

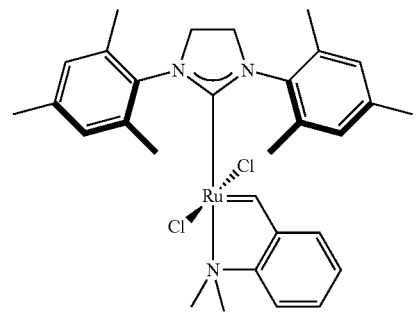

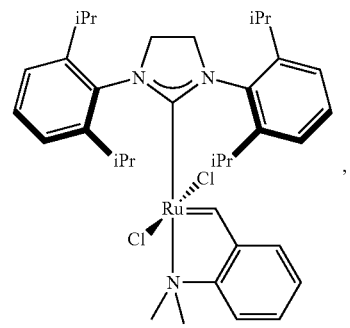

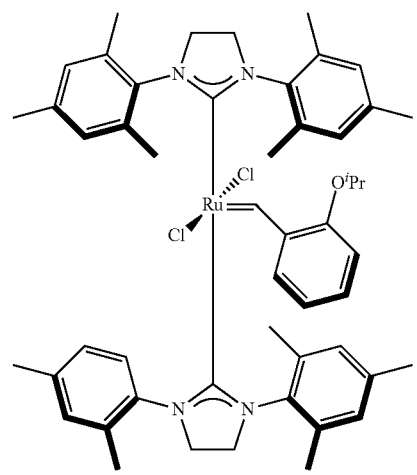

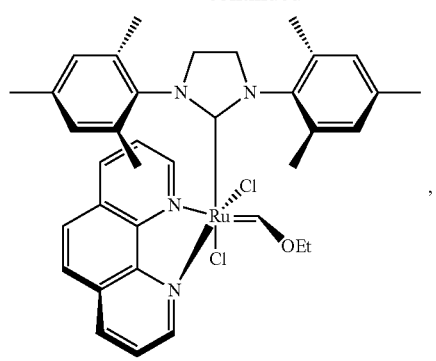
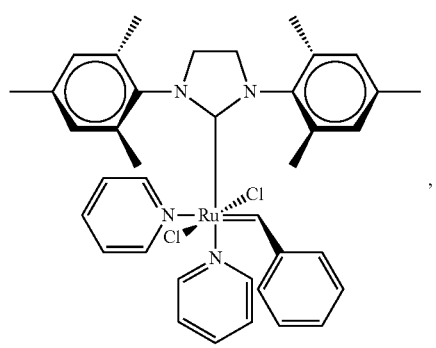
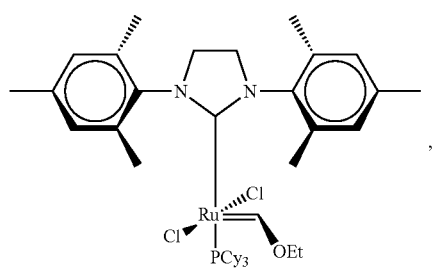
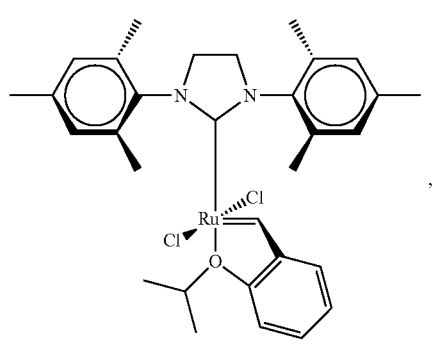
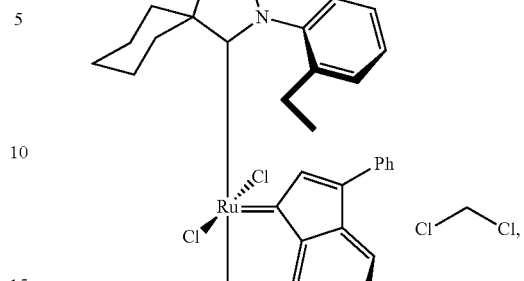
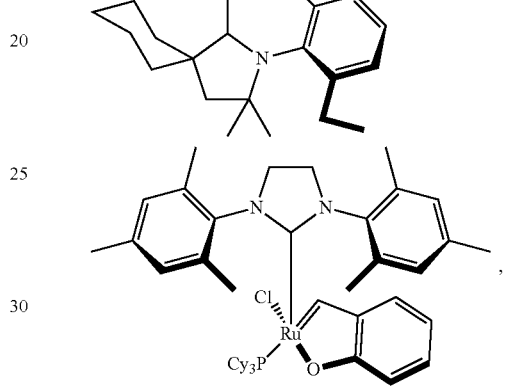
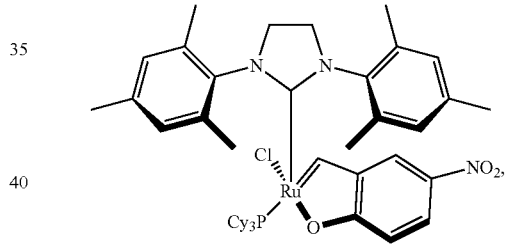
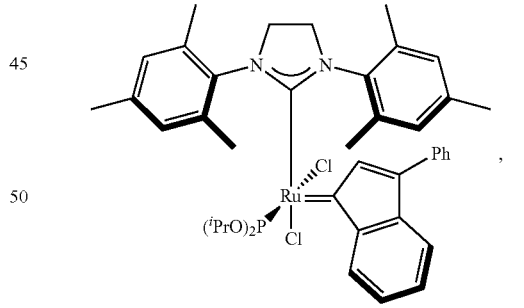
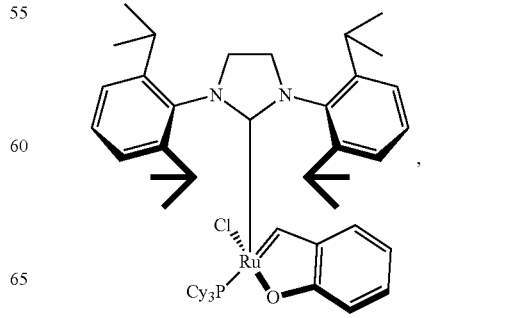

-continued
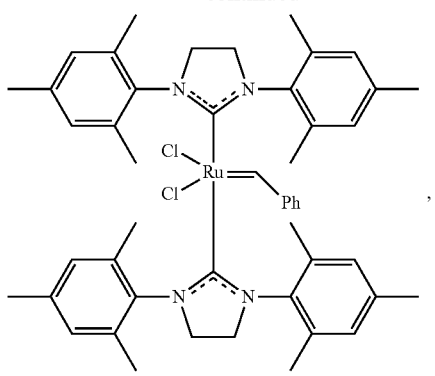
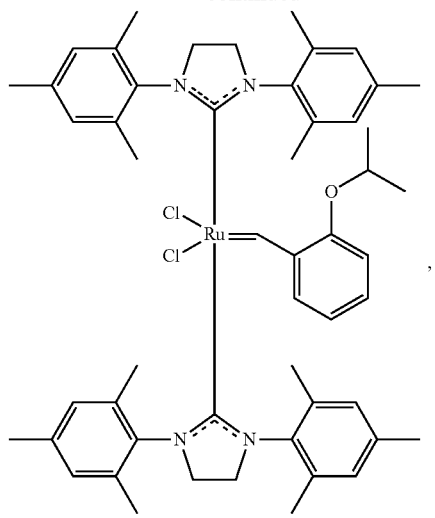
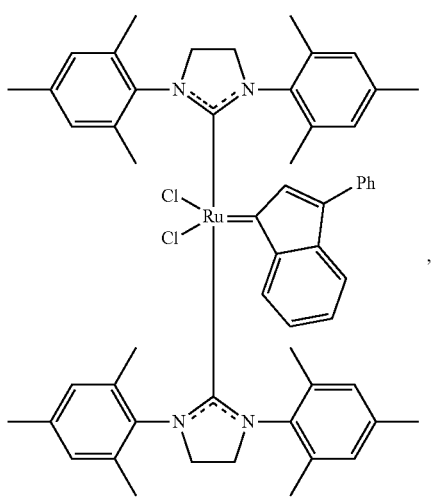
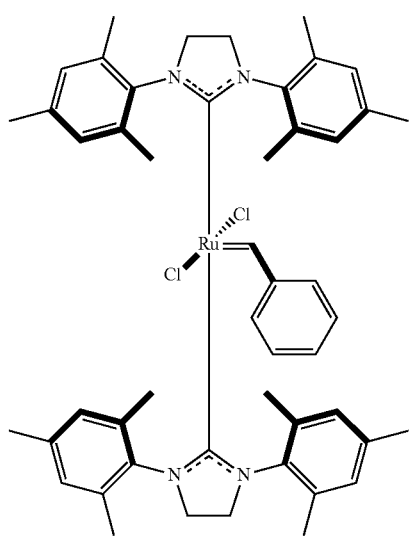
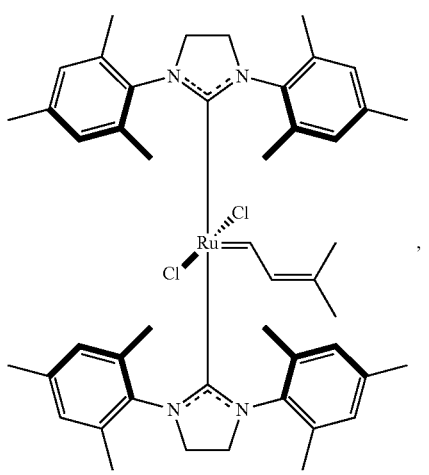
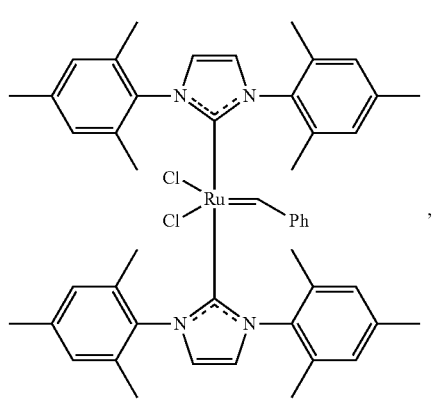

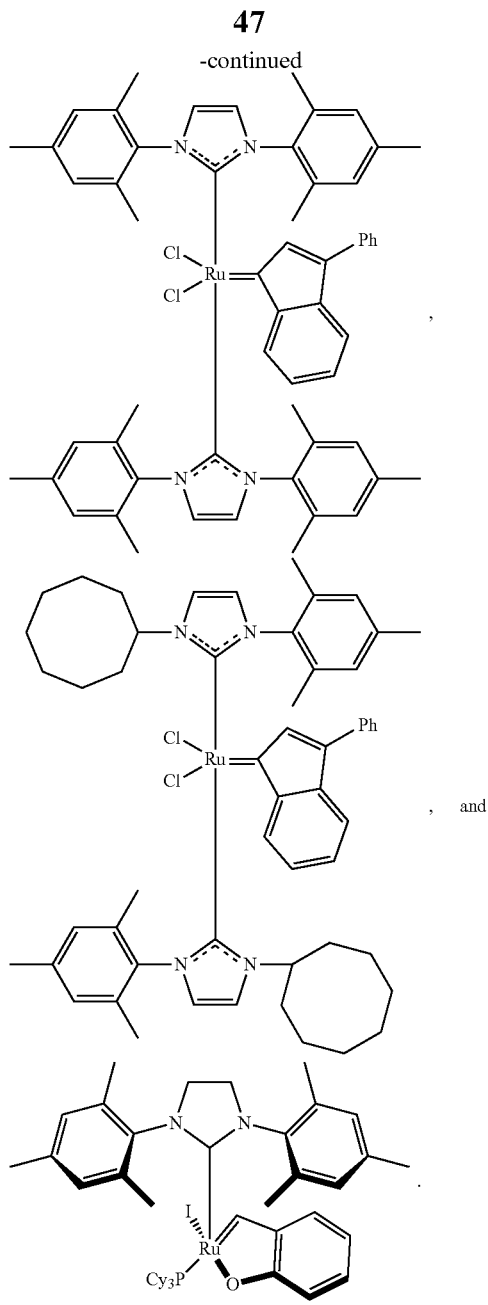
The latent Ru complex may be a compound selected from the group consisting of:
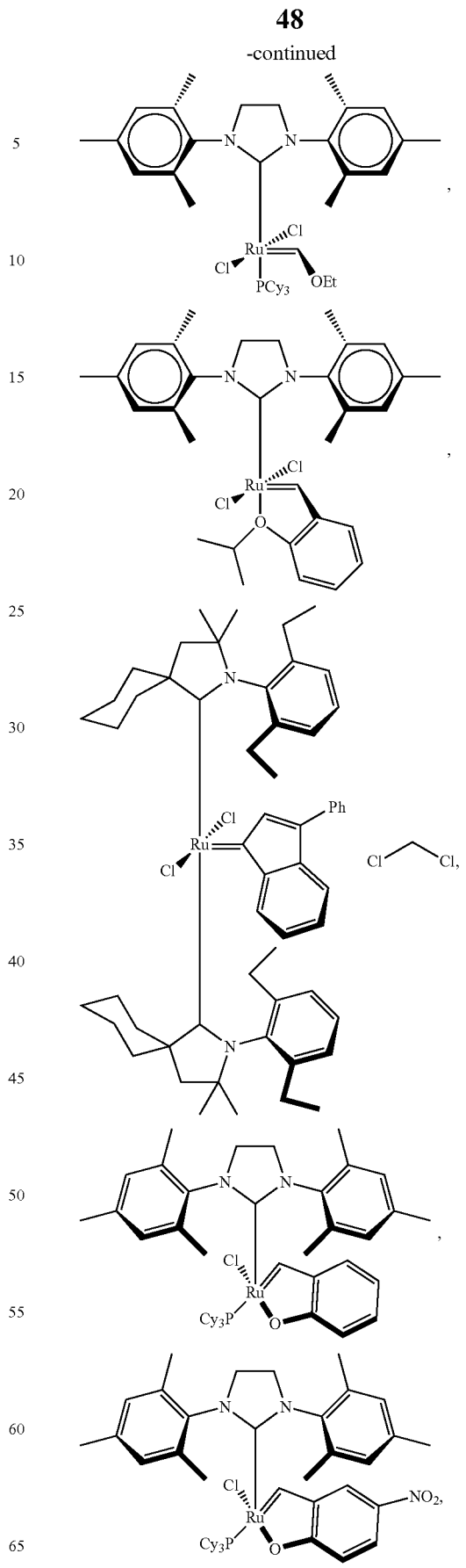

-continued
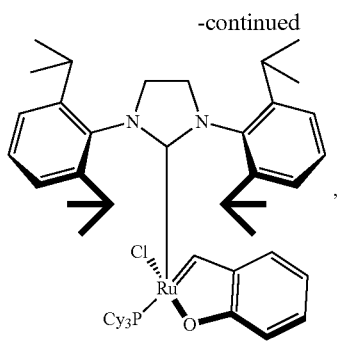
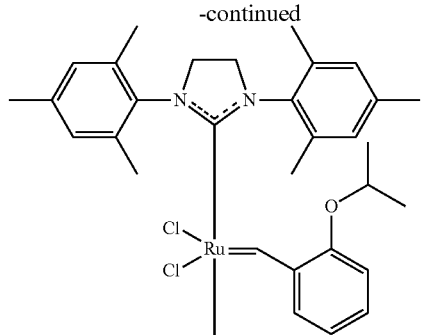
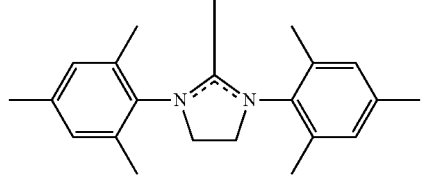
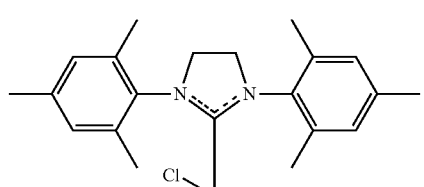
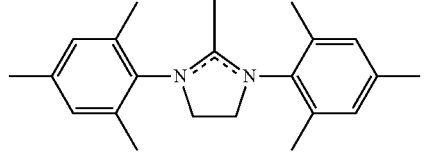
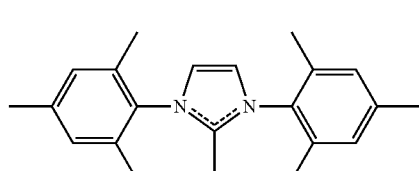
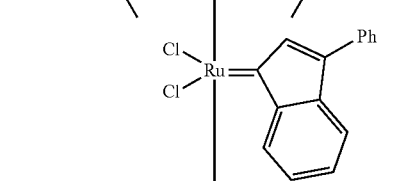
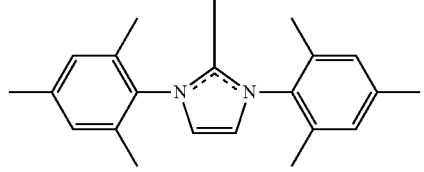

-continued

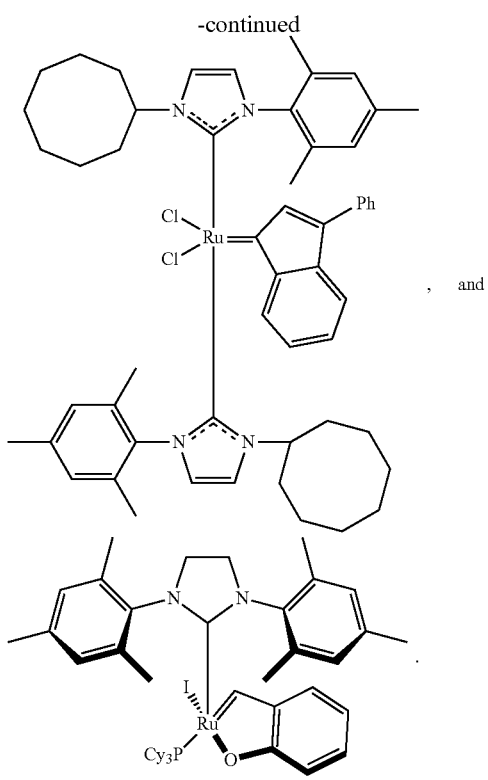

, and

In some embodiments, a mixture described herein comprises any catalyst described in any of International Publication Number WO 2014/055720, U.S. Pat. No. 9,207,532, European Patent Number 2,903,996, International Publication Number WO 2015/065649, U.S. Patent Publication Number 2015/118188, European Patent Publication Number 3,063,592, International Publication Number WO 2018/045132, U.S. Patent Publication Number 2018/067393, U.S. Patent Publication Number 2020/183276, European Patent Publication Number 3,507,007, International Publication Number WO 2020/006345, Photolithographic Olefin Metathesis Polymerization, J. Am. Chem. Soc. 2013, 135, 16817-16820, Visible-Light-Controlled Ruthenium-Catalyzed Olefin Metathesis, J. Am. Chem. Soc. 2019, 141, 17, 6791-6796, A Tandem Approach to Photoactivated Olefin Metathesis: Combining a Photoacid Generator with an Acid Activated Catalyst, J. Am. Chem. Soc. 2009, 131, 6, 2038-2039, Metal-Free Ring-Opening Metathesis Polymerization, J. Am. Chem. Soc. 2015, 137, 1400-1403, JOURNAL OF POLYMER SCIENCE, PART A: POLYMER CHEMISTRY 2019, 57, 1791-17, each of which is incorporated herein by reference, in their entirety, in particular for the compounds provided therein.

The catalyst (e.g., latent Ru complex) can be present (e.g., combined) in a mixture provided herein at a concentration of at least 0.1 parts per million (ppm) (e.g., 0.00001% by weight), 1 ppm (e.g., 0.0001% by weight), 10 ppm (e.g., 0.001% by weight), 100 ppm (e.g., 0.01% by weight), 1,000 ppm (e.g., 0.1% by weight), 10,000 ppm (e.g., 1% by weight), or more. The catalyst (e.g., latent Ru complex) can be present (e.g., combined) in a mixture provided herein at a concentration of at most 10,000 ppm (e.g., 1% by weight), 1,000 ppm (e.g., 0.1% by weight), 100 ppm (e.g., 0.01% by weight), 10 ppm (e.g., 0.001% by weight), 1 ppm (e.g., 0.0001% by weight), 0.1 ppm (e.g., 0.00001% by weight), or less. The catalyst (e.g., latent Ru complex) can be present (e.g., combined) in a mixture provided herein at a concentration within a range defined by any two of the preceding values. The catalyst (e.g., latent Ru complex) can be present (e.g., combined) in a mixture provided herein at a concentration from about 0.1 ppm (e.g., 0.00001% by weight) to about 10,000 ppm (e.g., 1% by weight). The catalyst (e.g., latent Ru complex) can be present (e.g., combined) in a mixture provided herein at a concentration from about 1 ppm (e.g., 0.00001% by weight) to about 10,000 ppm (e.g., 1% by weight).

The catalyst (e.g., latent Ru complex) and the initiator can be present (e.g., combined) in a mixture provided herein at a ratio of the Ru complex to the initiator at a ratio by moles of at least 0.01:1.0, 0.025:1.0, 0.05:1.0, 0.075:1.0, 0.1:1.0, 0.5:1.0, 1.0:1.0, 1.5:1.0, 2.0:1.0, 3.0:1.0, 4.0:1.0, 5.0:1.0, 6.0:1.0, 7.0:1.0, 8.0:1.0, 9.0:1.0, 10:1.0, or more of the Ru complex. The catalyst (e.g., latent Ru complex) and the initiator can be present (e.g., combined) in a mixture provided herein at a ratio of the Ru complex to the initiator at a ratio by moles of at most 10:1.0, 9.0:1.0, 8.0:1.0, 7.0:1.0, 6.0:1.0, 5.0:1.0, 6.0:1.0, 4.0:1.0, 3.0:1.0, 2.0:1.0, 1.0:1.0, 0.5:1.0, 0.1:1.0, 0.075:1.0, 0.05:1.0, 0.025:1.0, 0.01:1.0, or less of the Ru complex. The catalyst (e.g., latent Ru complex) and the initiator can be present (e.g., combined) in a mixture provided herein at a ratio of the Ru complex to the initiator at a ratio by moles within a range defined by any two of the preceding values. The catalyst (e.g., latent Ru complex) and the initiator can be present (e.g., combined) in a mixture provided herein at a ratio of the Ru complex to the initiator at a ratio by moles from 0.01:1.0 to 10:1.0. The latent Ru complex and the initiator may be present in the mixture at a ratio by moles of the Ru complex to the initiator at a ratio by moles from 0.02:1.0 to 1.0:1.0.

The catalyst (e.g., latent Ru complex) and the sensitizer can be present (e.g., combined) in a mixture provided herein at a ratio of the Ru complex to the sensitizer at a ratio by moles of at least 0.001:1.0, 0.01:1.0, 0.025:1.0, 0.05:1.0, 0.075:1.0, 0.1:1.0, 0.5:1.0, 1.0:1.0, 1.5:1.0, 2.0:1.0, 3.0:1.0, 4.0:1.0, 5.0:1.0, 6.0:1.0, 7.0:1.0, 8.0:1.0, 9.0:1.0, 10:1.0, 100:1.0, 1000:1.0, or more of the Ru complex. The catalyst (e.g., latent Ru complex) and the sensitizer can be present (e.g., combined) in a mixture provided herein at a ratio of the Ru complex the sensitizer at a ratio by moles of at most 1000:1.0, 100:1.0, 10:1.0, 9.0:1.0, 8.0:1.0, 7.0:1.0, 6.0:1.0, 5.0:1.0, 6.0:1.0, 4.0:1.0, 3.0:1.0, 2.0:1.0, 1.0:1.0, 0.5:1.0, 0.1:1.0, 0.075:1.0, 0.05:1.0, 0.025:1.0, 0.01:1.0, 0.001:1.0, or less of the Ru complex. The catalyst (e.g., latent Ru complex) and the sensitizer can be present (e.g., combined) in a mixture provided herein at a ratio of the Ru complex to the sensitizer at a ratio by moles within a range defined by any two of the preceding values. The catalyst (e.g., latent Ru complex) and the sensitizer can be present (e.g., combined) in a mixture provided herein at a ratio of the Ru complex to the sensitizer at a ratio by moles from 001:1.0 to 1000:1.0. The latent Ru complex and the sensitizer may be present in the mixture at a ratio by moles of the Ru complex to the sensitizer at a ratio by moles from 0.02:1.0 to 1.0:1.0.

The catalyst (e.g., latent Ru complex) and the polymer precursor may be present (e.g., combined) in a mixture provided herein at a weight ratio of at least 0.1 parts per million (ppm) (e.g., 0.00001% by weight), 1 ppm (e.g., 0.0001% by weight), 10 ppm (e.g., 0.001% by weight), 100 ppm (e.g., 0.01% by weight), 1,000 ppm (e.g., 0.1% by weight), 10,000 ppm (e.g., 1% by weight), or more. The catalyst (e.g., latent Ru complex) and the polymer precursor may be present (e.g., combined) in a mixture provided herein at a weight ratio of at most 10,000 ppm (e.g., 1% by weight), 1,000 ppm (e.g., 0.1% by weight), 100 ppm (e.g., 0.01% by weight), 10 ppm (e.g., 0.001% by weight), 1 ppm (e.g., 0.0001% by weight), 0.1 ppm (e.g., 0.00001% by weight), or less. or more. The catalyst (e.g., latent Ru complex) and the polymer precursor may be present (e.g., combined) in a mixture provided herein at a weight ratio within a range defined by any two of the preceding values. The catalyst (e.g., latent Ru complex) and the polymer precursor may be present (e.g., combined) in a mixture provided herein at a weight ratio of at most 10% (e.g., 10,000 ppm) or less. The catalyst (e.g., latent Ru complex) and the polymer precursor may be present (e.g., combined) in a mixture provided herein at a weight ratio from 0.1 ppm to 10% (e.g., 10,000 ppm).

The catalyst may be an activated catalyst. The catalyst may be a ruthenium (Ru) catalyst or a Ru complex. The Ru complex may be an activated Ru complex. The activated Ru complex may undergo a ring opening metathesis polymerization (ROMP) reaction with said at least one polymer precursor, for example, to generate at least a portion of said polymer. The ROMP reaction may be a photoinitiated ROMP (P-ROMP) or photolithographic olefin metathesis polymerization (PLOMP)).

Initiators:

The initiator can be a photo-initiator. The initiator can be a photoacid generator (PAG) or a photoacid (PAH). The initiator can be a photoacid generator (PAG). The initiator can be a a photoacid (PAH).

The initiator may comprise one or more iodonium ion, a sulfonium ion, a dicarboximide, a thioxanthone, or an oxime. The initiator may comprise an iodonium ion, a sulfonium ion, a dicarboximide, a thioxanthone, or an oxime. The initiator may be an iodonium salt, a sulfonium salt, a dicarboximide, a thioxanthone, or an oxime. The initiator may be an iodonium salt, a sulfonium salt, or a dicarboximide. The initiator may be an iodonium salt. The initiator may be an sulfonium salt. The initiator may be dicarboximide.

The initiator may be a salt. The initiator may be a salt comprising one or more counterion. The initiator may be a sulfonium salt comprising one or more counterion. The initiator may be an iodonium salt comprising one or more counterion. The counter ion may be selected from the group consisting of a sulfate, sulfonate, antimonate, triflate, nonaflate, borate, carboxylate, phosphate, fluoride, chloride, bromide, iodide, antimonide, and boride. The counter ion may be selected from the group consisting of a sulfate, a phosphate, a fluoride, a chloride, a bromide, an iodide, an antimonate, a boride, a carboxide, a triflate, and a nonaflate.

The initiator may be a compound having a structure of Formula (I):

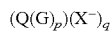

$(Q(G)_p)(X^-)_q$        Formula (I)

wherein:

Q is sulfur (S), $S^+$, or iodine ($I^+$);

each G is independently optionally substituted alkyl, optionally substituted cycloalkyl, optionally substituted heterocycloalkyl, optionally substituted aryl, or optionally substituted heteroaryl;

each X is independently a counter ion;

p is 2 or 3; and q is 1 or 2.

In some embodiments, Q is $S^+$.

In some embodiments, p is 3 and q is 1.

In some embodiments, each G is independently optionally substituted alkyl or optionally substituted aryl. In some embodiments, each G is independently optionally substituted aryl. In some embodiments, each G is independently substituted phenyl. In some embodiments, each G is independently substituted phenyl, wherein each phenyl is independently substituted with one or more substituent, wherein said one or more substituent is independently $C_1$-$C_6$ alkyl. In some embodiments, each G is independently phenyl or $C_1$-$C_6$ alkyl In some embodiments, $C_1$-$C_6$ alkyl is selected from the group consisting of methyl, ethyl, propyl, isopropyl, butyl, tert-butyl, and sec-butyl. In some embodiments, G is phenyl.

In some embodiments, Q is S.

In some embodiments, p is 2 and q is 2.

In some embodiments, each G is independently optionally substituted alkyl or optionally substituted aryl. In some embodiments, each G is independently substituted aryl with one or more substituent, wherein said one or more substituent is further optionally substituted. In some embodiments, one or more substituent is $S^+(G^1)(C)$, wherein $G^1$ and $G^2$ are each independently optionally substituted alkyl or optionally substituted aryl. In some embodiments, $G^1$ and $G^2$ are each phenyl.

In some embodiments, Q is $I^+$.

In some embodiments, p is 2 and q is 1.

In some embodiments, each G is independently optionally substituted heterocycloalkyl, optionally substituted aryl, or optionally substituted heteroaryl.

In some embodiments, each G is independently optionally substituted heterocycloalkyl or optionally substituted aryl. In some embodiments, each G is independently optionally substituted heteroaryl or optionally substituted aryl. In some embodiments, the optionally substituted heterocycloalkyl is a $C_7$-$C_{15}$ heterocycloalkyl. In some embodiments, the optionally substituted heterocycloalkyl is a substituted coumarin. In some embodiments, the substituted coumarin is substituted with one or more substituent, each substituent selected from the group consisting of halogen, $C_1$-$C_6$ alkyl, $C_1$-$C_6$ heteroalkyl, and $C_1$-$C_6$ alkoxy. In some embodiments, the substituted coumarin is substituted with one or more substituent, each substituent selected from the group consisting of $C_1$-$C_6$ alkyl and $C_1$-$C_6$ alkoxy. In some embodiments, the substituted coumarin is substituted with one or more substituent, each substituent selected from the group consisting of methyl, ethyl, propyl, isopropyl, tert-butyl, methoxy, ethoxy, propoxy, isopropoxy, and isobutoxy. In some embodiments, each G is independently substituted phenyl. In some embodiments, each G is phenyl. In some embodiments, each G is independently phenyl or a coumarin substituted with one or more substituent, each substituent selected from the group consisting of methyl, ethyl, propyl, isopropyl, tert-butyl, methoxy, ethoxy, propoxy, isopropoxy, and isobutoxy.

In some embodiments, the optionally substituted aryl is substituted with an optionally substituted dicarboxyimide. In some embodiments, the dicarboxyimide is attached to the optionally substituted aryl via the N atom of the optionally substituted dicarboxyimide. In some embodiments, the dicarboxyimide is substituted with one or more substituent. In some embodiments, the dicarboxyimide is a $C_7$-$C_{15}$ heterocycloalkyl. In some embodiments, the $C_7$-$C_{15}$ heterocycloalkyl is substituted with one or more substituent, each substituent selected from the group consisting of halogen, $C_1$-$C_6$ alkyl, $C_1$-$C_6$ heteroalkyl, and $C_1$-$C_6$ alkoxy. In some embodiments, the $C_7$-$C_{15}$ heterocycloalkyl is substituted with a halogen. In some embodiments, each G is independently phenyl or a dicarboxyimide substituted with a halogen.

In some embodiments, each G is independently phenyl or a $C_7$-$C_{15}$ heterocycloalkyl is substituted with one or more substituent, each substituent selected from the group consisting of halogen, $C_1$-$C_6$ alkyl, $C_1$-$C_6$ heteroalkyl, and $C_1$-$C_6$ alkoxy.

In some embodiments, each G is independently optionally substituted aryl. In some embodiments, each G is independently substituted phenyl. In some embodiments, each G is independently substituted phenyl. In some embodiments, each phenyl is independently substituted with one or more substituent. In some embodiments, the one or more substituent is independently $C_1$-$C_{15}$ alkyl. In some embodiments, the one or more substituent is independently $C_1$-$C_6$ alkyl. In some embodiments, each G is phenyl.

In some embodiments, each X is independently selected from the group consisting of a sulfate, sulfonate, antimonate, triflate, nonaflate, borate, carboxylate, phosphate, fluoride, chloride, bromide, iodide, antimonide, and boride.

In some embodiments, each X is independently selected from the group consisting of:

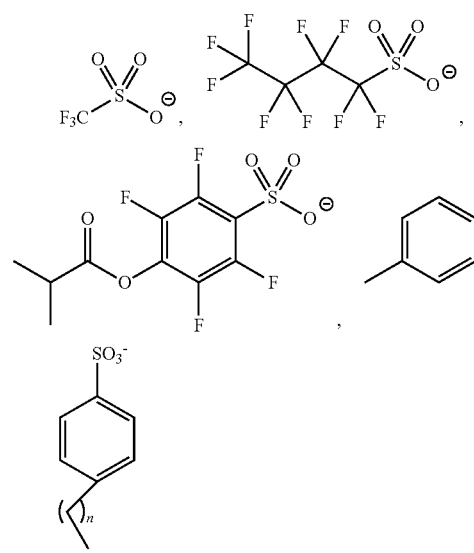

(wherein n is 0-20),

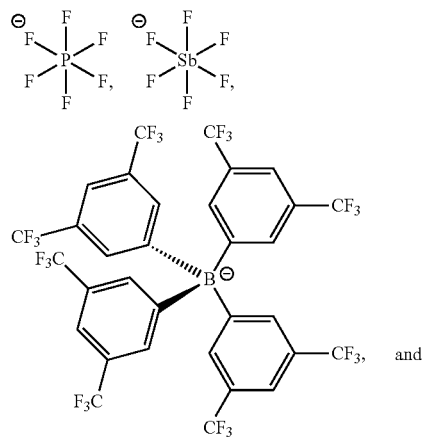

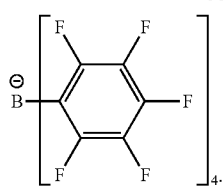

In some embodiments, the initiator is a compound selected from the group consisting of:

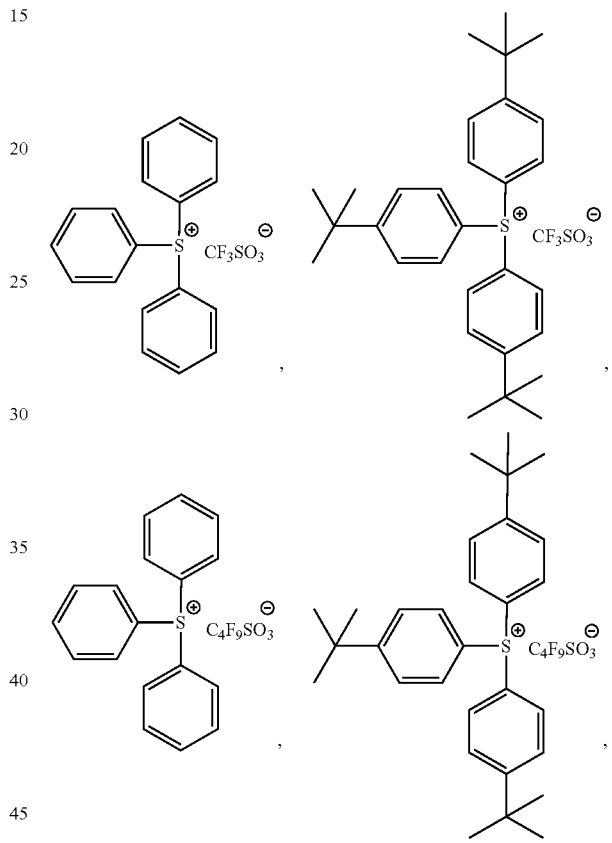

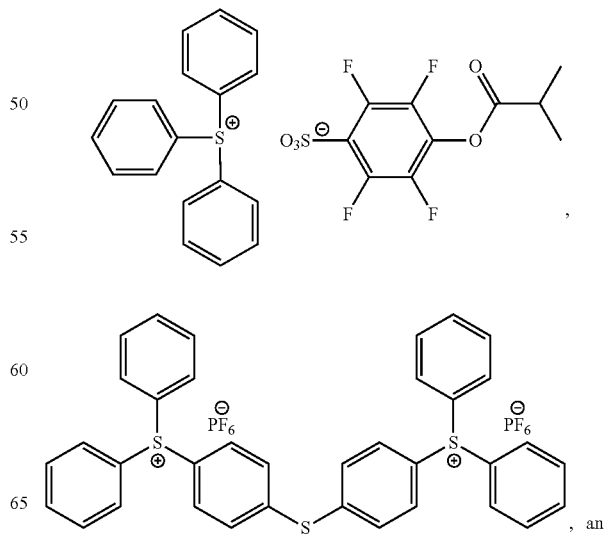

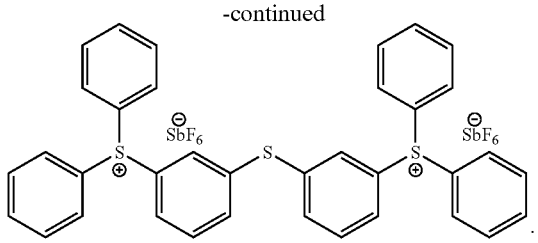

In some embodiments, the initiator is a compound selected from the group consisting of:

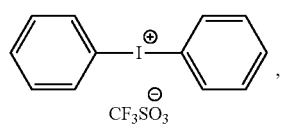

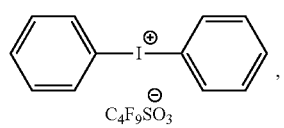

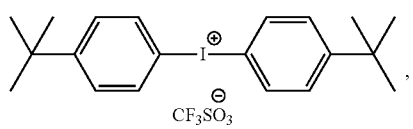

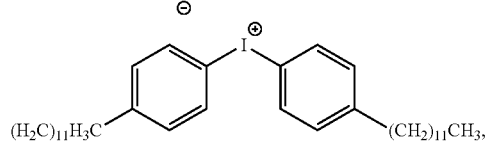

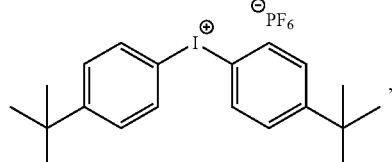

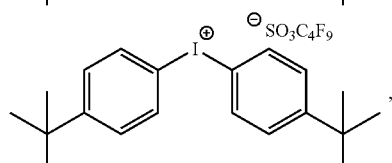

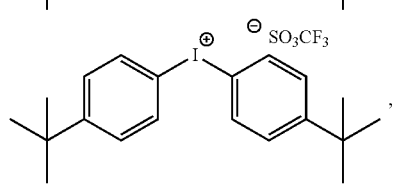

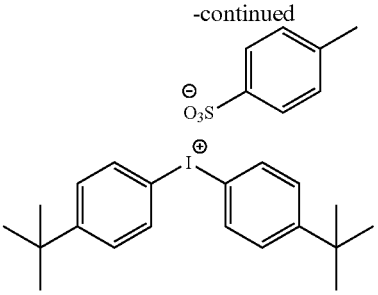

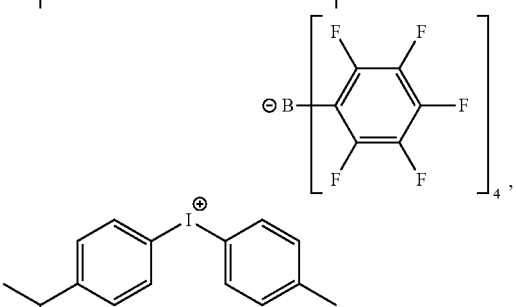

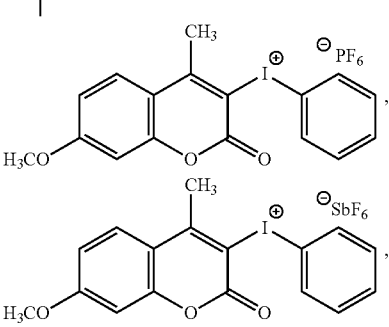

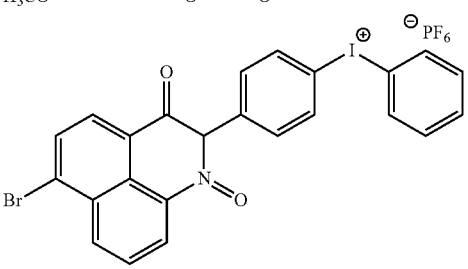

In some embodiments, the initiator is a substituted dicarboxyimide. In some embodiments, the initiator comprises one or more substituted dicarboxyimides. In some embodiments, the initiator comprises two substituted dicarboxyimides. In some embodiments, the two dicarboxyimides are commonly coupled to an optionally substituted phenyl.

In some embodiments, the dicarboxyamide is a $C_7$-$C_{15}$ heterocycloalkyl. In some embodiments, the substituted dicarboxyimide is substituted (e.g., N-substituted) with one or more substituted sulfonate. In some embodiments, the one or more substituted sulfonate is substituted with optionally substituted phenyl or $C_1$-$C_6$ haloalkyl. In some embodiments, the one or more substituted sulfonate is substituted with phenyl substituted with one or more substituent, each substituent independently selected from the group consisting of $C_1$-$C_6$ alkyl and $C_1$-$C_6$ fluoroalkyl. In some embodiments, the one or more substituted sulfonate is substituted with toluenyl. In some embodiments, the $C_1$-$C_6$ haloalkyl is a $C_1$-$C_6$ fluoroalkyl. In some embodiments, the $C_1$-$C_6$ fluoroalkyl is —$CF_3$ or —$C_4F_9$.

In some embodiments, the substituted dicarboxyimide is selected from the group consisting of a substituted 3a,4,7,7a-tetrahydro-1H-4,7-methanoisoindole-1,3(2H)-dione, a substituted 1H-benzo[de]isoquinoline-1,3(2H)-dione, and a thiochromeno[2,3-e]isoindole-1,3,6(2H)-trione.

In some embodiments, the initiator is a compound selected from the group consisting of:

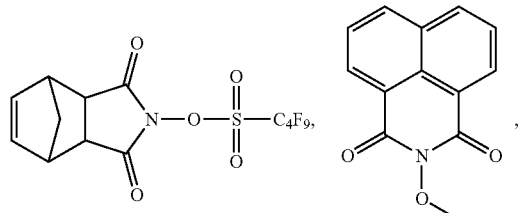

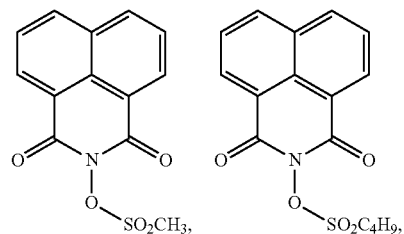

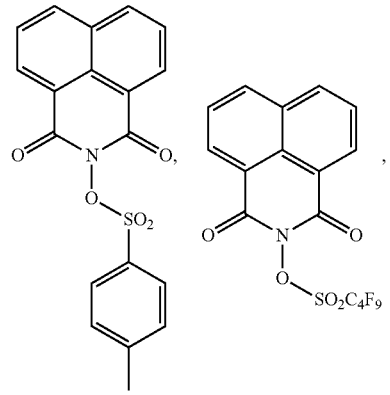

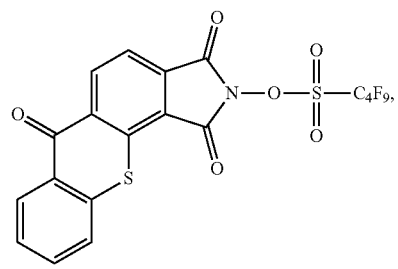

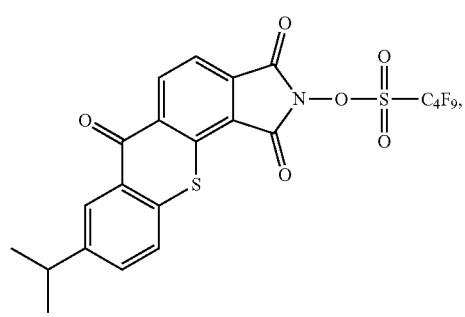

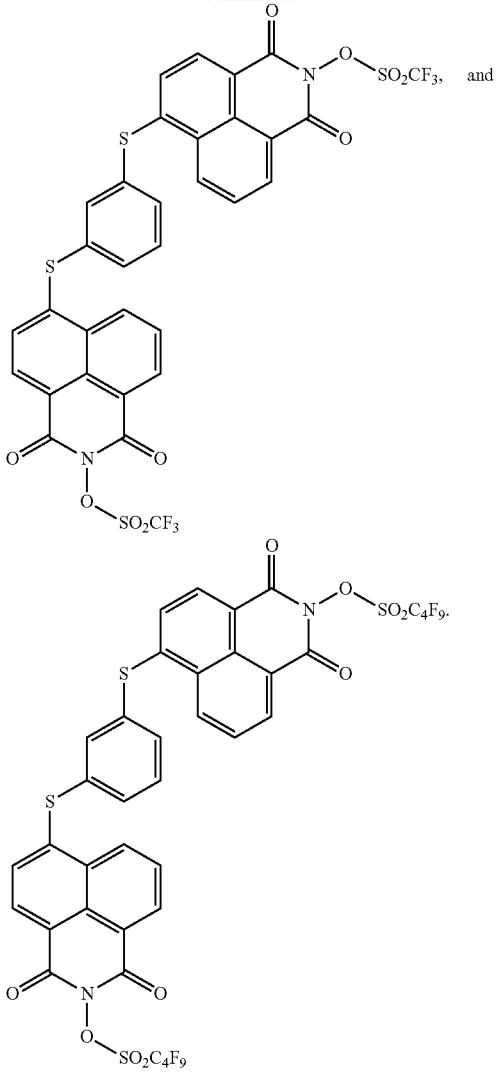

In some embodiments, the initiator is a substituted thioxanthone. In some embodiments, the substituted thioxanthone is a $C_7$-$C_{15}$ heterocycloalkyl. In some embodiments, the substituted thioxanthone is substituted with one or more substituted sulfonate. In some embodiments, the one or more substituted sulfonate is substituted with optionally substituted phenyl or $C_1$-$C_6$ haloalkyl. In some embodiments, the one or more substituted sulfonate is substituted with phenyl substituted with one or more substituent, each substituent independently selected from the group consisting of $C_1$-$C_6$ alkyl and $C_1$-$C_6$ fluoroalkyl. In some embodiments, the one or more substituted sulfonate is substituted with toluenyl. In some embodiments, the $C_1$-$C_6$ haloalkyl is a $C_1$-$C_6$ fluoroalkyl. In some embodiments, the $C_1$-$C_6$ fluoroalkyl is —$CF_3$, —$C_4F_9$, or —$C_8F_{17}$.

In some embodiments, the initiator is a substituted oxime. In some embodiments, the substituted oxime is a $C_7$-$C_{15}$ heteroaryl. In some embodiments, the substituted oxime is substituted with one or more substituted sulfonate. In some embodiments, the one or more substituted sulfonate is substituted with optionally substituted phenyl or $C_1$-$C_6$ haloalkyl. In some embodiments, the one or more substituted sulfonate is substituted with phenyl substituted with one or more substituent, each substituent independently selected from the group consisting of halogen, $C_1$-$C_6$ alkyl, and $C_1$-$C_6$ fluoroalkyl. In some embodiments, the one or more substituted sulfonate is substituted with toluenyl. In some embodiments, the $C_1$-$C_6$ haloalkyl is a $C_1$-$C_6$ fluoroalkyl. In some embodiments, the $C_1$-$C_6$ fluoroalkyl is —$CF_3$, —$C_4F_9$, or —$C_8F_{17}$.

In some embodiments, the substituted oxime is selected from the group consisting of an optionally substituted fluoren-9-one oxime, an optionally substituted thioxanthen-9-one oxime, and an optionally substituted thiophenylidene.

In some embodiments, the initiator is a compound selected from the group consisting of:

Metathesis Polymerization, *J. Am. Chem. Soc.* 2013, 135, 16817-16820, Visible-Light-Controlled Ruthenium-Catalyzed Olefin Metathesis, *J. Am. Chem. Soc.* 2019, 141, 17, 6791-6796, A Tandem Approach to Photoactivated Olefin Metathesis: Combining a Photoacid Generator with an Acid Activated Catalyst, *J. Am. Chem. Soc.* 2009, 131, 6, 2038-2039, Metal-Free Ring-Opening Metathesis Polymerization, *J. Am. Chem. Soc.* 2015, 137, 1400-1403, JOURNAL OF POLYMER SCIENCE, PART A: POLYMER CHEMISTRY 2019, 57, 1791-17, each of which is incorporated herein by reference, in their entirety, in particular for the compounds provided therein.

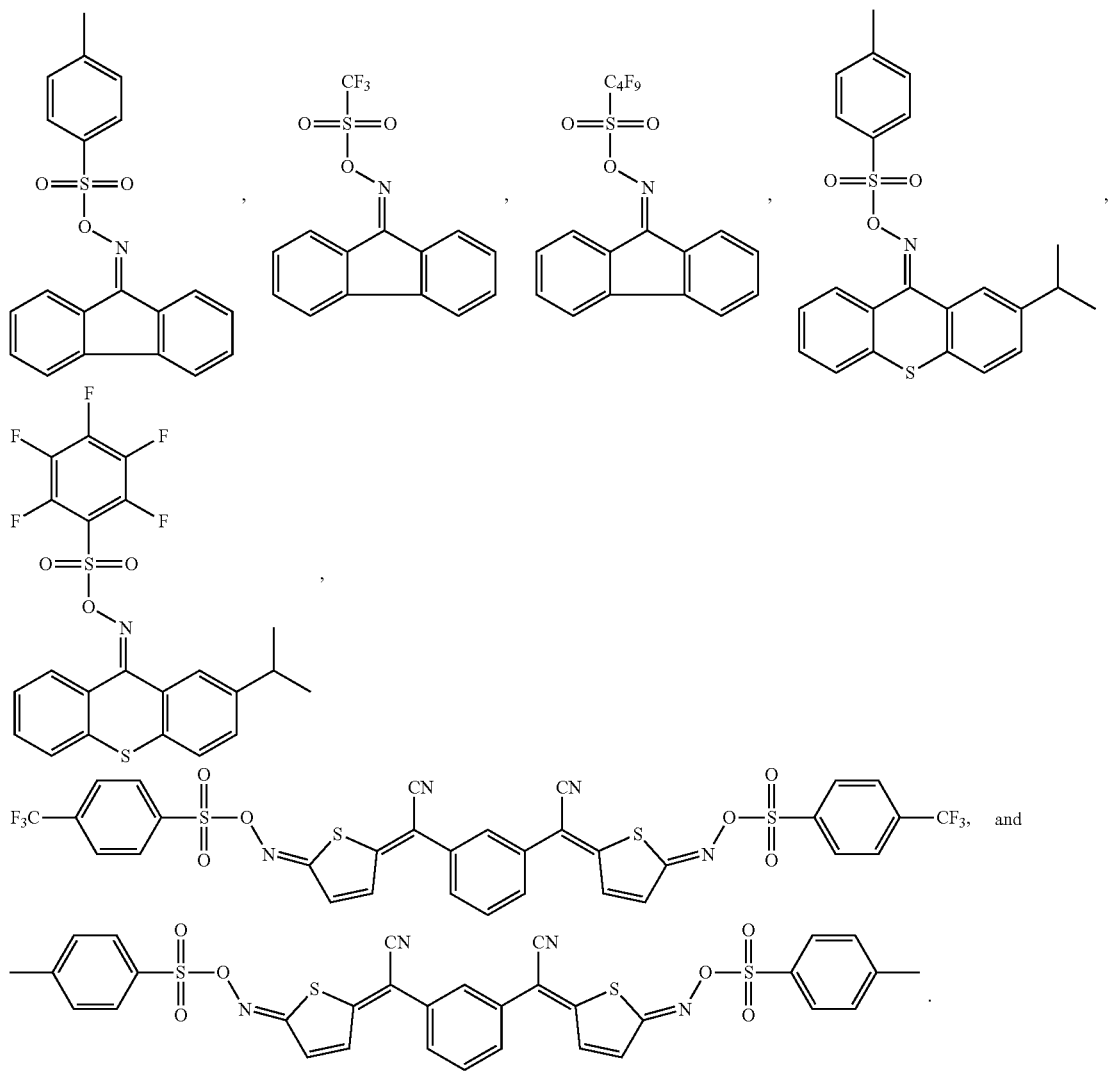

In some embodiments, a mixture described herein comprises any initiator described in any of International Publication Number WO 2014/055720, U.S. Pat. No. 9,207,532, European Patent Number 2,903,996, International Publication Number WO 2015/065649, U.S. Patent Publication Number 2015/118188, European Patent Publication Number 3,063,592, International Publication Number WO 2018/045132, U.S. Patent Publication Number 2018/067393, U.S. Patent Publication Number 2020/183276, European Patent Publication Number 3,507,007, International Publication Number WO 2020/006345, Photolithographic Olefin The initiator can be present (e.g., combined) in a mixture provided herein at a concentration of at least 0.1 parts per million (ppm) (e.g., 0.00001% by weight), 1 ppm (e.g., 0.0001% by weight), 10 ppm (e.g., 0.001% by weight), 100 ppm (e.g., 0.01% by weight), 1,000 ppm (e.g., 0.1% by weight), 10,000 ppm (e.g., 1% by weight), 100,000 ppm (e.g., 10% by weight), or more. The initiator can be present (e.g., combined) in a mixture provided herein at a concentration of at most 100,000 ppm (e.g., 10% by weight), 10,000 ppm (e.g., 1% by weight), 1,000 ppm (e.g., 0.1% by weight), 100 ppm (e.g., 0.01% by weight), 10 ppm (e.g., 0.001% by weight), 1 ppm (e.g., 0.0001% by weight), 0.1 ppm (e.g., 0.00001% by weight), or less. The initiator can be present (e.g., combined) in a mixture provided herein at a concentration within a range defined by any two of the preceding values. The initiator can be present (e.g., combined) in a mixture provided herein at a concentration from about 0.1 ppm (e.g., 0.00001% by weight) to about 100,000 ppm (e.g., 10% by weight). The initiator may be present in the mixture at a concentration from about 1 ppm (e.g., 0.0001% by weight) to about 50,000 ppm (e.g., 5% by weight).

The initiator and the sensitizer can be present (e.g., combined) in a mixture provided herein at a molar ratio of at least 1:1000, 1:500, 1:100, 1:50, 1:40, 1:30, 1:20, 1:10, 1:5, 1:1, 5:1, 10:1, 20:1, 30:1, 40:1, 50:1, 100:1, 500:1, 1000:1, or more of the initiator to the sensitizer. The initiator and the sensitizer can be present (e.g., combined) in a mixture provided herein at a molar ratio of at most 1000:1, 500:1, 100:1, 50:1, 40:1, 30:1, 20:1, 10:1, 5:1, 1:1, 1:5, 1:10, 1:20, 1:30, 1:40, 1:50, 1:100, 1:500, 1:1000, or less of the initiator to the sensitizer. The initiator and the sensitizer can be present (e.g., combined) in a mixture provided herein at a molar ratio within a range defined by any two of the preceding values. The initiator and the sensitizer can be present (e.g., combined) in a mixture provided herein at a molar ratio from 1000:1 initiator to sensitizer to 1:1000 initiator to sensitizer. The initiator and the sensitizer can be present (e.g., combined) in a mixture provided herein at a molar ratio from 10:1 initiator to sensitizer to 1:10 initiator to sensitizer.

The initiator and the polymer precursor can be present (e.g., combined) in a mixture provided herein at a molar ratio of at least 1:10,000,000, 1:1,000,000, 1:500,000, 1:100,000, 1:50,000, 1:10,000, 1:5,000, 1:1,000, 1:500, 1:100, 1:50, 1:30, 1:20, 1:10, 1:1, or more of the initiator to the polymer precursor. The initiator and the polymer precursor can be present (e.g., combined) in a mixture provided herein at a molar ratio of at most 1:1, 1:10, 1:20, 1:30, 1:50, 1:100, 1:500, 1:1,000, 1:5,000, 1:10,000, 1:50,000, 1:100,000, 1:500,000, 1:1,000,000, 1:10,000,000, or less of the initiator to the polymer precursor. The initiator and the polymer precursor can be present (e.g., combined) in a mixture provided herein at a molar ratio within a range defined by any two of the preceding values. The initiator and the polymer precursor can be present (e.g., combined) in a mixture provided herein at a molar ratio from 1:1 initiator to the polymer precursor to 1:10,000,000 initiator to the polymer precursor. The initiator and the polymer precursor can be present (e.g., combined) in a mixture provided herein at a molar ratio from 1:20 initiator to polymer precursor to 1:100,000 initiator to the polymer precursor.

Sensitizers:

The sensitizer may be configured to transfer or disperse the energy of electromagnetic radiation. The sensitizer may stabilize or sensitize the initiator. In some embodiments, the sensitizer is configured to scatter electromagnetic radiation, thereby sensitizing the initiator. In some embodiments, the sensitizer is configured to scatter ambient electromagnetic radiation, thereby sensitizing the initiator. In some embodiments, the sensitizer is configured to scatter electromagnetic radiation having a wavelength from 200 to 2000 nanometers, thereby sensitizing the initiator. The sensitizer may be configured to disperse, transfer, or convert the energy of electromagnetic radiation such that the initiator is activated at a particular wavelength range, such as, for example, from about 350 nanometers (nm) to about 465 nm.

The electromagnetic radiation may have a wavelength of at least 1 nanometer (nm) 10 nm, 50 nm, 100 nm, 500 nm, 1,000 nm, 2,000 nm, 3,000 nm, 4,000 nm, 5,000 nm, 10,000 nm, 15,000 nm, 25,000 nm, 50,000 nm, 75,000 nm, 100,000 nm, 200,000 nm, 300,000 nm, 400,000 nm, 500,000 nm, 600,000 nm, 700,000 nm, 800,000 nm, 900,000 nm, 1,000,000 nm, 2,000,000 nm, 3,000,000 nm, 4,000,000 nm, 5,000,000 nm, 10,000,000 nm, or more. The electromagnetic radiation may have a wavelength of at most 10,000,000 nm, 5,000,000 nm, 4,000,000 nm, 3,000,000 nm, 2,000,000 nm, 1,000,000 nm, 900,000 nm, 800,000 nm, 700,000 nm, 600,000 nm, 500,000 nm, 400,000 nm, 300,000 nm, 200,000 nm, 100,000 nm, 75,000 nm, 50,000 nm, 25,000 nm, 15,000 nm, 10,000 nm, 5,000 nm, 4,000 nm, 3,000 nm, 2,000 nm, 1,000 nm, 500 nm, 100 nm, 50 nm, 10 nm, 1 nm, or less. The electromagnetic radiation may have a wavelength within a range defined by any two of the preceding values. The electromagnetic radiation may have a wavelength from 300 nm to 3,000 nm. The electromagnetic radiation may have a wavelength from about 350 nm to about 465 nm.

The sensitizer may be a conjugated aromatic molecule (e.g. a naphthalene, an anthracene, a perylene, or an acene), a phenothiazine (e.g., or a derivative thereof), a thioxanthone (e.g., or a derivative thereof), a camphorquinone, an aminoketone, a benzophenone, a metal complex (e.g., Titanium), an aminobenzoate, a coumarin (e.g., a derivative thereof), an indoline, a porphyrin, a rhodamine, a pyrylium, a phenazine, a phenoxazine, an alpha hydroxy ketone, or a phosphine oxide. The sensitizer may be a conjugated aromatic molecule (e.g. a naphthalene, a perylene, or an acene), a phenothiazine (e.g., or a derivative thereof), a thioxanthone (e.g., or a derivative thereof), a coumarin (e.g., a derivative thereof), an indoline, a porphyrin, a rhodamine, a pyrylium, a phenazine, a phenoxazine, an alpha hydroxy ketone, or a phosphine oxide. The sensitizer may be a phenothiazine, a thioxanthone, a coumarin (e.g., a derivative thereof, an alpha hydroxy ketone, or a phosphine oxide. The sensitizer may be a thioxanthone.

The sensitizer may be:

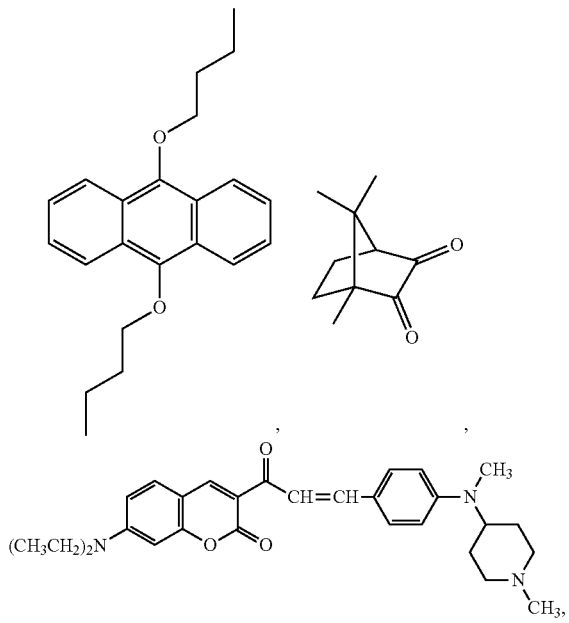

-continued

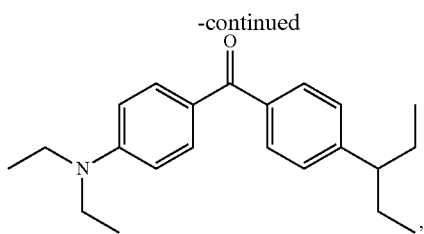

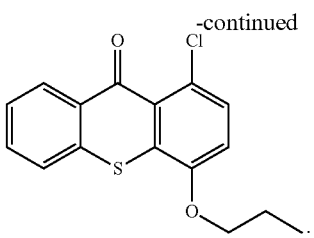

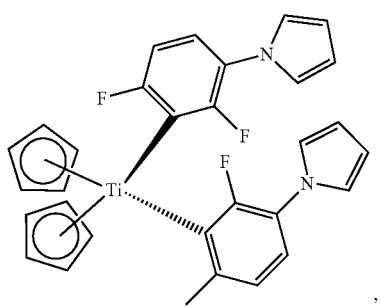

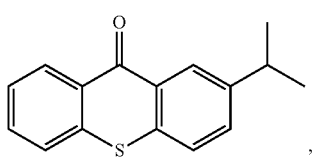

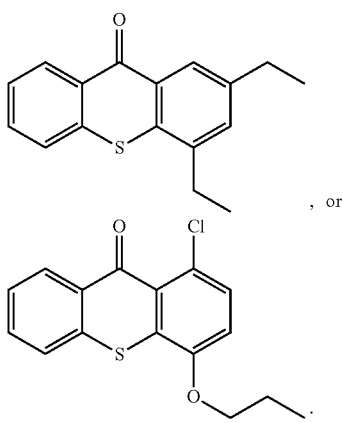, or

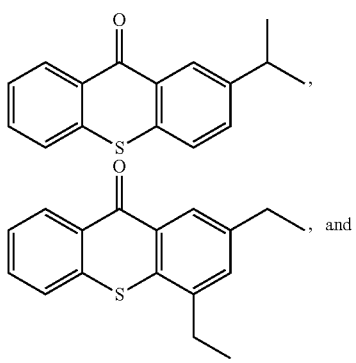.

The sensitizer can be a compound selected from the group consisting of:

,

, and

-continued

.

The sensitizer may be 2-Isopropylthioxanthone (ITX).

The sensitizer can be present (e.g., combined) in a mixture provided herein at a concentration of at least 0.1 parts per million (ppm) (e.g., 0.00001% by weight), 1 ppm (e.g., 0.0001% by weight), 10 ppm (e.g., 0.001% by weight), 100 ppm (e.g., 0.01% by weight), 1,000 ppm (e.g., 0.1% by weight), 10,000 ppm (e.g., 1% by weight), 50,000 ppm (e.g., 5% by weight), 100,000 ppm (e.g., 10% by weight), 150,000 ppm (e.g., 15% by weight), 200,000 ppm (e.g., 20% by weight), or more. The sensitizer can be present (e.g., combined) in a mixture provided herein at a concentration of at most 200,000 ppm (e.g., 20% by weight), 150,000 ppm (e.g., 15% by weight), 100,000 ppm (e.g., 10% by weight), 50,000 ppm (e.g., 5% by weight), 10,000 ppm (e.g., 1% by weight), 1,000 ppm (e.g., 0.1% by weight), 100 ppm (e.g., 0.01% by weight), 10 ppm (e.g., 0.001% by weight), 1 ppm (e.g., 0.0001% by weight), 0.1 ppm (e.g., 0.00001% by weight), or less. The sensitizer can be present (e.g., combined) in a mixture provided herein at a concentration within a range defined by any two of the preceding values. The sensitizer can be present (e.g., combined) in a mixture provided herein at a concentration from about 0.1 ppm (e.g., 0.00001% by weight) to about 200,000 ppm (e.g., 20% by weight). The sensitizer can be present (e.g., combined) in a mixture provided herein at a concentration from about 1 ppm (e.g., 0.00001% by weight) to about 20,000 ppm (e.g., 2% by weight).

The sensitizer and the polymer precursor can be present (e.g., combined) in a mixture provided herein at a weight ratio of at least 0.1 parts per million (ppm) (e.g., 0.00001% by weight), 1 ppm (e.g., 0.0001% by weight), 10 ppm (e.g., 0.001% by weight), 100 ppm (e.g., 0.01% by weight), 1,000 ppm (e.g., 0.1% by weight), 10,000 ppm (e.g., 1% by weight), 50,000 ppm (e.g., 5% by weight), 100,000 ppm (e.g., 10% by weight), 150,000 ppm (e.g., 15% by weight), 200,000 ppm (e.g., 20% by weight), or more. The sensitizer and the polymer precursor can be present (e.g., combined) in a mixture provided herein at a weight ratio of at most 200,000 ppm (e.g., 20% by weight), 150,000 ppm (e.g., 15% by weight), 100,000 ppm (e.g., 10% by weight), 50,000 ppm (e.g., 5% by weight), 10,000 ppm (e.g., 1% by weight), 1,000 ppm (e.g., 0.1% by weight), 100 ppm (e.g., 0.01% by weight), 10 ppm (e.g., 0.001% by weight), 1 ppm (e.g., 0.0001% by weight), 0.1 ppm (e.g., 0.00001% by weight), or less. The sensitizer and the polymer precursor can be present (e.g., combined) in a mixture provided herein at a weight ratio from 0.1 ppm to 200,000 ppm (e.g., 20% by weight). The sensitizer and the polymer precursor can be present (e.g., combined) in a mixture provided herein at a weight ratio from 1 ppm to 20,000 ppm (e.g., 2% by weight). The sensitizer and the polymer precursor can be present (e.g., combined) in a mixture provided herein at a weight ratio of 0.1 parts per million (ppm) (e.g., 0.00001% by weight), 1 ppm (e.g., 0.0001% by weight), 10 ppm (e.g., 0.001% by weight), 100 ppm (e.g., 0.01% by weight), 1,000 ppm (e.g., 0.1% by weight), 10,000 ppm (e.g., 1% by weight), 50,000 ppm (e.g., 5% by weight), 100,000 ppm (e.g., 10% by weight), 150,000 ppm (e.g., 15% by weight), 200,000 ppm (e.g., 20% by weight), or a range between any two of the foregoing values (inclusive).

Polymer Precursors:

The polymer precursor may be selected from the group consisting of a dicyclopentadiene, norbornene, aliphatic olefin, cyclooctene, cyclooctadiene, tricyclopentadiene, polybutadiene, an ethylene propylene diene monomer (EPDM) rubber, a polypropylene, a polyethylene, a cyclic olefin polymer (e.g., a cyclic olefin copolymer), and a diimide.

The dicyclopentadiene may be a poly(dicyclopentadiene). The poly(dicyclopentadiene) may be selected from the group consisting of a linear poly(dicyclopentadiene), a branched (e.g., hyperbranched) poly(dicyclopentadiene), a crosslinked poly(dicyclopentadiene), an oligomeric poly(dicyclopentadiene), or a polymeric poly(dicyclopentadiene).

The norbornene may be selected from the group consisting of an alkyl norbornene (e.g., ethylidene norbornene), a norbornene diimide, and a multifunctional norbornene crosslinker (e.g. di-norbornene, tri-norbornene).

Olefinic precursors may be used in tandem with the alkynes (e.g., employed as part of the feedstock mixtures or in sequential processing of the product polymers). Strained ring systems may be beneficial for ROMP reactions. The olefinic precursor may be substituted or unsubstituted cyclooctatetraenes (e.g., cyclooctatetraene).

A polymer precursor provided herein may comprise a ring systems (e.g., strained ring systems). Such cyclic olefins may be optionally substituted, optionally heteroatom-containing, mono-unsaturated, di-unsaturated, or poly-unsaturated $C_5$ to $C_{24}$ hydrocarbons that may be mono-, di-, or poly-cyclic. The cyclic olefin may be a strained or unstrained cyclic olefin.

A cyclic polymer precursor provided herein may be represented by the structure of formula (A)

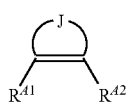
(A)

wherein:

$R^{A1}$ and $R^{A2}$ is selected independently from the group consisting of hydrogen, hydrocarbyl (e.g., $C_1$-$C_{20}$ alkyl, $C_5$-$C_{20}$ aryl, $C_5$-$C_{30}$ aralkyl, or $C_5$-$C_{30}$ alkaryl), substituted hydrocarbyl (e.g., substituted $C_1$-$C_{20}$ alkyl, $C_5$-$C_{20}$ aryl, $C_5$-$C_{30}$ aralkyl, or $C_5$-$C_{30}$ alkaryl), heteroatom-containing hydrocarbyl (e.g., $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl), and substituted heteroatom-containing hydrocarbyl (e.g., substituted $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl).

J is a saturated or unsaturated hydrocarbylene, substituted hydrocarbylene, heteroatom-containing hydrocarbylene, or substituted heteroatom-containing hydrocarbylene linkage.

Mono-unsaturated cyclic olefins encompassed by structure (A) may be represented by the structure (B):

(B)

wherein:

b is an integer the range of 1 to 10 (e.g., 1 to 5), $R^{A1}$ and $R^{A2}$ are as defined above for structure (A), and $R^{B1}$, $R^{B2}$, $R^{B3}$, $R^{B4}$, $R^{B5}$, and $R^{B6}$ are independently selected from the group consisting of hydrogen, hydrocarbyl, substituted hydrocarbyl, heteroatom-containing hydrocarbyl, substituted heteroatom-containing hydrocarbyl and —(Z*)$_n$-Fn where n, Z* and Fn are as defined hereinabove, and wherein if any of the $R^{B1}$ through $R^{B6}$ moieties is substituted hydrocarbyl or substituted heteroatom-containing hydrocarbyl, the substituents may include one or more —(Z*)$_n$-Fn groups. Accordingly, $R^{B1}$, $R^{B2}$, $R^{B3}$, $R^{B4}$, $R^{B5}$, and $R^{B6}$ may be, for example, hydrogen, hydroxyl, $C_1$-$C_{20}$ alkyl, $C_5$-$C_{20}$ aryl, $C_1$-$C_{20}$ alkoxy, $C_5$-$C_{20}$ aryloxy, $C_2$-$C_{ao}$ alkoxycarbonyl, $C_5$-$C_{20}$ aryloxycarbonyl, amino, amido, nitro, etc.

Furthermore, any of the $R^{B1}$, $R^{B2}$, $R^{B3}$, $R^{B4}$, $R^{B5}$, and $R^{B6}$ moieties can be linked to any of the other $R^{B1}$, $R^{B2}$, $R^{B3}$, $R^{B4}$, $R^{B5}$, and $R^{B6}$ moieties to provide a substituted or unsubstituted alicyclic group containing 4 to 30 ring carbon atoms or a substituted or unsubstituted aryl group containing 6 to 18 ring carbon atoms or combinations thereof and the linkage may include heteroatoms or functional groups, e.g. the linkage may include without limitation an ether, ester, thioether, amino, alkylamino, imino, or anhydride moiety. The alicyclic group can be monocyclic, bicyclic, or polycyclic. The cyclic group can contain monounsaturation or multiunsaturation. The rings may contain monosubstitution or multisubstitution, wherein the substituents may be independently selected from hydrogen, hydrocarbyl, substituted hydrocarbyl, heteroatom-containing hydrocarbyl, substituted heteroatom-containing hydrocarbyl, —(Z*)$_n$-Fn where n is zero or 1, Z* and Fn are as defined hereinabove, and functional groups (Fn) provided above.

Examples of mono-unsaturated, monocyclic olefins encompassed by structure (B) include, without limitation, cyclopentene, cyclohexene, cycloheptene, cyclooctene, cyclononene, cyclodecene, cycloundecene, cyclododecene, tricyclodecene, tetracyclodecene, octacyclodecene, and cycloeicosene, and substituted versions thereof such as 1-methylcyclopentene, 1-ethylcyclopentene, 1-isopropylcyclohexene, 1-chloropentene, 1-fluorocyclopentene, 4-methylcyclopentene, 4-methoxy-cyclopentene, 4-ethoxy-cyclopentene, cyclopent-3-ene-thiol, cyclopent-3-ene, 4-methyl sulfanyl-cyclopentene, 3-methylcyclohexene, 1-methylcyclooctene, 1,5-dimethylcyclooctene, etc.

Monocyclic diene reactants encompassed by structure (A) may be generally represented by the structure (C):

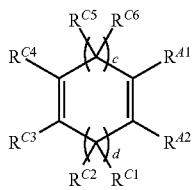

(C)

wherein:
c and d are independently integers in the range of 1 to about 8 (e.g., 2 to 4, such as 2 (such that the reactant is a cyclooctadiene)),
$R^{A1}$ and $R^{A2}$ are as defined above for structure (A), and $R^{C1}$, $R^{C2}$, $R^{C3}$, $R^{C4}$, $R^{C5}$, and $R^{C6}$ are defined as for $R^{B1}$ through $R^{B6}$.

In this case, it may be preferred that $R^{C3}$ and $R^{C4}$ be non-hydrogen substituents, in which case the second olefinic moiety is tetrasubstituted. Examples of monocyclic diene reactants include, without limitation, 1,3-cyclopentadiene, 1,3-cyclohexadiene, 1,4-cyclohexadiene, 5-ethyl-1,3-cyclohexadiene, 1,3-cycloheptadiene, cyclohexadiene, 1,5-cyclooctadiene, 1,3-cyclooctadiene, and substituted analogs thereof. Triene reactants may be analogous to the diene structure (C), and can contain at least one methylene linkage between any two olefinic segments.

Bicyclic and polycyclic olefins encompassed by structure (A) may be generally represented by the structure (D):

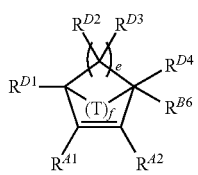

(D)

wherein:
$R^{A1}$ and R are as defined above for structure (A),
$R^{D1}$, $R^{D2}$, $R^{D3}$, and $R^{D4}$ are as defined for $R^{B1}$ through $R^{B6}$,
e is an integer in the range of 1 to 8 (e.g., 2 to 4)
f is 1 or 2;
T is lower alkylene or alkenylene (generally substituted or unsubstituted methyl or ethyl),
$CHR^{G1}$, $C(R^{G1})_2$, O, S, N—$R^{G1}$, P—$R^{G1}$, O=P—$R^{G1}$, $Si(R^{G1})_2$, B—$R^{G1}$, or As—$R^{G1}$ where $R^{G1}$ is alkyl, alkenyl, cycloalkyl, cycloalkenyl, aryl, alkaryl, aralkyl, or alkoxy.

Furthermore, any of the $R^{D1}$, $R^{D2}$, $R^{D3}$, and $R^{D4}$ moieties can be linked to any of the other $R^{D1}$, $R^{D2}$, $R^{D3}$, and $R^{D4}$ moieties to provide a substituted or unsubstituted alicyclic group containing 4 to 30 ring carbon atoms or a substituted or unsubstituted aryl group containing 6 to 18 ring carbon atoms or combinations thereof and the linkage may include heteroatoms or functional groups, e.g. the linkage may include without limitation an ether, ester, thioether, amino, alkylamino, imino, or anhydride moiety. The cyclic group can be monocyclic, bicyclic, or polycyclic. The cyclic group can contain mono-unsaturation or multi-unsaturation. The ring may contain mono-substitution or multi-substitution, wherein the substituents are independently selected from hydrogen, hydrocarbyl, substituted hydrocarbyl, heteroatom-containing hydrocarbyl, substituted heteroatom-containing hydrocarbyl, —$(Z^*)_n$—Fn where n is zero or 1, $Z^*$ and Fn are as defined hereinabove, and functional groups (Fn) provided above.

Cyclic olefins encompassed by structure (D) may be in the norbornene family. A norbornene may include at least one norbornene or substituted norbornene moiety, including without limitation norbornene, substituted norbornene(s), norbornadiene, substituted norbornadiene(s), polycyclic norbornenes, and substituted polycyclic norbornene(s).

Norbornenes may be generally represented by the structure (E):

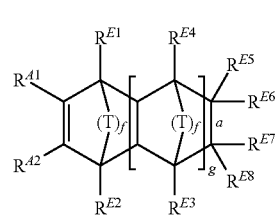

(E)

wherein:
$R^{A1}$ and $R^{A2}$ are as defined above for structure (A),
T is as defined above for structure (D),
$R^{E1}$, $R^{E2}$, $R^{E3}$, $R^{E4}$, $R^{E5}$, $R^{E6}$, $R^{E7}$, and $R^{E8}$ are as defined for $R^{B1}$ through $R^{B6}$, and
"a" represents a single bond or a double bond,
f is 1 or 2,
"g" is an integer from 0 to 5, and when "a" is a double bond one of $R^{E5}$, $R^{E6}$ and one of $R^{E7}$, $R^{E8}$ is not present.

Furthermore, any of the $R^{E5}$, $R^{E6}$, $R^{E7}$, and $R^{E8}$ moieties can be linked to any of the other $R^{E5}$, $R^{E6}$, $R^{E7}$, and $R^{E8}$ moieties to provide a substituted or unsubstituted alicyclic group containing 4 to 30 ring carbon atoms or a substituted or unsubstituted aryl group containing 6 to 18 ring carbon atoms or combinations thereof and the linkage may include heteroatoms or functional groups, e.g. the linkage may include without limitation an ether, ester, thioether, amino, alkylamino, imino, or anhydride moiety. The cyclic group can be monocyclic, bicyclic, or polycyclic. The cyclic group can contain monounsaturation or multiunsaturation. The ring may contain monosubstitution or multisubstitution, wherein the substituents are independently selected from hydrogen, hydrocarbyl, substituted hydrocarbyl, heteroatom-containing hydrocarbyl, substituted heteroatom-containing hydrocarbyl, —$(Z^*)_n$—Fn where n is zero or 1, $Z^*$ and Fn are as defined hereinabove, and functional groups (Fn) provided above.

Cyclic olefins possessing at least one norbornene moiety may have the structure (F):

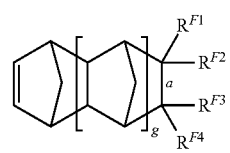

(F)

Wherein:
$R^{F1}$, $R^{F2}$, $R^{F3}$, and $R^{F4}$, are as defined for $R^{B1}$ through $R^{B6}$, and
"a" represents a single bond or a double bond, "g" is an integer from 0 to 5, and when "a" is a double bond one of $R^{F1}$, $R^{F2}$ and one of $R^{F3}$, $R^{F4}$ is not present.

Furthermore, any of the $R^{F1}$, $R^{F2}$, $R^{F3}$ and $R^{F4}$ moieties can be linked to any of the other $R^{F1}$, $R^{F2}$, $R^{F3}$ and $R^{F4}$ moieties to provide a substituted or unsubstituted alicyclic group containing 4 to 30 ring carbon atoms or a substituted or unsubstituted aryl group containing 6 to 18 ring carbon atoms or combinations thereof and the linkage may include heteroatoms or functional groups, e.g. the linkage may include without limitation an ether, ester, thioether, amino, alkylamino, imino, or anhydride moiety. The alicyclic group can be monocyclic, bicyclic, or polycyclic. The cyclic group can contain monounsaturation or multiunsaturation. The rings may contain monosubstitution or multisubstitution, wherein the substituents are independently selected from hydrogen, hydrocarbyl, substituted hydrocarbyl, heteroatom-containing hydrocarbyl, substituted heteroatom-containing hydrocarbyl, —$(Z^*)_n$-Fn where n is zero or 1, $Z^*$ and Fn are as defined hereinabove, and functional groups (Fn) provided above.

In some embodiments, the polymer precursor is:

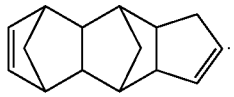 [SMILES: C1=CC2C(C1)C1CC2C2C3C=CC(C3)C12]

A route for the preparation of hydrocarbyl substituted and functionally substituted norbornenes may employ the Diels-Alder cycloaddition reaction. For example, cyclopentadiene or substituted cyclopentadiene may be reacted with a suitable dienophile at elevated temperatures to form the substituted norbornene adduct, which is generally shown by the following reaction Scheme 1:

SCHEME 1

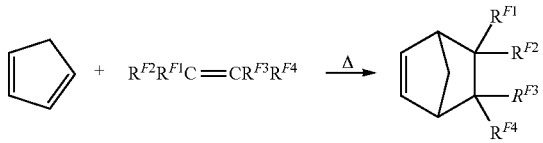

wherein:
$R^{F1}$ to $R^{F4}$ are as previously defined for structure (F).

Other norbornene adducts can be prepared by the thermal pyrolysis of dicyclopentadiene in the presence of a suitable dienophile. The reaction may proceed by the initial pyrolysis of dicyclopentadiene to cyclopentadiene followed by the Diels-Alder cycloaddition of cyclopentadiene and the dienophile to give the adduct shown below in Scheme 2:

SCHEME 2

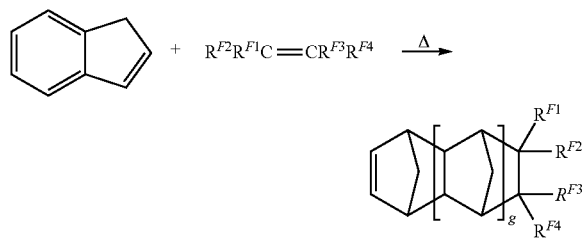

wherein:
"g" is an integer from 0 to 5, and
$R^{F1}$ to $R^{F4}$ are as previously defined for structure (F).

Norbornadiene and higher Diels-Alder adducts thereof similarly can be prepared by the thermal reaction of cyclopentadiene and dicyclopentadiene in the presence of an acetylenic reactant as shown below in Scheme 3:

SCHEME

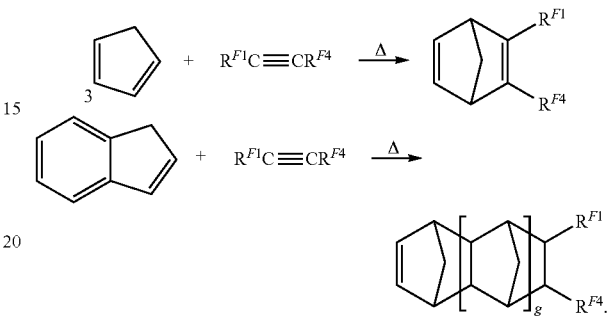

wherein:
"g" is an integer from 0 to 5, $R^{F1}$ and $R^{F4}$ are as previously defined for structure (F)

Examples of bicyclic and polycyclic olefins may include, without limitation, dicyclopentadiene (DCPD); trimer and other higher order oligomers of cyclopentadiene including without limitation tricyclopentadiene (cyclopentadiene trimer), cyclopentadiene tetramer, and cyclopentadiene pentamer; ethylidenenorbornene; dicyclohexadiene; norbornene; 5-methyl-2-norbornene; 5-ethyl-2-norbornene; 5-isobutyl-2-norbornene; 5,6-dimethyl-2-norbornene; 5-phenylnorbornene; 5-benzylnorbornene; 5-acetylnorbornene; 5-methoxycarbonylnorbornene; 5-ethyoxycarbonyl-1-norbornene; 5-methyl-5-methoxy-carbonylnorbornene; 5-cyanonorbornene; 5,5,6-trimethyl-2-norbornene; cyclo-hexenylnorbornene; endo, exo-5,6-dimethoxynorbornene; endo, endo-5,6-dimethoxynorbornene; endo, exo-5,6-dimethoxycarbonylnorbornene; endo,endo-5,6-dimethoxycarbonylnorbornene; 2,3-dimethoxynorbornene; norbornadiene; tricycloundecene; tetracyclododecene; 8-methyltetracyclododecene; 8-ethyltetracyclododecene; 8-methoxycarbonyltetracyclododecene; 8-methyl-8-tetracyclododecene; 8-cyanotetracyclododecene; pentacyclopentadecene; pentacyclohexadecene; and the like, and their structural isomers, stereoisomers, and mixtures thereof. Additional examples of bicyclic and polycyclic olefins include, without limitation, $C_2$-$C_{12}$ hydrocarbyl substituted norbornenes such as 5-butyl-2-norbornene, 5-hexyl-2-norbornene, 5-octyl-2-norbornene, 5-decyl-2-norbornene, 5-dodecyl-2-norbornene, 5-vinyl-2-norbornene, 5-ethylidene-2-norbornene, 5-isopropenyl-2-norbornene, 5-propenyl-2-norbornene, and 5-butenyl-2-norbornene, and the like.

Cyclic olefins may include $C_5$ to $C_{24}$ unsaturated hydrocarbons (e.g., $C_5$ to $C_{24}$ cyclic hydrocarbons that contain one or more (typically 2 to 12) heteroatoms such as O, N, S, or P). For example, crown ether cyclic olefins may include numerous O heteroatoms throughout the cycle, and these are within the scope of the disclosure. Cyclic olefins provided herein may be $C_5$ to $C_{24}$ hydrocarbons that contain one or more (typically 2 or 3) olefins. For example, the cyclic olefin may be mono-, di-, or tri-unsaturated. Examples of cyclic olefins include without limitation cyclooctene, cyclododecene, and (c,t,t)-1,5,9-cyclododecatriene.

The cyclic olefins may also comprise multiple (typically 2 or 3) rings. For example, the cyclic olefin may be mono-, di-, or tri-cyclic. The rings may be fused. Examples of cyclic olefins that comprise multiple rings include, for example, norbornene, dicyclopentadiene, tricyclopentadiene, and 5-ethylidene-2-norbornene.

The cyclic olefin may be substituted, for example, a $C_5$ to $C_{24}$ cyclic hydrocarbon wherein one or more (typically 2, 3, 4, or 5) of the hydrogens are replaced with non-hydrogen substituents. For example, a cyclic olefin functionalized with an alcohol group may be used to prepare a telechelic polymer comprising pendent alcohol groups. Functional groups on the cyclic olefin may be protected in cases where the functional group interferes with the metathesis catalyst, and any of the protecting groups commonly used in the art may be employed. Acceptable protecting groups may be found, for example, in Greene et al., Protective Groups in Organic Synthesis, 3rd Ed. (New York: Wiley, 1999). A non-limiting list of protecting groups includes: (for alcohols) acetyl, benzoyl, benzyl, β-Methoxyethoxymethyl ether (MEM), Dimethoxytrityl, [bis-(4-methoxyphenyl)phenylmethyl] (DMT), methoxymethyl ether (MOM), methoxytrityl [(4-methoxyphenyl)diphenylmethyl, MMT), p-methoxybenzyl ether (PMB), methylthiomethyl ether, pivaloyl (Piv), tetrahydropyranyl (THP), tetrahydrofuran (THF), trityl (triphenylmethyl, Tr), silyl ethers (most popular ones include trimethylsilyl (TMS), tert-butyldimethylsilyl (TBDMS), tri-iso-propylsilyloxymethyl (TOM), and triisopropylsilyl (TIPS) ethers, (for amines) tert-butyloxycarbonyl glycine, carbobenzyloxy (Cbz) group, p-methoxybenzyl carbonyl (Moz or MeOZ) group, tert-butyloxycarbonyl (BOC) group, 9-fluorenylmethyloxycarbonyl (FMOC) group, acetyl (Ac) group, benzoyl (Bz) group, benzyl (Bn), carbamate group, p-methoxybenzyl (PMB), 3,4-dimethoxybenzyl (DMPM), p-methoxyphenyl (PMP) group, tosyl (Ts) group, (for carbonyls) acetals and ketals, acylals, dithianes, (for carboxylic acids) methyl esters, benzyl esters, tert-butyl esters, esters of 2,6-disubstituted phenols (e.g. 2,6-dimethylphenol, 2,6-di-isopropylphenol, 2,6-di-tert-butylphenol), silyl esters, orthoesters, oxazoline, (for phosphate) 2-cyanoethyl, and methyl. In the specific case of arginine (Arg) side chains, protection is important because of the propensity of the basic quanidinium group to produce side reactions. In cases described herein, effective protective groups include 2,2,5,7,8-pentamethylchroman (Pmc), 2,2,4,6,7-pentamethyldihydrobenzofurane (Pbf) and 1,2-dimethylindole-3-sulfonyl (MIS) groups.

Examples of functionalized cyclic olefins include without limitation 2-hydroxymethyl-5-norbornene, 2-[(2-hydroxyethyl)carboxylate]-5-norbornene, cydecanol, 5-n-hexyl-2-norbornene, 5-n-butyl-2-norbornene.

Cyclic olefins incorporating any combination of the abovementioned features (e.g., heteroatoms, substituents, multiple olefins, multiple rings) may be suitable for the methods disclosed herein.

The cyclic olefins provided herein may be strained or unstrained. Ring strain may be one factor in determining the reactivity of a molecule towards ring-opening olefin metathesis reactions. Highly strained cyclic olefins, such as certain bicyclic compounds, may readily undergo ring opening reactions with olefin metathesis catalysts. Less strained cyclic olefins, such as certain unsubstituted hydrocarbon monocyclic olefins, may be less reactive. In some cases, ring opening reactions of relatively unstrained cyclic olefins may become possible when performed in the presence of the olefinic compounds disclosed herein.

A plurality of cyclic olefins may be used herein. For example, two cyclic olefins selected from the cyclic olefins described hereinabove may be employed in order to form metathesis products that incorporate both cyclic olefins (e.g., a second cyclic olefin may be a cyclic alkenol (e.g., a $C_5$-$C_{24}$ cyclic hydrocarbon wherein at least one of the hydrogen substituents is replaced with an alcohol or protected alcohol moiety to yield a functionalized cyclic olefin).

The use of a plurality of cyclic olefins (e.g., wherein at least one of the cyclic olefins is functionalized), may provide for further control over the positioning of functional groups within the product(s). For example, the density of cross-linking points can be controlled in polymers and macromonomers prepared using the methods disclosed herein. Control over the quantity and density of substituents and functional groups may provide control over the physical properties (e.g., melting point, tensile strength, glass transition temperature, etc.) of the product(s). Control over these and other properties is possible for reactions using only a single cyclic olefin, but it will be appreciated that the use of a plurality of cyclic olefins further enhances the range of possible metathesis products and polymers formed.

Cyclic olefins provided herein may include, for example, dicyclopentadiene; tricyclopentadiene; dicyclohexadiene; norbornene; 5-methyl-2-norbornene; 5-ethyl-2-norbornene; 5-isobutyl-2-norbornene; 5,6-dimethyl-2-norbornene; 5-phenylnorbornene; 5-benzylnorbornene; 5-acetylnorbornene; 5-methoxycarbonylnorbornene; 5-ethoxycarbonyl-1-norbornene; 5-methyl-5-methoxy-carbonylnorbornene; 5-cyanonorbornene; 5,5,6-trimethyl-2-norbornene; cyclohexenylnorbornene; endo, exo-5,6-dimethoxynorbornene; endo, endo-5,6-dimethoxynorbornene; endo, exo-5-6-dimethoxycarbonylnorbornene; endo, endo-5,6-dimethoxycarbonylnorbornene; 2,3-dimethoxynorbornene; norbornadiene; tricycloundecene; tetracyclododecene; 8-methyltetracyclododecene; 8-ethyl-tetracyclododecene; 8-methoxycarbonyltetracyclododecene; 8-methyl-8-tetracyclo-dodecene; 8-cyanotetracyclododecene; pentacyclopentadecene; pentacyclohexadecene; higher order oligomers of cyclopentadiene such as cyclopentadiene tetramer, cyclopentadiene pentamer, and the like; and $C_2$-$C_{12}$ hydrocarbyl substituted norbornenes such as 5-butyl-2-norbornene; 5-hexyl-2-norbornene; 5-octyl-2-norbornene; 5-decyl-2-norbornene; 5-dodecyl-2-norbornene; 5-vinyl-2-norbornene; 5-ethylidene-2-norbornene; 5-isopropenyl-2-norbornene; 5-propenyl-2-norbornene; and 5-butenyl-2-norbornene, and the like. Even more preferred cyclic olefins include dicyclopentadiene, tricyclopentadiene, and higher order oligomers of cyclopentadiene, such as cyclopentadiene tetramer, cyclopentadiene pentamer, and the like, tetracyclododecene, norbornene, and $C_2$-$C_{12}$ hydrocarbyl substituted norbornenes, such as 5-butyl-2-norbornene, 5-hexyl-2-norbornene, 5-octyl-2-norbornene, 5-decyl-2-norbornene, 5-dodecyl-2-norbornene, 5-vinyl-2-norbornene, 5-ethylidene-2-norbornene, 5-isopropenyl-2-norbornene, 5-propenyl-2-norbornene, 5-butenyl-2-norbornene, and the like.

In certain embodiments, each of these Structures A-F may further comprise pendant substituents that are capable of crosslinking with one another or added crosslinking agents. For example, $R^{A1}$, $R^{A2}$, $R^{B1}$, $R^{B2}$, $R^{B3}$, $R^{B4}$, $R^{B5}$, $R^{B6}$, $R^{C1}$, $R^{C2}$, $R^{C3}$, $R^{C4}$, $R^{C5}$, $R^{C6}$, $R^{D1}$, $R^{D2}$, $R^{D3}$, $R^{D4}$, $R^{E1}$, $R^{E2}$, $R^{E3}$, $R^{E4}$, $R^{E5}$, $R^{E6}$, $R^{E7}$, $R^{E8}$, $R^{F1}$, $R^{F2}$, $R^{F3}$, and $R^{F4}$ may each independently represent pendant hydrocarbyl chains containing olefinic or acetylenic bonds capable of crosslinking with themselves or other unsaturated moieties under metathesis conditions. Within Structures A-F, at least one pair of substituents, $R^{B1}$ and $R^{B2}$, $R^{B3}$ and $R^{B4}$, and $R^{B5}$ and $R^{B6}$, $R^{C1}$ and $R^{C2}$, $R^{C5}$ and $R^{C6}$, $R^{D2}$ and $R^{D3}$, $R^{E5}$ and $R^{E6}$, $R^{E7}$ and $R^{E8}$, $R^{F1}$ and $R^{F2}$, and $R^{F3}$ and $R^{F4}$, can together form an optionally substituted exocyclic double bond, for example /=CH($C_{1-6}$-Fn).

When considering alternative olefinic precursors in the present methods, more preferred precursors may be those which, which when incorporated into polyacetylene polymers or copolymers, modify the electrical or physical character of the resulting polymer. One general class of such precursors are substituted annulenes and annulynes, for example [18]annulene-1,4;7,10;13,16-trisulfide. When co-polymerized with acetylene, this precursor can form a block copolymer as shown here:

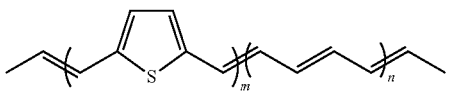

Substituted analogs of these trisulfides, as described below can also be used to provide corresponding substituted poly(thienylvinylene)-containing polymers or copolymers. For example, the 2,3,8,9,14,15-hexaoctyl derivative of [18] annulene-1,4;7,10;13,16-trisulfide is described in Horie, et al., "Poly(thienylvinylene) prepared by ring-opening metathesis polymerization: Performance as a donor in bulk heterojunction organic photovoltaic devices," *Polymer* 51 (2010) 1541-1547, which is incorporated by reference herein:

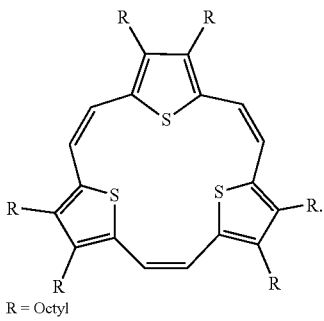
R = Octyl

In certain embodiments, the unsaturated organic precursor comprises a purely hydrocarbon compound having a structure:

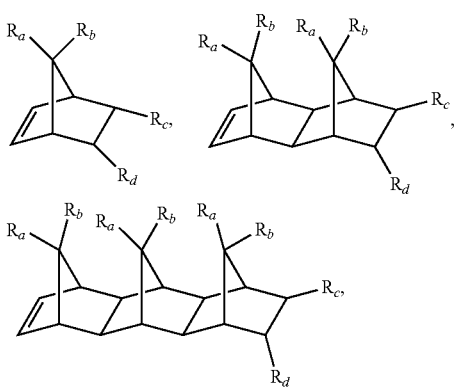

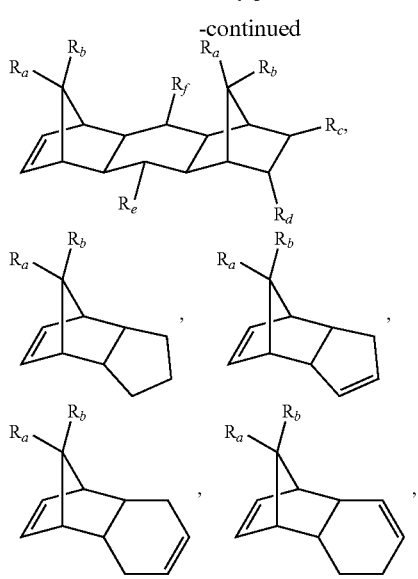

or a mixture thereof,
wherein
$R_a$, $R_b$, $R_c$, $R_d$, $R_e$, and $R_f$ are independently H or alkyl (such as $C_{1-20}$ alkyl, more such as $C_{1-10}$ alkyl).

The unsaturated organic precursor may comprise a hydrocarbon compound having a dicyclopentadiene structure, for example:

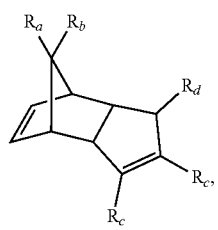

wherein:
$R_a$, $R_b$, $R_c$, $R_d$, $R_e$, and $R_f$ are independently H or alkyl (such as $C_{1-20}$ alkyl, such as $C_{1-10}$ alkyl). One such polymer resulting from such precursors comprises units having a structure:

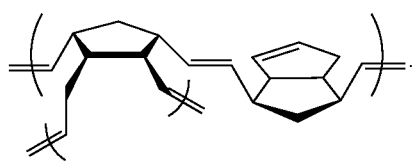
Poly(dicyclopentadiene)

These hydrocarbon precursors may be employed (e.g., when the final polymerized product or article derived therefrom is to be subject to aggressive chemical conditions). For example, patterned products or article derived therefrom prepared from dicyclopentadiene structures may be effective in resisting aqueous HF (e.g., attractive for use as etching masks in semi-conductor or other electronic processing).

In other embodiments, the unsaturated polymerizable material matrix may include mono-, di-, or polyfunctionalized cyclic or alicyclic alkenes or alkynes (e.g., which include functional groups, including for example, alcohols, amines, amides, carboxylic acids and esters, phosphines, phosphonates, sulfonates or the like). Optionally substituted bicyclo[2.2.1]hept-5-ene-2,3,dicarboxylic acid diesters, 7-oxa-bicyclo[2.2.1]hept-5-ene-2,3,dicarboxylic acid diesters, 4-oxa-tricyclo[5.2.1.0$^{2,6}$] dec-8-ene-3,5-diones, 4,10-dioxa-tricyclo[5.2.1.0$^{2,6}$] dec-8-ene-3,5-diones, 4-aza-tricyclo[5.2.1.0$^{2,6}$] dec-8-ene-3,5-diones, 10-oxa-4-aza-tricyclo[5.2.1.0$^{2,6}$] dec-8-ene-3,5-diones, or simple di-substituted alkenes, including bisphosphines may be used. In certain embodiments, these functionalized alkenes include those having structures such as:

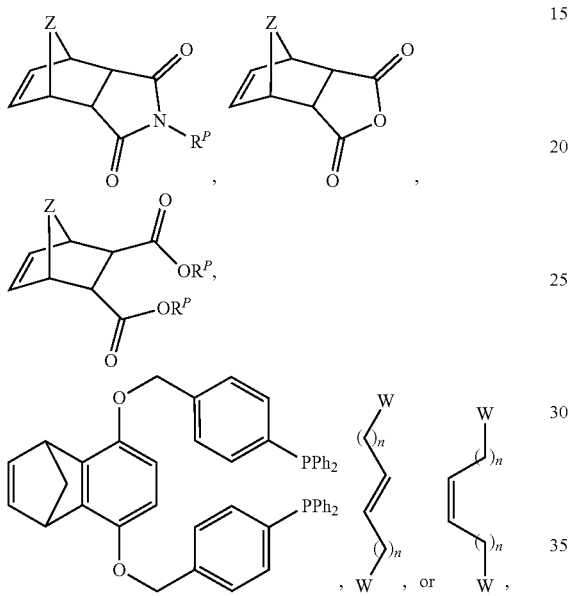

wherein:

Z is —O— or C(R$_a$)(R$_b$);

R$^P$ is independently H; or C$_{1-6}$ alkyl optionally substituted at the terminus with —N(Ra)(R$_b$), —O—R$_a$, —C(O)O—R$_a$, —OC(O)—(C$_{1-6}$ alkyl), or —OC(O)—(C$_{6-10}$ aryl); or an optionally protected sequence of 3 to 10 amino acids (such as including R-G-D or arginine-glycine-aspartic acid);

W is independently —N(Ra)(R$_b$), —O—R$_a$, or —C(O)O—R$_a$, —P(O)(OR$_a$)$_2$, —SO$_2$(OR$^a$), or SO$_3^-$;

R$_a$ and R$_b$ are independently H or C$_{1-6}$ alkyl;

the C$_{6-10}$ aryl is optionally substituted with 1, 2, 3, 4, or 5 optionally protected hydroxyl groups (the protected hydroxyl groups such as being benzyl); and n is independently 1, 2, 3, 4, 5, or 6.

Non-limiting examples of such functionalized materials include:

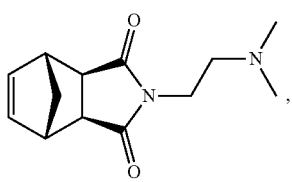

-continued

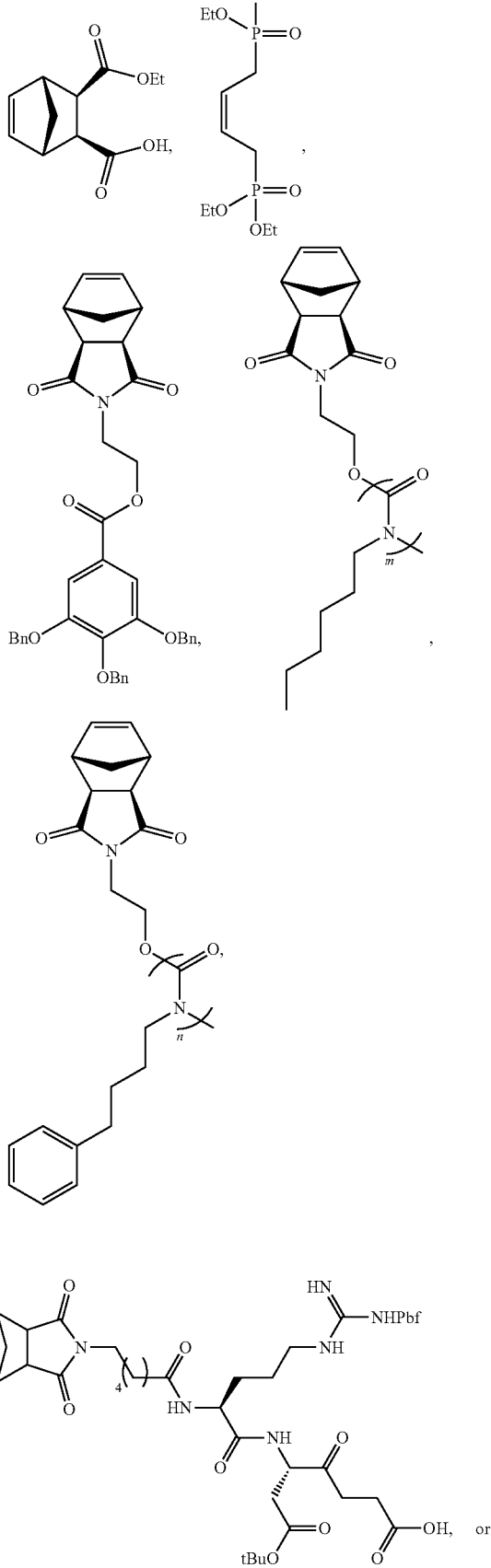

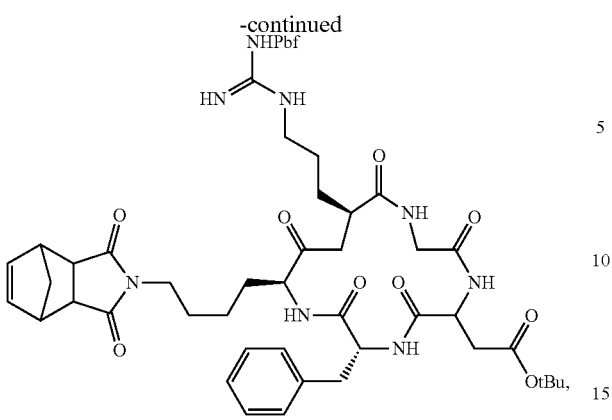

where Bn is benzyl, tBu is tert-butyl, and Pbf is 2,2,4,6,7-pentamethyldihydrobenzofuran. Other protecting groups may also be employed.

Incorporation of such functional groups may provide further functionalization of the pre-polymerized or polymerized compositions (e.g., expanding the utility options available for such compositions). Such functional groups can be used as linking points for the additional of other materials, including, for example, natural or synthetic amino acid sequences. In certain embodiments, $R^P$ can be further functionalized to include:

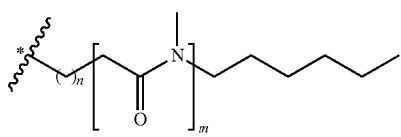

Polymerized products (either 2-dimensional optionally patterned coatings or optionally patterned 3-dimensional structures) prepared from the pre-polymerized compositions may be useful as scaffolds for drug delivery or tissue regeneration. Films or articles comprising pendant optionally protected sequence of 3 to 10 amino acids (such as including R-G-D or arginine-glycine-aspartic acid) are known to be useful in tissue regeneration applications and the present inventive compositions and methods provide convenient routes to these materials Catalytic organometallic materials may be incorporated into such matrices. Photosensitive compositions provided herein may comprise an acid-activated ruthenium metathesis catalyst admixed or dissolved within a polymerizable material matrix comprising at least one unsaturated organic precursor and at least one unsaturated tethered organometallic precursor, or ligand capable of coordinating to form an organometallic precursor (e.g., vinyl bipyridine, bisphosphines, and carbene precursors) each organic and organometallic precursor having at least one alkene or one alkyne bond.

An unsaturated tethered organometallic precursor may be an organometallic complex having a pendant alkene or alkyne group capable of being incorporated into the polymerized matrix.

In some embodiments, the organometallic moiety comprises a Group 3 to Group 12 transition metal, such as Fe, Co, Ni, Ti, Al, Cu, Zn, Ru, Rh, Ag, Ir, Pt, Au, or Hg. In preferred embodiments, the organometallic moiety comprises Fe, Co, Ni, Ru, Rh, Ir, Pt, or Au. The organometallic moieties may be attached by or contain monodentate, bidentate, or polydentate ligands, for example cyclopentadienyls, imidazoline (or their carbene precursors), phosphines, polyamines, polycarboxylates, nitrogen macrocycles (e.g., porphyrins or corroles), provided these ligands contain the pendant alkene or alkyne group capable of being incorporated into the polymerized matrix. Non-limiting examples of this concept include:

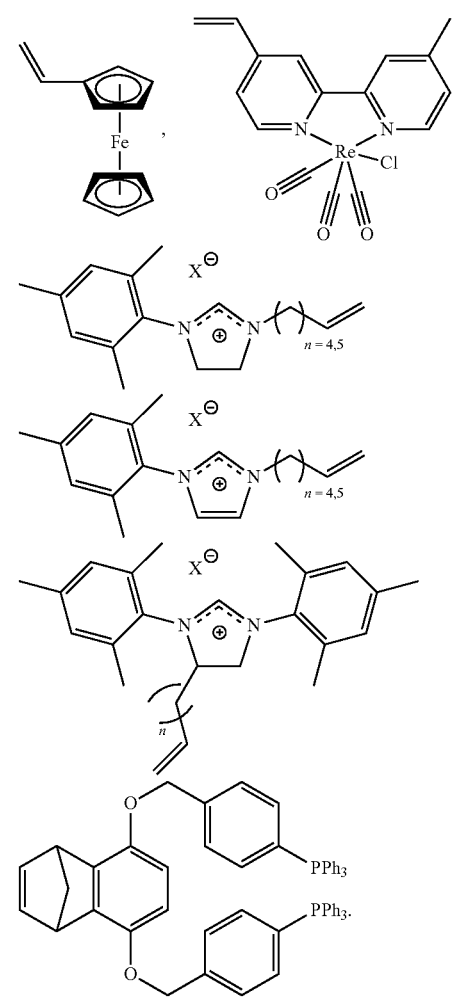

Representative chemistry of the polymerized product into which such an organometallic was incorporated is illustrated in U.S. patent application Ser. No. 14/505,824.

In certain embodiments, the organometallic moiety may catalyze the oxidation or reduction of an organic substrate under oxidizing or reducing conditions. Such oxidation reactions include, but are not limited to, oxidations of alkenes or alkynes to form alcohols, aldehydes, carboxylic acids or esters, ethers, or ketones, or the addition of hydrogen-halides or silanes across unsaturates. Such oxidation reactions include, but are not limited to, reduction of alkenes to alkanes and reduction of alkynes to alkenes or alkanes. Certain of these organometallic moieties may be used as pendant metathesis or cross-coupling catalysts or for splitting water.

In some embodiments, the polymer precursor is a compound having a structure of Formula (II):

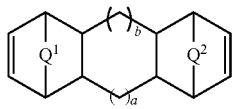

Formula (II)

wherein:
Q¹ and Q² are each independently optionally substituted alkylene; and
a and b are each independently 0, 1, or 2.

In some embodiments, $Q^1$ and $Q^2$ are each independently $C_1$-$C_6$ alkylene. In some embodiments, $Q^1$ and $Q^2$ are each independently methylene or ethylene. In some embodiments, $Q^1$ and $Q^2$ are each methylene. In some embodiments, a and b are each independently 0 or 1. In some embodiments, a is 1 and b is 0. In some embodiments, a and b are each 1.

In some embodiments, the polymer precursor is a compound selected from the group consisting of:

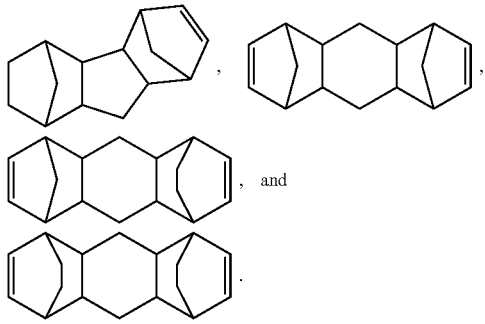

In some embodiments, the polymer precursor is a compound having a structure of Formula (III):

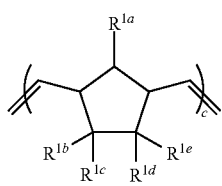

Formula (III)

wherein:
$R^{1a}$ is hydrogen or optionally substituted alkyl;
$R^{1b}$, $R^{1c}$, $R^{1d}$, and $R^{1e}$ are each independently hydrogen, optionally substituted alkyl, $R^{1c}$ and $R^{1d}$ are taken together with the atoms to which they are attached to form an optionally substituted cycloalkyl, $R^{1b}$ and $R^{1c}$ are taken together with the atoms to which they are attached to form an optionally substituted alkenyl, or $R^{1d}$ and $R^{1e}$ are taken together with the atoms to which they are attached to form an optionally substituted alkenyl; and
c is an integer from 1-20.

In some embodiments, $R^{1a}$ is hydrogen. In some embodiments, $R^{1b}$ is hydrogen. In some embodiments, $R^{1c}$ is hydrogen. In some embodiments, $R^{1d}$ is hydrogen. In some embodiments, $R^{1e}$ is hydrogen.

In some embodiments, $R^{1b}$ and $R^{1c}$ are taken together with the atoms to which they are attached to form an optionally substituted alkenyl. In some embodiments, $R^{1d}$ and $R^{1e}$ are taken together with the atoms to which they are attached to form an optionally substituted alkenyl.

In some embodiments, $R^{1b}$ and $R^{1c}$ are taken together with the atoms to which they are attached to form an optionally substituted $C_2$-$C_6$ alkenyl. In some embodiments, $R^{1d}$ and $R^{1e}$ are taken together with the atoms to which they are attached to form an optionally substituted $C_2$-$C_6$ alkenyl. In some embodiments, the optionally substituted $C_2$-$C_6$ alkenyl is substituted with alkyl (e.g., $C_1$-$C_6$ alkyl). In some embodiments, the optionally substituted $C_2$-$C_6$ alkenyl is —CH═CH—$C_1$-$C_6$ alkyl. In some embodiments, the optionally substituted $C_2$-$C_6$ alkenyl is —CH═CH—$CH_3$. In some embodiments, $R^{1b}$ and $R^{1c}$ are hydrogen and $R^{1e}$ and $R^{1e}$ are taken together with the atoms to which they are attached to form an optionally substituted $C_2$-$C_6$ alkenyl (e.g., —CH═CH—$CH_3$). In some embodiments, $R^{1d}$ and $R^{1e}$ are hydrogen and $R^{1b}$ and $R^{1c}$ are taken together with the atoms to which they are attached to form an optionally substituted $C_2$-$C_6$ alkenyl (e.g., —CH═CH—$CH_3$). In some embodiments, $R^a$, $R^{1b}$ and $R^{1c}$ are hydrogen and $R^{1e}$ and $R^{1e}$ are taken together with the atoms to which they are attached to form an optionally substituted $C_2$-$C_6$ alkenyl (e.g., —CH═CH—$CH_3$). In some embodiments, $R^a$, $R^{1d}$ and $R^{1e}$ are hydrogen and $R^{1b}$ and $R^{1c}$ are taken together with the atoms to which they are attached to form an optionally substituted $C_2$-$C_6$ alkenyl (e.g., —CH═CH—$CH_3$).

In some embodiments, $R^{1c}$ and $R^{1d}$ are taken together with the atoms to which they are attached to form an optionally substituted cycloalkyl.

In some embodiments, $R^{1a}$ is hydrogen and $R^c$ and $R^d$ are taken together with the atoms to which they are attached to form an optionally substituted cycloalkyl. In some embodiments, the optionally substituted cycloalkyl is an optionally substituted $C_3$-$C_6$ cycloalkyl. In some embodiments, the optionally substituted $C_3$-$C_6$ cycloalkyl comprises at least one double bond. In some embodiments, the optionally substituted $C_3$-$C_6$ cycloalkyl is a cyclopentene.

In some embodiments, $R^{1a}$, $R^{1b}$, $R^{1c}$, $R^{1d}$, and $R^{1e}$ are each hydrogen.

In some embodiments, n is 1-10. In some embodiments, n is 1-5. In some embodiments, n is 1.

In some embodiments, the polymer precursor is a compound selected from the group consisting of:

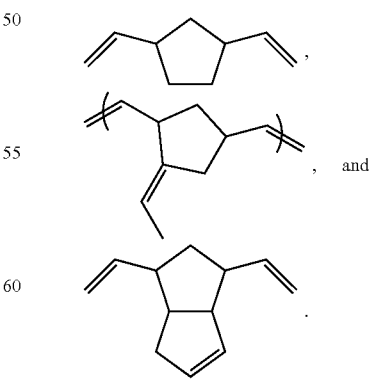

In some embodiments, the polymer precursor is a compound having a structure of Formula (IV):

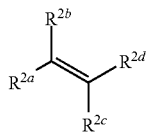

Formula (IV)

wherein:
R$^{2a}$, R$^{2b}$, R$^{2c}$, and R$^{2d}$ are each independently hydrogen, optionally substituted alkyl, or R$^{2a}$ and R$^{2c}$ are taken together with the atoms to which they are attached to form an optionally substituted cycloalkyl.

In some embodiments, R$^{2a}$ and R$^{2d}$ are each independently optionally substituted alkyl and R$^{2b}$ and R$^{2c}$ are each hydrogen. In some embodiments, R$^{2a}$ and R$^{2d}$ are each independently optionally substituted alkyl comprising one or more optionally substituted unsaturated bond. In some embodiments, R$^{2a}$ and R$^{2d}$ are each independently C$_1$-C$_{20}$ alkyl and R$^{2b}$ and R$^{2c}$ are each hydrogen. In some embodiments, R$^{2a}$ and R$^{2d}$ are each independently C$_1$-C$_{10}$ alkyl and R$^{2b}$ and R$^{2c}$ are each hydrogen. In some embodiments, R$^{2a}$ and R$^{2d}$ are each independently C$_1$-C$_6$ alkyl and R$^{2b}$ and R$^{2c}$ are each hydrogen.

In some embodiments, R$^{2a}$ and R$^{2c}$ are taken together with the atoms to which they are attached to form an optionally substituted cycloalkyl and R$^{2b}$ and R$^{2d}$ are each hydrogen. In some embodiments, the optionally substituted cycloalkyl comprises one or more optionally substituted unsaturated bond. In some embodiments, R$^{2a}$ and R$^{2c}$ are taken together with the atoms to which they are attached to form an C$_4$-C$_{20}$ cycloalkyl and R$^{2b}$ and R$^{2d}$ are each hydrogen. In some embodiments, R$^{2a}$ and R$^{2c}$ are taken together with the atoms to which they are attached to form an C$_4$-C$_{12}$ cycloalkyl and R$^{2b}$ and R$^{2d}$ are each hydrogen. In some embodiments, R$^{2a}$ and R$^{2c}$ are taken together with the atoms to which they are attached to form an C$_4$-C$_8$ cycloalkyl and R$^{2b}$ and R$^{2d}$ are each hydrogen.

In some embodiments, the at least one polymer precursor is a compound selected from the group consisting of:

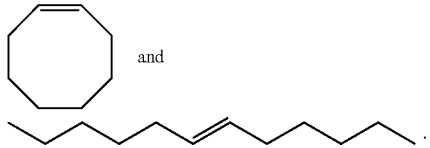

In some embodiments, the polymer precursor is a compound having a structure of Formula (V):

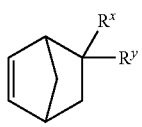

Formula (V)

wherein:
R$^x$ and R$^y$ are each independently hydrogen, optionally substituted alkyl (e.g., optionally substituted with one or more group, each group independently selected from the group consisting of hydroxyl, optionally substituted alkyl, optionally substituted heteroalkyl (e.g., amide), and optionally substituted alkoxy), or R$^x$ and R$^y$ are taken together with the atoms to which they are attached to form an optionally substituted alkenyl.

In some embodiments, R$^x$ and R$^y$ are each hydrogen.
In some embodiments, R$^x$ and R$^y$ are each independently hydrogen or optionally substituted alkyl. In some embodiments, R$^x$ and R$^y$ are each independently hydrogen or unsubstituted alkyl. In some embodiments, R$^x$ is hydrogen and R$^y$ is C$_1$-C$_{20}$ alkyl. In some embodiments, R$^x$ is hydrogen and R$^y$ is C$_1$-C$_{10}$ alkyl. In some embodiments, R$^x$ is hydrogen and R$^y$ is C$_1$-C$_5$ alkyl.

In some embodiments, R$^x$ and R$^y$ are each independently hydrogen or alkyl substituted with one or more group, each group independently selected from the group consisting of hydroxyl, optionally substituted alkyl, optionally substituted heteroalkyl (e.g., amide), and optionally substituted alkoxy. In some embodiments, R$^x$ is hydrogen and R$^y$ is alkyl substituted with one or more group, each group independently selected from the group consisting of hydroxyl, optionally substituted alkyl, optionally substituted heteroalkyl (e.g., amide), and optionally substituted alkoxy. In some embodiments, R$^x$ is hydrogen and R$^y$ is alkyl substituted with hydroxyl. In some embodiments, the optionally substituted alkyl, optionally substituted heteroalkyl (e.g., amide), or optionally substituted alkoxy is a linker (e.g., a polymer).

In some embodiments, the polymer precursor is a compound having a structure of Formula (V-A):

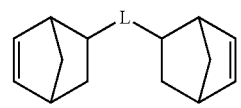

Formula (V-A)

wherein:
L is a linker (e.g., a polymer).

In some embodiments, the polymer precursor is a compound selected from the group consisting of:

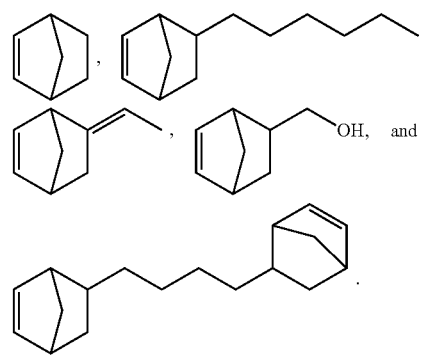

In some embodiments, the polymer precursor is a compound having a structure of Formula (VI):

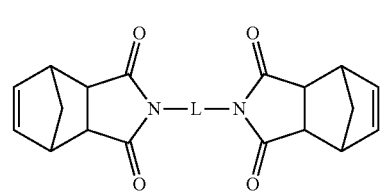

Formula (VI)

wherein:

L is a linker (e.g., a polymer).

In some embodiments, L is a polymer. In some embodiments, L is optionally substituted alkylene (e.g., $C_1$-$C_{20}$ alkylene), optionally substituted alkoxy (e.g., PEG), optionally substituted siloxane (e.g., PDMS), or optionally substituted heteroalkyl (e.g., polyamide). In some embodiments, L is optionally $C_1$-$C_{20}$ alkylene. In some embodiments, L is optionally $C_1$-$C_{10}$ alkylene. In some embodiments, L is optionally $C_1$-$C_5$ alkylene.

In some embodiments, the polymer precursor is a compound selected from the group consisting of:

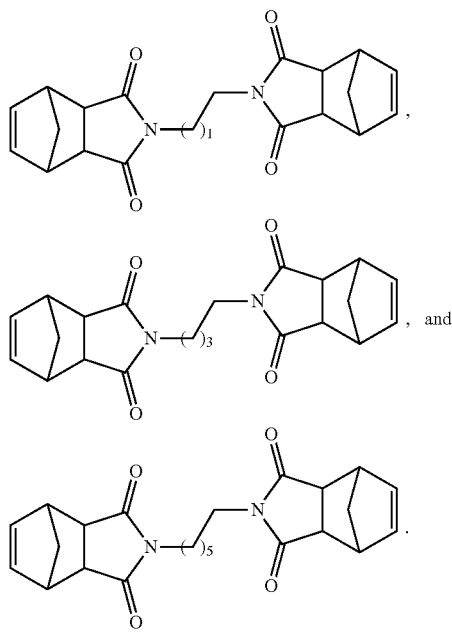

In some embodiments, the polymer precursor is a compound having a structure of Formula (VII):

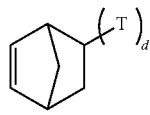

Formula (VII)

wherein:
T is a (central) point of attachment (e.g., optionally substituted alkyl (e.g., alkyl substituted with one or more group, each group independently selected from the group consisting of alkyl and alkoxy substituted with oxo), optionally substituted heteroalkyl (e.g., polyamide or polyester), optionally substituted alkoxy (e.g., PEG) or wherein the (central) point of attachment comprises one or more silicon (Si) (e.g., optionally substituted siloxane (e.g., PDMS))); and
d is an integer from 1-10.

In some embodiments, T (e.g., the central point of attachment) is a carbon atom.

In some embodiments, T is optionally substituted alkyl. In some embodiments, T is alkyl substituted with one or more group, each group independently selected from the group consisting of alkyl and alkoxy substituted with oxo. In some embodiments, T is alkyl substituted alkyl and alkoxy substituted with oxo. In some embodiments, T is optionally substituted heteroalkyl. In some embodiments, the optionally substituted heteroalkyl is a polyamide or a polyester. In some embodiments, the heteroalkyl is substituted with alkyl (e.g., $C_1$-$C_6$ alkyl). In some embodiments, the heteroalkyl is substituted with methyl. In some embodiments, T is optionally substituted alkoxy (e.g., PEG). In some embodiments, T is alkoxy substituted with alkyl (e.g., $C_1$-$C_6$ alkyl) and oxo.

In some embodiments, T (e.g., the central point of attachment) is a silicon atom. In some embodiments, T comprises one or more silicon atom (Si). In some embodiments, T comprises 1-15 silicon atom(s). In some embodiments, T comprises 1-10 silicon atom(s). In some embodiments, T comprises 10 silicon atoms. In some embodiments, T comprises one or more silicon atom (Si) coupled to one or more oxygen atom (O). In some embodiments, T comprises one or more silicon atom (Si) coupled to one or more oxygen atom (O) and one or more alkyl (e.g., $C_1$-$C_6$alkyl). In some embodiments, T comprises one or more silicon atom (Si) coupled to one or more oxygen atom (O) and one or more isopropyl. In some embodiments, T is optionally substituted siloxane (e.g., PDMS).

In some embodiments, the polymer precursor is:

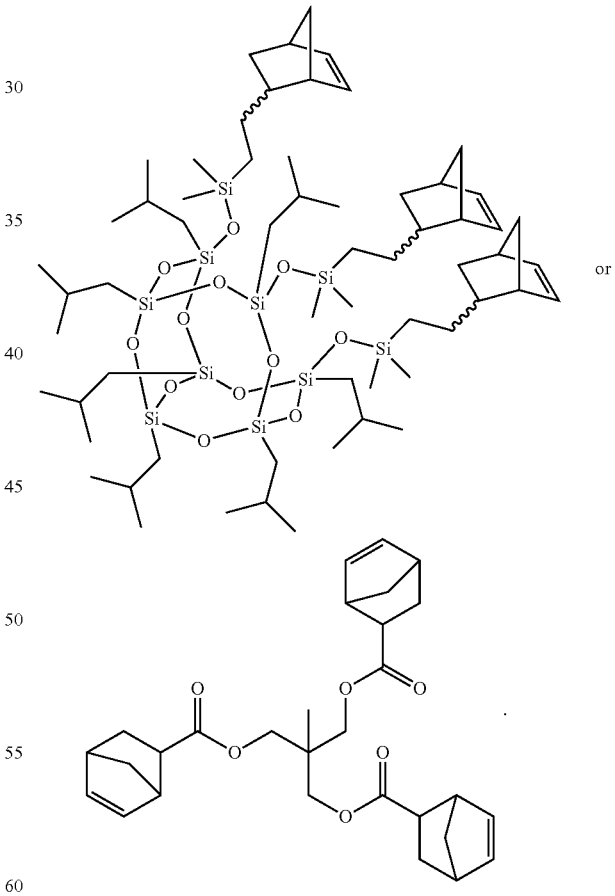

In some embodiments, a mixture described herein comprises any polymer precursor described in any of International Publication Number WO 2014/055720, U.S. Pat. No. 9,207,532, European Patent Number 2,903,996, International Publication Number WO 2015/065649, U.S. Patent Publication Number 2015/118188, European Patent Publication Number 3,063,592, International Publication Number WO 2018/045132, U.S. Patent Publication Number 2018/067393, U.S. Patent Publication Number 2020/183276, European Patent Publication Number 3,507,007, International Publication Number WO 2020/006345, Photolithographic Olefin Metathesis Polymerization, *J. Am. Chem. Soc.* 2013, 135, 16817-16820, Visible-Light-Controlled Ruthenium-Catalyzed Olefin Metathesis, *J. Am. Chem. Soc.* 2019, 141, 17, 6791-6796, A Tandem Approach to Photoactivated Olefin Metathesis: Combining a Photoacid Generator with an Acid Activated Catalyst, *J. Am. Chem. Soc.* 2009, 131, 6, 2038-2039, Metal-Free Ring-Opening Metathesis Polymerization, *J. Am. Chem. Soc.* 2015, 137, 1400-1403, JOURNAL OF POLYMER SCIENCE, PART A: POLYMER CHEMISTRY 2019, 57, 1791-17, each of which is incorporated herein by reference, in their entirety, in particular for the compounds provided therein.

The polymer precursor can be present (e.g., combined) in a mixture provided herein at a concentration of at least 0.1% by weight, 1% by weight, 10% by weight, 20% by weight, 30% by weight, 40% by weight, 50% by weight, 60% by weight, 70% by weight, 80% by weight, 90% by weight, 99% by weight, 99.9% by weight, 99.99% by weight, 99.999% by weight, 99.9999% by weight, or more. The polymer precursor can be present (e.g., combined) in a mixture provided herein at a concentration of at most 99.9999% by weight, 99.999% by weight, 99.99% by weight, 99.9% by weight, 99% by weight, 90% by weight, 80% by weight, 70% by weight, 60% by weight, 50% by weight, 40% by weight, 30% by weight, 20% by weight, 10% by weight, 1% by weight, 0.1% by weight, or less. The polymer precursor can be present (e.g., combined) in a mixture provided herein at a concentration within a range defined by any two of the preceding values. The polymer precursor can be present (e.g., combined) in a mixture provided herein at a concentration from 0.1% to 99.9999%. The polymer precursor can be present (e.g., combined) in a mixture provided herein at a concentration from 50% to 99.9%.

Additives:

A mixture provided herein may comprise one or more additive. The additive may modify at least one property, feature, or characteristic of the 3D object. The additive may modify the modulus, toughness, impact strength, color, UV-stability, ductility, glass transition temperature, weather resistance, flammability or surface energy of the 3D object. The additive may modify at least one property, feature, or characteristic of the photopolymer. The additive may modify the photomodulus coefficient, green strength, pot life, shelf life, printing accuracy, critical exposure, penetration depth, print speed or optimal print environment or temperature of the photopolymer (e.g., 3D object).

The additive may be selected from the group consisting of an antioxidant (e.g., a primary antioxidant or a secondary antioxidant), a filler, an optical brightener, an ultraviolet (UV) absorber, a pigment, a dye, a photoredox agent, an oxygen scavenger, a flame retardant, an impact modifier, a particle, a filler, a fiber, a nanoparticle, a plasticizer, a solvent, an oil, a wax, a vulcanizing agent, a crosslinker (e.g., a secondary crosslinker (e.g., a thiol or a peroxide)), hindered amine light stabilizer (HALS), a polymerization inhibitor (e.g. a phosphine, phosphite, amine, pyridine, bipyridine, phenanthroline, chelating agent, thiol, vinyl ether), a shelf-life stabilizer, a chain-transfer agent, and a sizing agent (e.g. functionality to connect organic and inorganic phases).

In some embodiments, the additive is a coumarin (e.g., a derivative thereof), an alpha hydroxy ketone, or a phosphine oxide.

In some embodiments, the additive is a compound selected from the group consisting of:

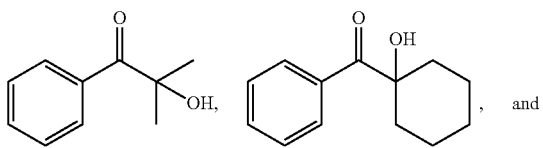

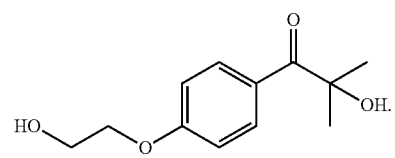

In some embodiments, the additive is a compound selected from the group consisting of:

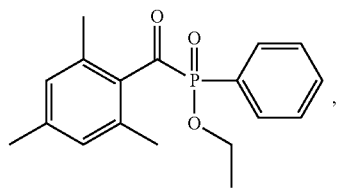

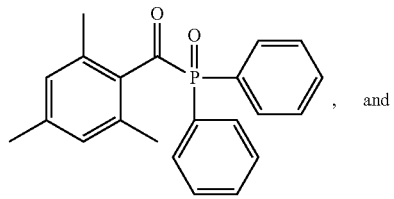

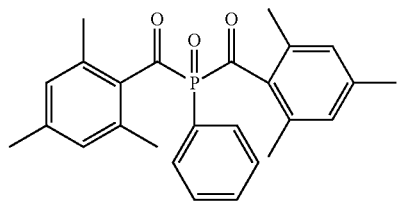

In some embodiments, the additive is a compound selected from the group consisting of:

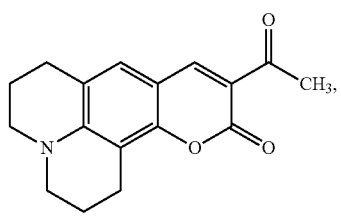

-continued

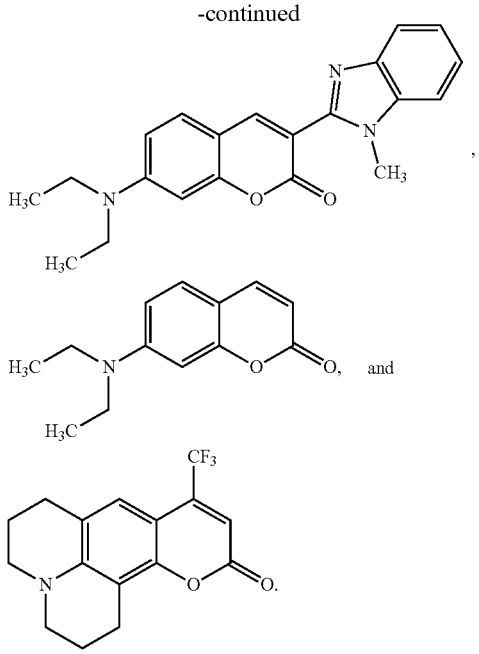

and

The additive can be present (e.g., combined) in a mixture provided herein at a concentration of at least 0.1 parts per million (ppm) (e.g., 0.00001% by weight), 1 ppm (e.g., 0.0001% by weight), 10 ppm (e.g., 0.001% by weight), 100 ppm (e.g., 0.01% by weight), 1,000 ppm (e.g., 0.1% by weight), 10,000 ppm (e.g., 1% by weight), 100,000 ppm (e.g., 10% by weight), 200,000 ppm (e.g., 20% by weight), or more. The additive can be present (e.g., combined) in a mixture provided herein at a concentration of at most 200,000 ppm (e.g., 20% by weight), 100,000 ppm (e.g., 10% by weight), 10,000 ppm (e.g., 1% by weight), 1,000 ppm (e.g., 0.1% by weight), 100 ppm (e.g., 0.01% by weight), 10 ppm (e.g., 0.001% by weight), 1 ppm (e.g., 0.0001% by weight), 0.1 ppm (e.g., 0.00001% by weight), or less. The additive can be present (e.g., combined) in a mixture provided herein at a concentration within a range defined any two of the preceding values. The additive can be present (e.g., combined) in a mixture provided herein at a concentration from about 0.1 ppm (e.g., 0.00001% by weight) to about 200,000 ppm (e.g., 20% by weight). The additive may be present in the mixture at a concentration from about 1,000 ppm (e.g., 0.1% by weight) to about 10,000 ppm (e.g., 1% by weight).

In some embodiments, a mixture described herein comprises any compound or composition (e.g., catalyst, initiator, polymer precursor, etc.) described in any of International Publication Number WO 2014/055720, U.S. Pat. No. 9,207,532, European Patent Number 2,903,996, International Publication Number WO 2015/065649, U.S. Patent Publication Number 2015/118188, European Patent Publication Number 3,063,592, International Publication Number WO 2018/045132, U.S. Patent Publication Number 2018/067393, U.S. Patent Publication Number 2020/183276, European Patent Publication Number 3,507,007, International Publication Number WO 2020/006345, Photolithographic Olefin Metathesis Polymerization, *J. Am. Chem. Soc.* 2013, 135, 16817-16820, Visible-Light-Controlled Ruthenium-Catalyzed Olefin Metathesis, *J. Am. Chem. Soc.* 2019, 141, 17, 6791-6796, A Tandem Approach to Photoactivated Olefin Metathesis: Combining a Photoacid Generator with an Acid Activated Catalyst, *J. Am. Chem. Soc.* 2009, 131, 6, 2038-2039, Metal-Free Ring-Opening Metathesis Polymerization, *J. Am. Chem. Soc.* 2015, 137, 1400-1403, JOURNAL OF POLYMER SCIENCE, PART A: POLYMER CHEMISTRY 2019, 57, 1791-17, each of which is incorporated herein by reference, in its entirety, in particular for the compounds provided therein.

Computer Systems

Figure 2:
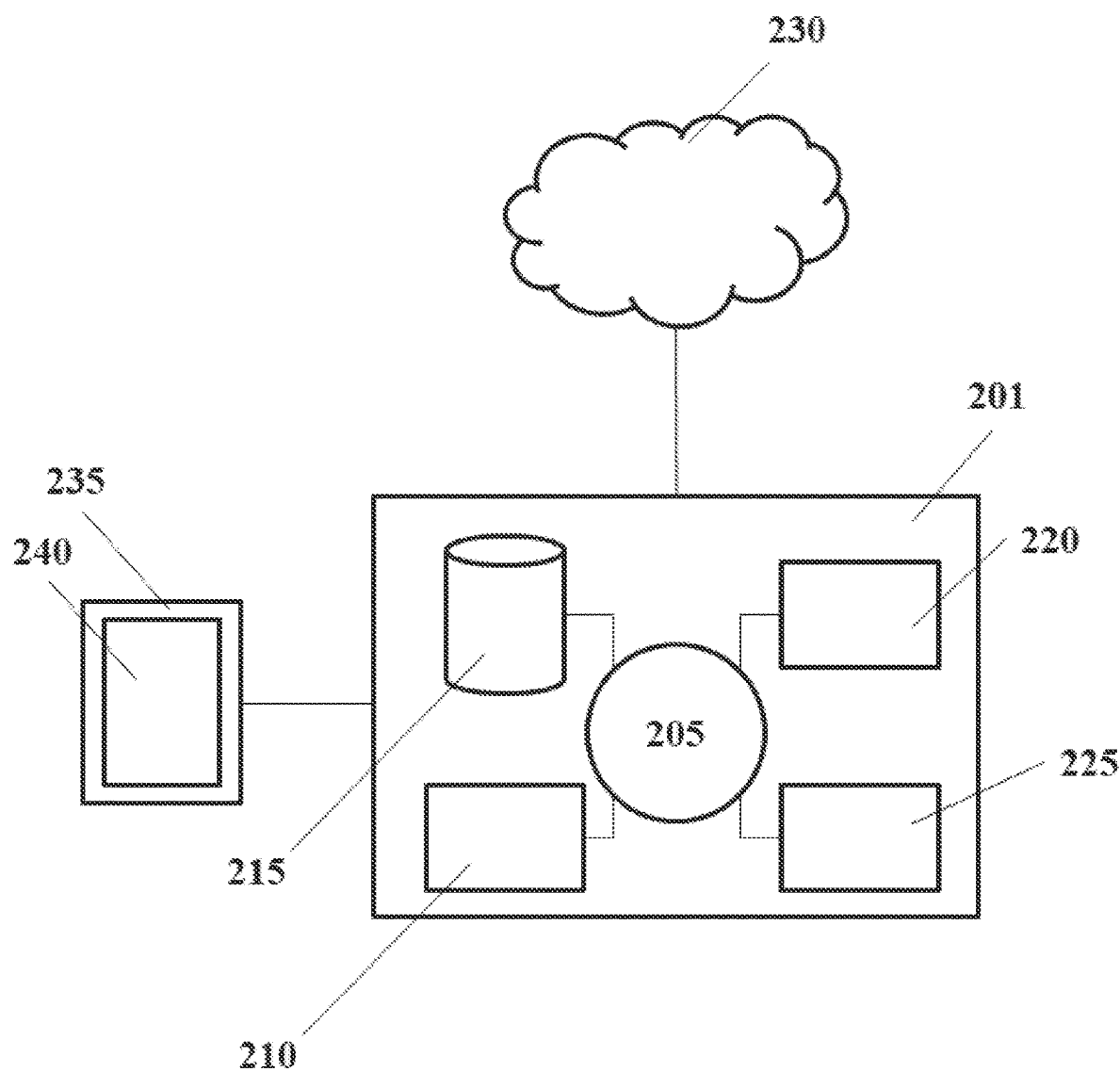
FIG. 2 shows a computer system that is programmed or otherwise configured to implement methods provided herein.

The present disclosure provides computer systems that are programmed to implement methods of the disclosure. FIG. 2 shows a computer system 201 that is programmed or otherwise configured to process a three-dimensional (3D) object, such as, for example, a dental product or an orthodontic product. The computer system 201 can regulate various aspects of the methods and compositions of the present disclosure, such as, for example, reactivity, viscosity, latent catalyst loading, PAG loading, PAH loading, sensitizer loading, stabilizer loading, solvent loading, additive loading, oxygen concentration, exposure doses, irradiances. The computer system 201 can be an electronic device of a user or a computer system that is remotely located with respect to the electronic device. The electronic device can be a mobile electronic device.

The computer system 201 includes a central processing unit (CPU, also "processor" and "computer processor" herein) 205, which can be a single core or multi core processor, or a plurality of processors for parallel processing. The computer system 201 also includes memory or memory location 210 (e.g., random-access memory, read-only memory, flash memory), electronic storage unit 215 (e.g., hard disk), communication interface 220 (e.g., network adapter) for communicating with one or more other systems, and peripheral devices 225, such as cache, other memory, data storage and/or electronic display adapters. The memory 210, storage unit 215, interface 220 and peripheral devices 225 are in communication with the CPU 205 through a communication bus (solid lines), such as a motherboard. The storage unit 215 can be a data storage unit (or data repository) for storing data. The computer system 201 can be operatively coupled to a computer network ("network") 230 with the aid of the communication interface 220. The network 230 can be the Internet, an internet and/or extranet, or an intranet and/or extranet that is in communication with the Internet. The network 230 in some cases is a telecommunication and/or data network. The network 230 can include one or more computer servers, which can enable distributed computing, such as cloud computing. The network 230, in some cases with the aid of the computer system 201, can implement a peer-to-peer network, which may enable devices coupled to the computer system 201 to behave as a client or a server.

The CPU 205 can execute a sequence of machine-readable instructions, which can be embodied in a program or software. The instructions may be stored in a memory location, such as the memory 210. The instructions can be directed to the CPU 205, which can subsequently program or otherwise configure the CPU 205 to implement methods of the present disclosure. Examples of operations performed by the CPU 205 can include fetch, decode, execute, and writeback. The CPU 205 can be part of a circuit, such as an integrated circuit. One or more other components of the system 201 can be included in the circuit. In some cases, the circuit is an application specific integrated circuit (ASIC).

The storage unit 215 can store files, such as drivers, libraries and saved programs. The storage unit 215 can store user data, e.g., user preferences and user programs. The computer system 201 in some cases can include one or more additional data storage units that are external to the computer system 201, such as located on a remote server that is in communication with the computer system 201 through an intranet or the Internet.

The computer system 201 can communicate with one or more remote computer systems through the network 230. For instance, the computer system 201 can communicate with a remote computer system of a user (e.g., mobile electronic device). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 201 via the network 230.

Methods as described herein can be implemented by way of machine (e.g., computer processor) executable code stored on an electronic storage location of the computer system 201, such as, for example, on the memory 210 or electronic storage unit 215. The machine executable or machine-readable code can be provided in the form of software. During use, the code can be executed by the processor 205. In some cases, the code can be retrieved from the storage unit 215 and stored on the memory 210 for ready access by the processor 205. In some situations, the electronic storage unit 215 can be precluded, and machine-executable instructions are stored on memory 210.

The code can be pre-compiled and configured for use with a machine having a processer adapted to execute the code or can be compiled during runtime. The code can be supplied in a programming language that can be selected to enable the code to execute in a pre-compiled or as-compiled fashion.

Aspects of the systems and methods provided herein, such as the computer system 201, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution. The computer system 201 can include or be in communication with an electronic display 235 that comprises a user interface (UI) 240 for providing, for example, information related to compositions of and methods for processing photopolymers. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 205. The algorithm can, for example, provide the design of a three-dimensional (3D) object (e.g., a dental product or an orthodontic product), instruct the printing of a 3D object (e.g., a dental product or an orthodontic product), modify a printing path for a 3D object (e.g., a dental product or an orthodontic product), or a combination thereof.

LIST OF EMBODIMENTS

The following list of embodiments of the invention are to be considered as disclosing various features of the invention, which features can be considered to be specific to the particular embodiment under which they are discussed, or which are combinable with the various other features as listed in other embodiments. Thus, simply because a feature is discussed under one particular embodiment does not necessarily limit the use of that feature to that embodiment.

Embodiment 1. A method for generating a dental product or an orthodontic product, comprising: (a) providing a mixture comprising (i) a latent ruthenium (Ru) complex; (ii) an initiator; (iii) a sensitizer that sensitizes said initiator; and (iv) at least one polymer precursor; and (b) exposing said mixture to electromagnetic radiation to activate said initiator, wherein upon activation, said initiator reacts with said latent Ru complex to generate an activated Ru complex, which activated Ru complex reacts with said at least one polymer precursor to generate at least a portion of said dental product or said orthodontic product.

Embodiment 2. The method of embodiment 1, wherein said dental product or said orthodontic product is generated using additive manufacturing.

Embodiment 3. The method of embodiment 1 or 2, wherein said sensitizer is configured to transfer or disperse the energy of electromagnetic radiation (e.g., electromagnetic radiation having a wavelength from 300 nanometers (nm) to 3,000 nm (e.g., 350 nm to 465 nm)).

Embodiment 4. The method of any one of embodiments 1 to 3, wherein said mixture is activated at a wavelength from 200-800 nanometers (nm) (e.g., 350 nm to 465 nm) at a temperature from 0° C. to 100° C. (e.g., 20° C. to 50° C.) for 1 nanosecond (ns) to 1 week (e.g., 1 millisecond (ms) to 1 hour).

Embodiment 5. The method of any one of embodiments 1 to 4, further comprising cleaning said dental product or said orthodontic product.

Embodiment 6. The method of any one of embodiments 1 to 5, wherein said dental product or said orthodontic product is cleaned using a solvent, agitation, sonication, stirring, air drying, air knives, automated washing, or any combination thereof.

Embodiment 7. The method of any one of embodiments 1 to 6, wherein a surface of said dental product or said orthodontic product is smoothed, brightened, coated, sealed, sterilized, or a combination thereof.

Embodiment 8. The method of any one of embodiments 1 to 7, further comprising post-curing said dental product or said orthodontic product.

Embodiment 9. The method of any one of embodiments 1 to 8, wherein said dental product or said orthodontic product is post-cured using ultraviolet radiation, visible (light) radiation, convection heating, conduction heating, radiation heating, or any combination thereof.

Embodiment 10. A method for generating a dental product or an orthodontic product, comprising:
a. providing a mixture comprising (i) a latent ruthenium (Ru) complex; (ii) an initiator; and (iii) at least one polymer precursor, wherein said latent Ru complex is present at a concentration from 0.1 parts per million (ppm) by weight to 1% by weight and said initiator is present at a concentration from 0.1 parts per million (ppm) by weight to 10% by weight; and
b. exposing said mixture to electromagnetic radiation to activate said initiator, wherein upon activation, said initiator reacts with said latent Ru complex to generate an activated Ru complex, which activated Ru complex reacts with said at least one polymer precursor to generate at least a portion of said dental product or said orthodontic product.

Embodiment 11. A method for generating a dental product or an orthodontic product, comprising:
a. providing mixture comprising (i) a latent ruthenium (Ru) complex; (ii) an initiator; and (iii) at least one polymer precursor, wherein said latent Ru complex and said initiator are present at a ratio of said Ru complex to said initiator at a ratio by moles from 0.01:1.0 to 10:1.0; and
b. exposing said mixture to electromagnetic radiation to activate said initiator, wherein upon activation, said initiator reacts with said latent Ru complex to generate an activated Ru complex, which activated Ru complex reacts with said at least one polymer precursor to generate at least a portion of said dental product or said orthodontic product.

Embodiment 12. A method for generating a dental product or an orthodontic product, comprising:
a. providing mixture comprising (i) a latent ruthenium (Ru) complex; (ii) an initiator that is an iodonium salt or a sulfonium salt; and (iii) at least one polymer precursor; and
b. exposing said mixture to electromagnetic radiation to activate said initiator, wherein upon activation, said initiator reacts with said latent Ru complex to generate an activated Ru complex, which activated Ru complex reacts with said at least one polymer precursor to generate at least a portion of said dental product or said orthodontic product.

Embodiment 13. A method for printing a dental product or an orthodontic product, comprising:
a. providing a resin comprising (i) a latent ruthenium (Ru) complex, (ii) an initiator, and (iii) at least one polymer precursor; and
b. exposing said resin to electromagnetic radiation to activate said initiator, wherein upon activation, said initiator reacts with said latent Ru complex to generate an activated Ru complex, which activated Ru complex reacts with said polymer precursor to print at least portion of said dental product or said orthodontic product.

Embodiment 14. The method of any one of embodiments 1 to 13, further comprising printing said dental product or said orthodontic product adjacent to a support.

Embodiment 15. The method of any one of embodiments 1 to 14, wherein said dental product or said orthodontic product is removed from said support using robot-assistance, sonication, vibration, chemical swelling, chemical etching, laser ablation, laser cutting, blade cutting, or any combination thereof.

Embodiment 16. A dental product or an orthodontic product, comprising a body comprising a cyclic olefin polymer.

Embodiment 17. The dental product or the orthodontic product of embodiment 16, wherein said dental product or said orthodontic product is selected from the group consisting of an orthodontic aligner, a mouth guard, a surgical guide, a night guard, a splint, a denture, a prosthodontic, a dental prosthetic, an extra-oral appliance, a crown, a grill, dental jewelry, a brace, a surgical stent, a bruxism device (e.g., a bruxism guard), a sleep apnea device, a provisional or temporary restoration product (e.g., a temporary crown or a temporary bridge).

Embodiment 18. The dental product or the orthodontic product of any one of embodiments 16 or 17, further comprising an additive.

Embodiment 19. The dental product or the orthodontic product of any one of embodiments 16 to 18, wherein said additive is selected from the group consisting of a pigment (e.g., a white pigment), a dye (e.g., a fluorophore), an optical brightener, a fluorescent whitening agent, a bluing agent, a decorative particle, a nanoparticle, a dielectric mirror, a photonic crystal, a non-linear optical media, a white pigments, an impact modifier, and a plasticizer.

Embodiment 20. The dental product or the orthodontic product of any one of embodiments 16 to 19, wherein said additive modifies at least one property or characteristic of said dental product or said orthodontic product.

Embodiment 21. The dental product or the orthodontic product of any one of embodiments 16 to 20, wherein said dental product or said orthodontic product comprises at least one sub-component, a component geometry, or any combination thereof.

Embodiment 22. The dental product or the orthodontic product of any one of embodiments 16 to 21, wherein said at least one sub-component or said component geometry is selected from the group consisting of a void, a lattice structure, a triple periodic minimal surface, a personalized geometry, a stylized geometry, an aesthetic geometry, a digitally-defined surface texture, a ring, a tori, a tube, a fluidic channel, a grip, an anchor, a connector, a hook, a ratchet, a valve, and a clip.

Embodiment 23. The dental product or the orthodontic product of any one of embodiments 16 to 21, wherein said component geometry includes at least one topology.

Embodiment 24. The dental product or the orthodontic product of any one of embodiments 16 to 23, wherein said at least one topology is configured to move one or more tooth (e.g., move, rotate, align, or any combination thereof) of an individual wearing said dental product or said orthodontic product.

Embodiment 25. The dental product or the orthodontic product of any one of embodiments 16 to 24, having an elongation at break ductility from 2-500%.

Embodiment 26. The dental product or the orthodontic product of any one of embodiments 16 to 25, having a tear strength from 1 to 1000 kiloNewtons per meter (kN/m).

Embodiment 27. The dental product or the orthodontic product of any one of embodiments 16 to 26, having an impact strength from 1 Joules per meter (J/m) to 10,000 J/m (e.g., 1 J/m to 1,000 J/m).

Embodiment 28. The dental product or the orthodontic product of any one of embodiments 16 to 27, having a strain at yield from 0.1% to 10,000%.

Embodiment 29. The dental product or the orthodontic product of any one of embodiments 16 to 28, having a strain at break from 1 percent (%) to 10,000%.

Embodiment 30. The dental product or the orthodontic product of any one of embodiments 16 to 29, having a water absorption (e.g., at 24 hours) from about 0.1 parts per billion (ppb) to 50 wt %.

Embodiment 31. The dental product or the orthodontic product of any one of embodiments 16 to 30, having a glass transition temperature ($T_g$) from −50 degrees Celsius (° C.) to 250° C. (e.g., 100° C. to 200° C.).

Embodiment 32. The dental product or the orthodontic product of any one of embodiments 16 to 31, having a heat-deflection temperature (HDT) from 0 degrees Celsius (° C.) to 300° C. (e.g., 50° C. to 200° C.).

EXAMPLES

Example 1: Photopolymerization of Dicyclopentadiene and Tricyclopentadiene

Bis[1,3-bis(2,4,6-trimethylphenyl)-2-imidazolidinylidene]dichloro(benzylidene)ruthenium(II), which will be referred to as $(SIMes)_2Ru(benzylidene)Cl_2$, was purchased from Umicore and used as received. Bis(4-tert-butylphenyl)iodonium hexafluorophosphate, was purchased from Sigma Aldrich and used as received. 2-Isopropylthioxanthone (ITX) was purchased from Lambson and used as received.

A suspension of 0.9 mg/mL $(SIMes)_2Ru(benzylidene)Cl_2$, 1.75 mg/mL Bis(4-tert-butylphenyl)iodonium hexafluorophosphate, and 1.75 mg/mL ITX was prepared in a liquid mixture of dicyclopentadiene and 6 wt % tricyclopentadiene. The resulting suspension is the example photopolymer.

Figure 3:
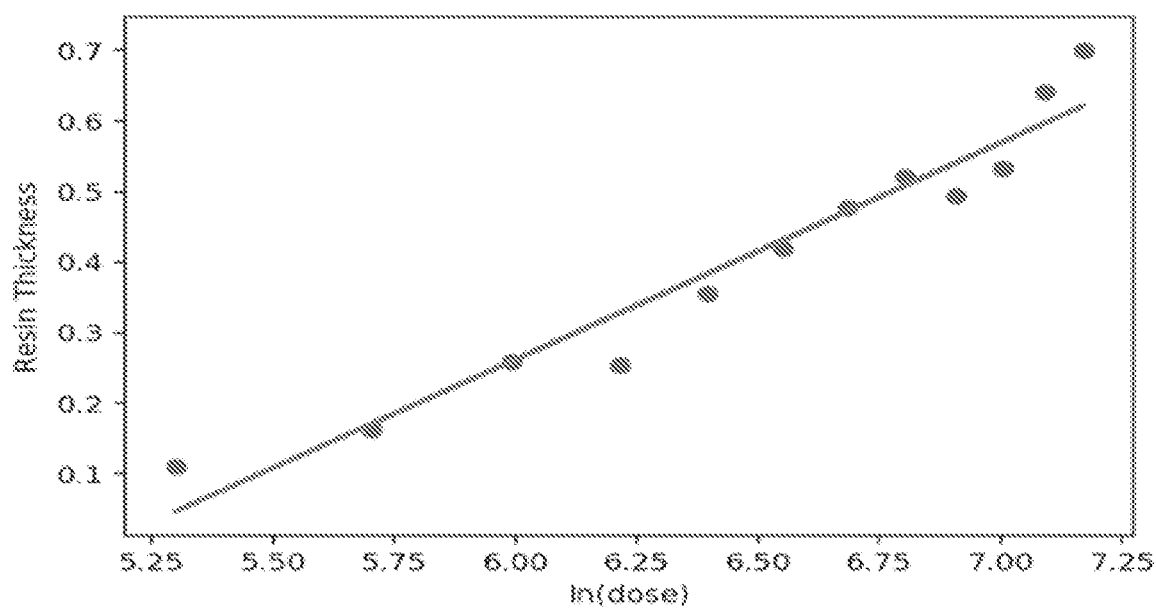
FIG. 3 illustrates a photopolymer working curve for the photopolymerization behavior of a photopolymer mixture comprising bis[1,3-bis(2,4,6-trimethylphenyl)-2-imidazolidinylidene]dichloro(benzylidene)ruthenium(II) ((SIMes)$_2$Ru(benzylidene)Cl$_2$), bis(4-tert-butylphenyl)iodonium hexafluorophosphate, 2-isopropylthioxanthone (ITX), dicyclopentadiene, and tricyclopentadiene.

A photopolymer working curve was used to demonstrate the photopolymerization behavior of this example photopolymer mixture (FIG. 3). The working curve is a standard practice in the field of photopolymerization, described extensively by Paul F. Jacobs in *Rapid Prototyping & Manufacturing: Fundamentals of Stereolithography*. The working curve was performed using 385 nm light on a stereolithographic 3D printer containing a DLP projector, at 40° C., in a nitrogen-filled glove box containing approximately 1% $O_2$. The critical exposure (Ec) was determined to be 172 mJ/cm2. The penetration depth (Dp) was determined to be 307 microns.

In the absence of the Bis(4-tert-butylphenyl)iodonium hexafluorophosphate PAG, the corresponding suspension is not readily photo-curable, even at high doses of light (for example >2 J/cm$_2$). This suggests that the ITX is not directly sensitizing the $(SIMes)_2Ru(benzylidene)Cl_2$. In the absence of sensitizer, the corresponding suspension is not readily photo-curable at 385 nm but can be cured at higher energy wavelengths of light.

Example 2: Printing and Properties

Photoacid generator (PAG) compounds including Bis(4-tert-butylphenyl)iodonium triflate (PAG-A), and Bis(4-tert-butylphenyl)iodonium hexaflurophosphate (PAG-B) were purchased from Sigma Aldrich and used as received. 2-Isopropylthioxanthone (ITX) was purchased from Lambson and used as received. A solution of dicyclopentadiene containing approximately 6 weight percent wt % tricyclopentadiene (DCPD solution), was purchased from Cymetech and used as received.

Figure 4A:
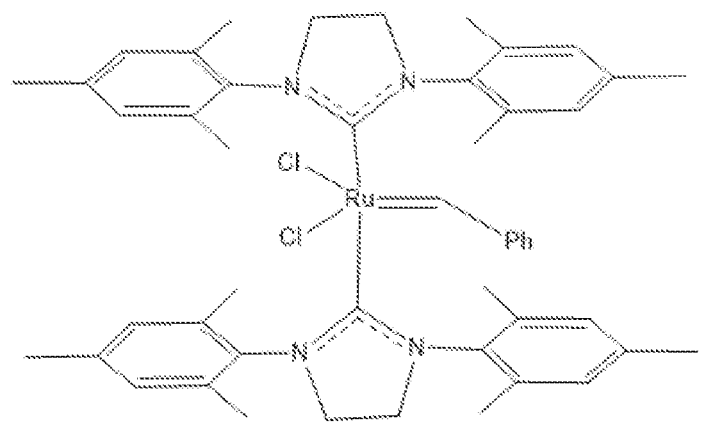
FIG. 4A illustrates a chemical structure of Catalyst A.
Figure 4B:
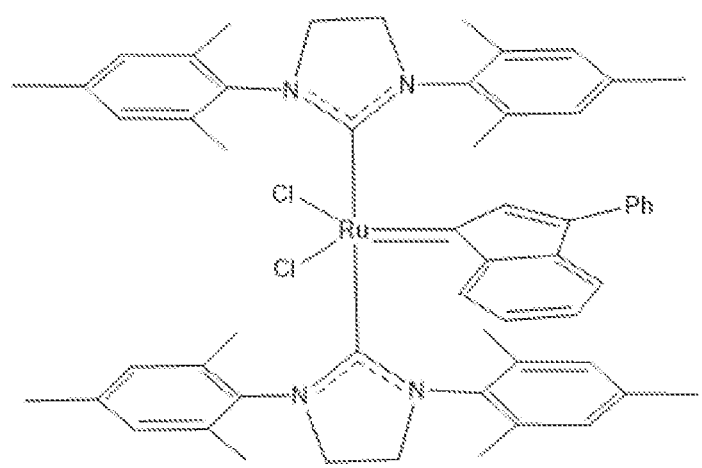
FIG. 4B illustrates a chemical structure of Catalyst B.
Figure 4C:
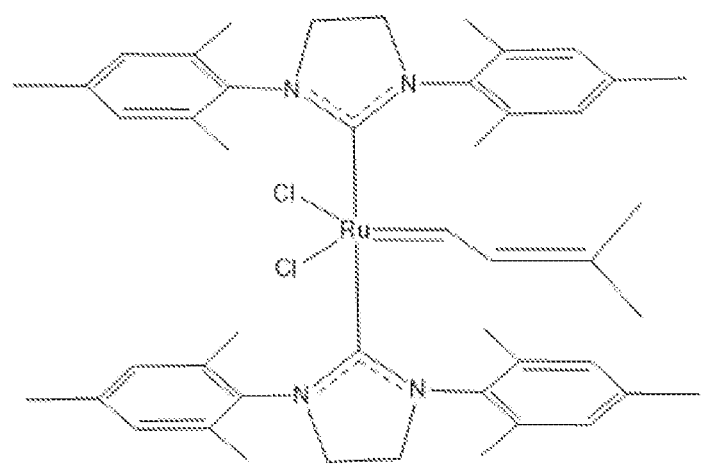
FIG. 4C illustrates a chemical structure of Catalyst C.
Figure 4D:
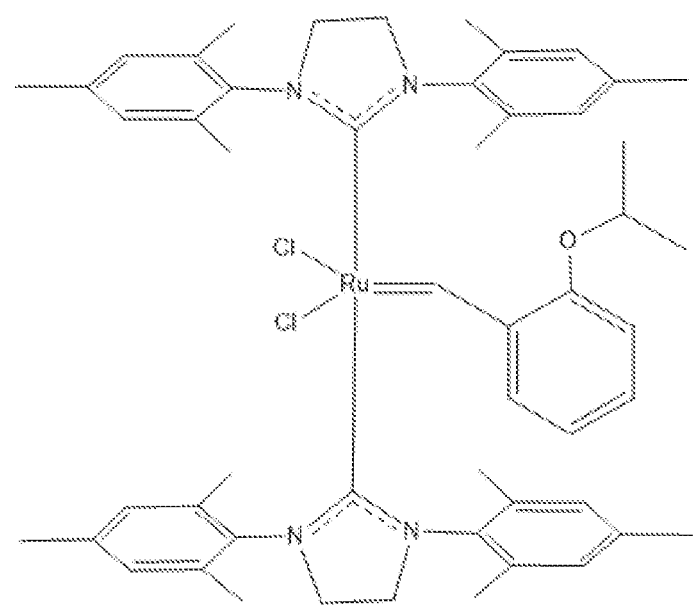
FIG. 4D illustrates a chemical structure of Catalyst D.

Bis[1,3-bis(2,4,6-trimethylphenyl)-2-imidazolidinylidene]dichloro(benzylidene)ruthenium(II) (Catalyst A; FIG. 4A), Bis[1,3-bis(2,4,6-trimethylphenyl)-2-imidazolidinylidene]dichloro(3-phenyl-1H-inden-1-ylidene)ruthenium (II) (Catalyst B; FIG. 4B), Bis[1,3-bis(2,4,6-trimethylphenyl)-2-imidazolidinylidene]dichloro(buteneylidene)ruthenium(II) (Catalyst C; FIG. 4C), and Bis[1,3-bis(2,4,6-trimethylphenyl)-2-imidazolidinylidene]dichloro(o-isopropoxybenzylidene)ruthenium(II) (Catalyst D; FIG. 4D), were purchased from Umicore and used as received.

Protocol A: A mixture used to make specimen described herein comprised a catalyst, a PAG, ITX, and DCPC. Test specimens were made from the photopolymer using a 3D printer. The specimens were formed in the shape of a type V tensile dog bone and bend bar. Layers (e.g., stored as a list of images in PNG file format) were sent to a 385 nm DLP printer. The specimen was printed one slice at a time; the slices were stacked over one another (z-slice stacking). Each slice of the specimen was exposed to 600 mJ/cm$^2$ of ultraviolet (UV) light after the slice was printed. The specimen was then rinsed with isopropyl alcohol and dried with compressed air before further processing. Differential scanning calorimetry and tensile testing were employed to evaluate the thermomechanical properties of the specimen.

Figure 5A:
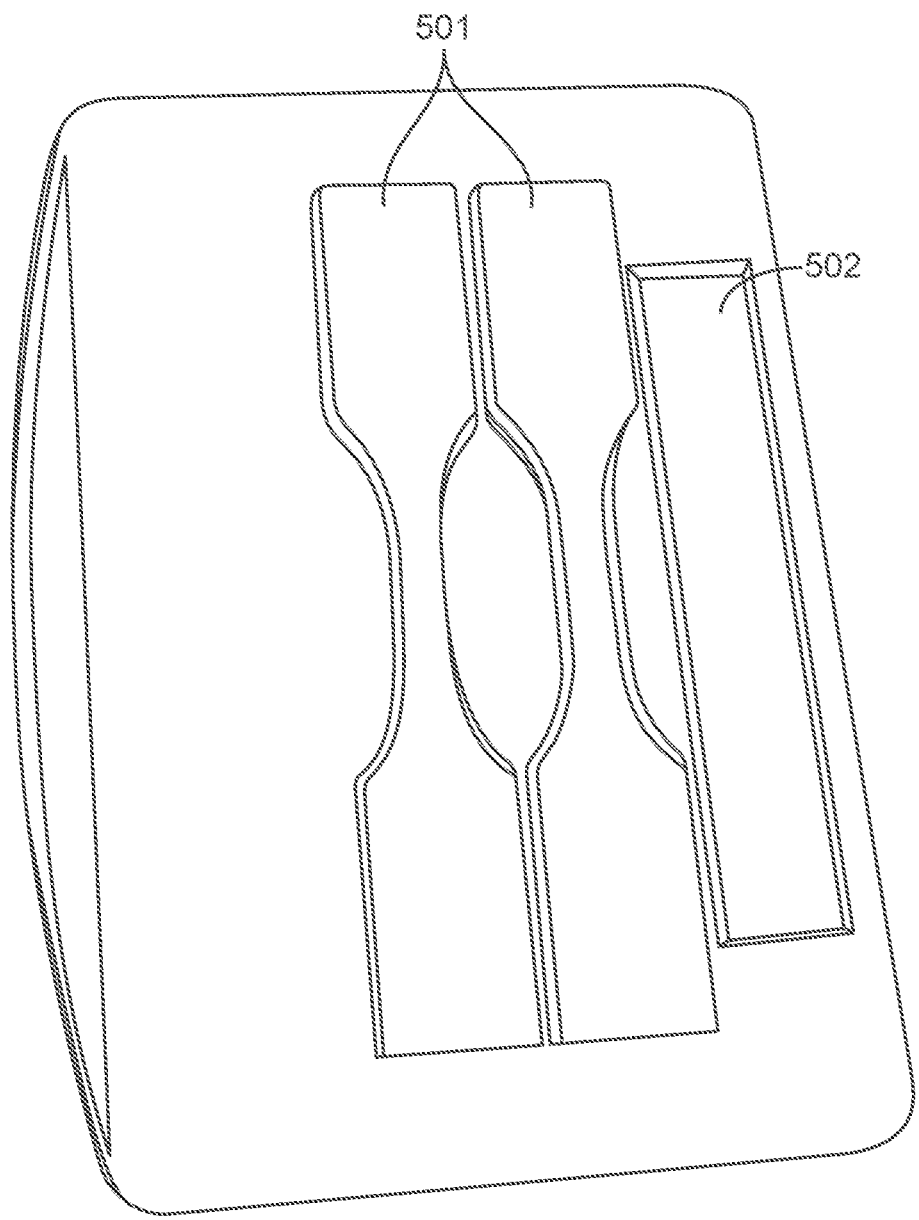
FIG. 5A shows an example of a specimen made using a photopolymer.
Figure 5B:
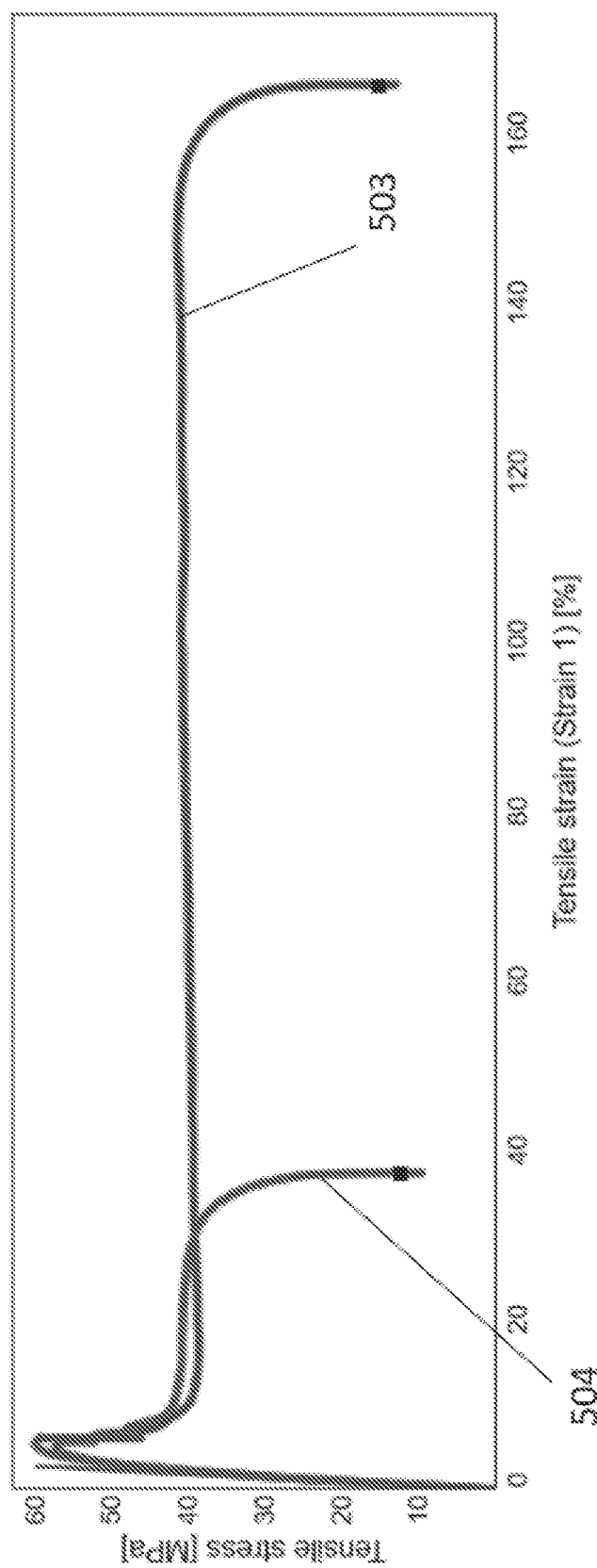
FIG. 5B shows an example of a tensile-strain diagram of specimen made using a photopolymer.
Figure 5C:
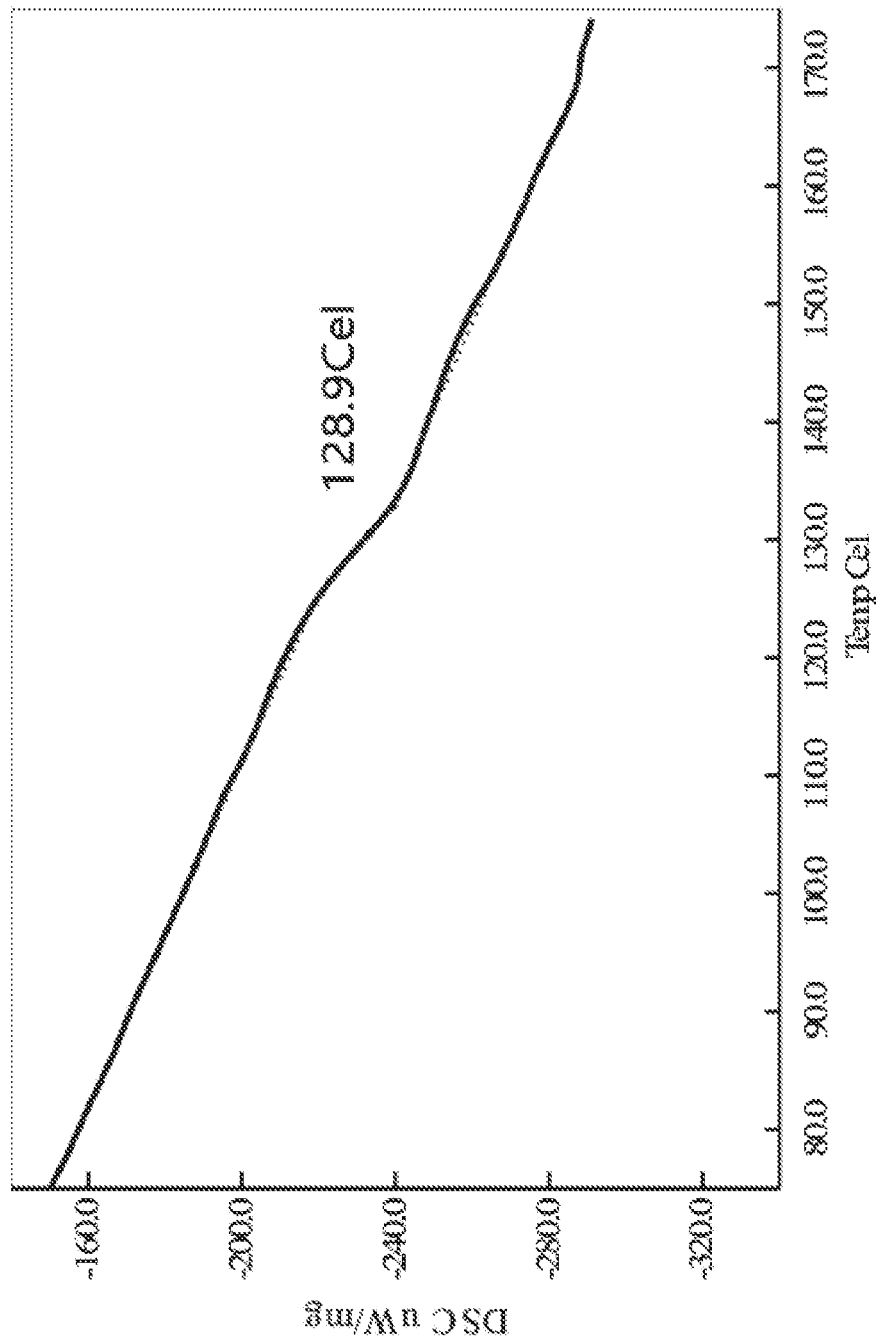
FIG. 5C shows an example of differential scanning calorimetry results of specimen made using a photopolymer.
Figure 6A:
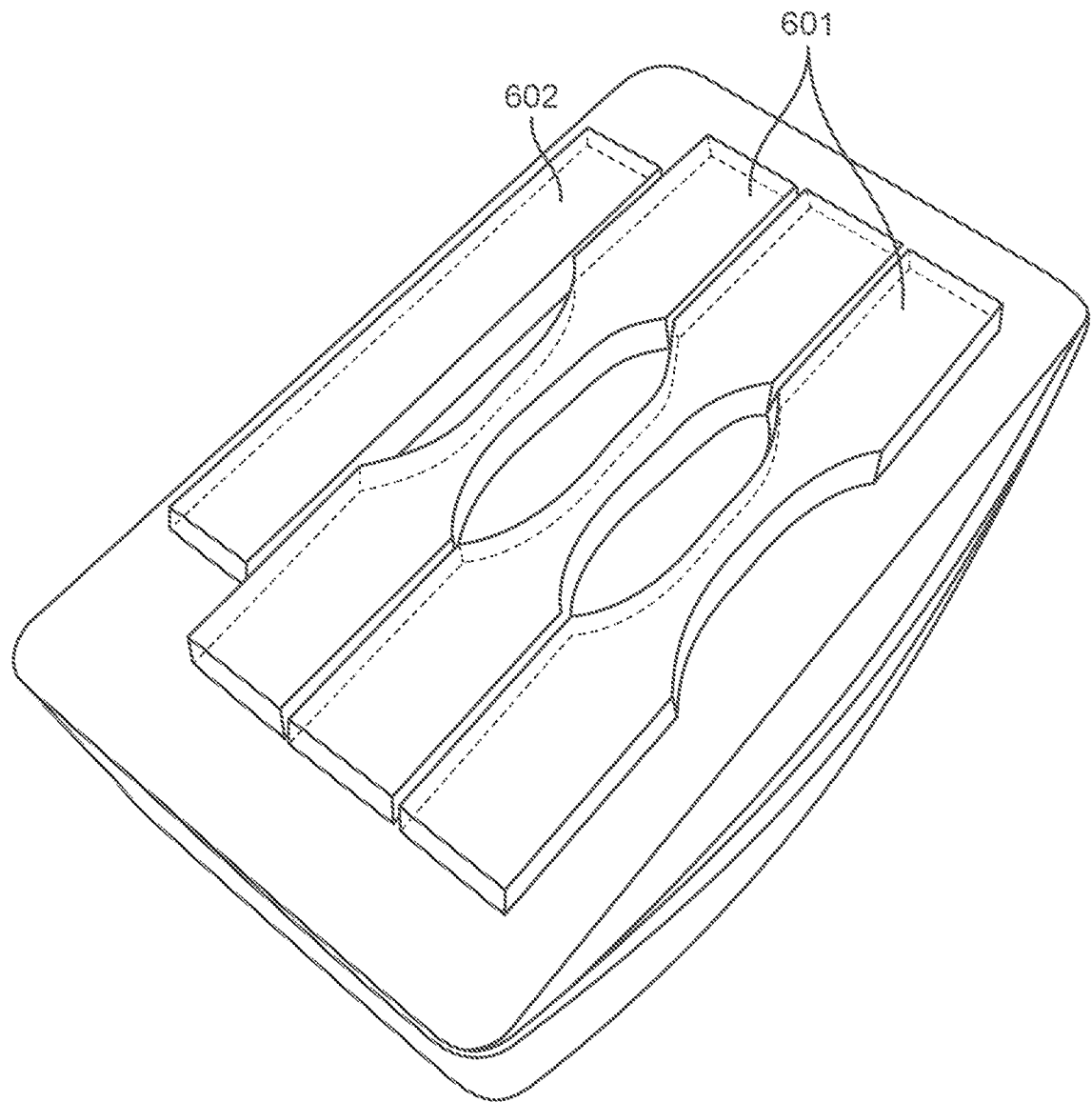
FIG. 6A shows an example of specimen made using a photopolymer.
Figure 6B:
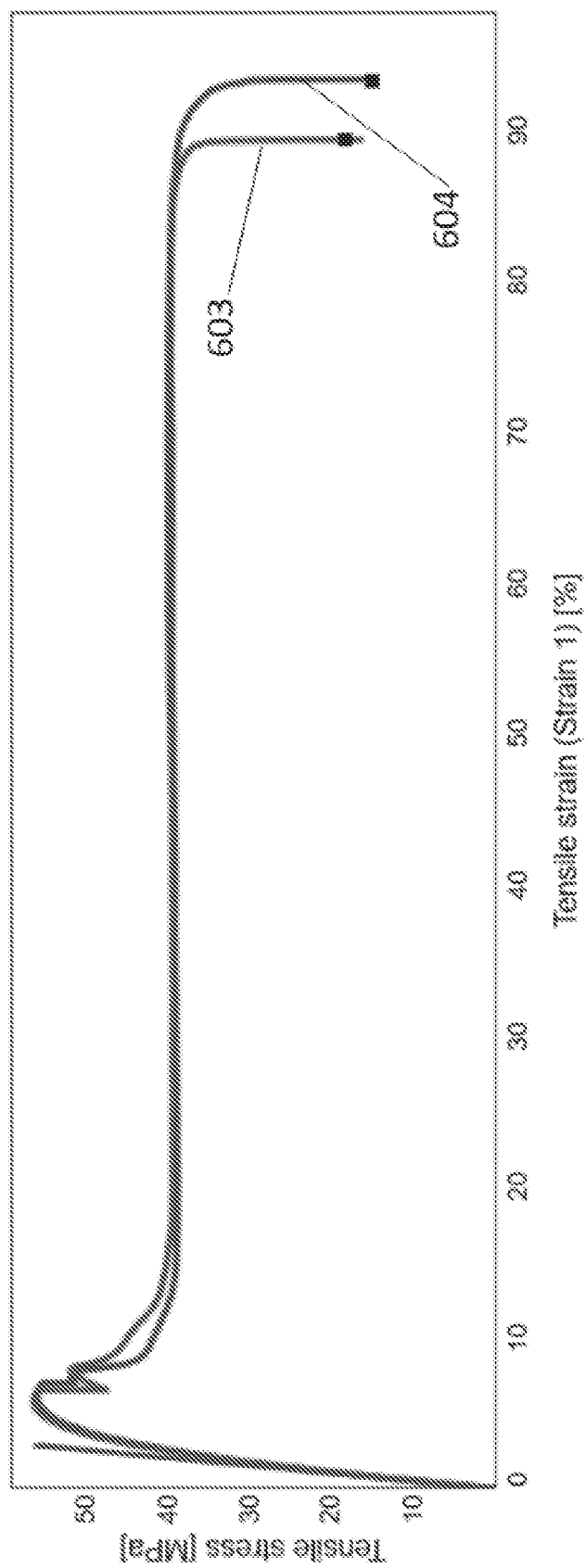
FIG. 6B shows an example of a tensile-strain diagram of specimen made using a photopolymer.
Figure 6C:
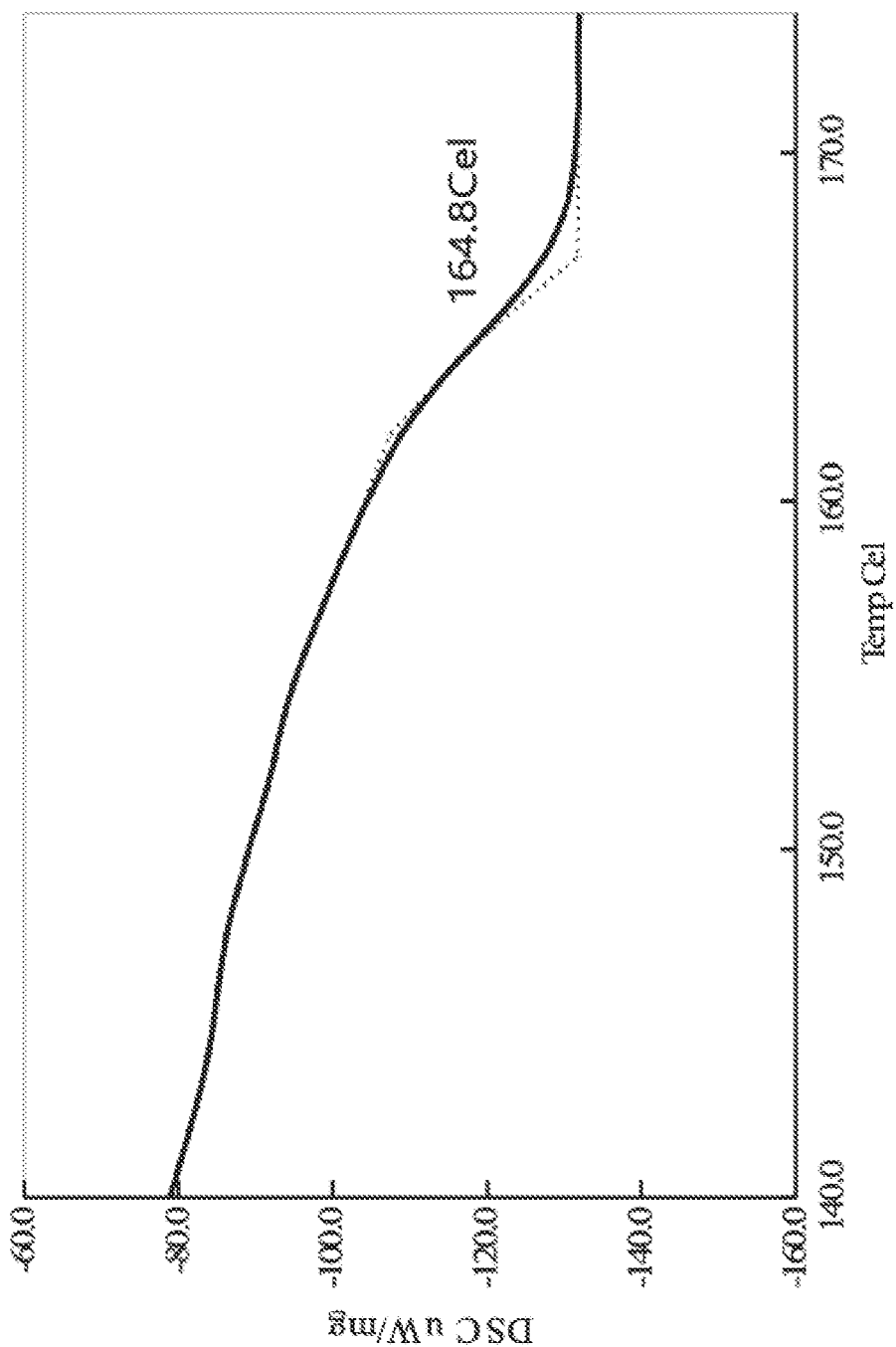
FIG. 6C shows an example of differential scanning calorimetry results of specimen made using a photopolymer.

Example A: 81 milligram (mg) of Catalyst A was mixed with 157.5 mg of PAG-A, 157.5 mg of ITX, and 90 g of DCPD solution. Specimens were made as described according to protocol A. For post-processing, the specimens were subjected to 160° C. for 2 hours on a hotplate with about 0.2% oxygen content. FIG. 5A shows an image of two ASTM TypeV tensile "dogbone" specimens 501 and a bend bar specimen 502 printed according to protocol A. Table 1 shows the specimens had a mean thickness of about 3.2 millimeter (mm) and a mean width of about 3.14 mm, both having a standard deviation (e.g., accuracy) of 0.0. The dimensions exhibit a deviation <0.05 mm compared to targeted dimension, reflecting the accuracy of the resin and printing process. FIG. 5B shows an example of a tensile-strain diagram generated for each specimen 501 when testing on a tensile tester following protocols from ASTM- D638. Table 2 shows the results (including standard deviation (e.g., accuracy)) of the tensile-strain test detailed in FIG. 5B. The specimens had a mean: Young's Modulus of about 2181 megapascals (MPa), maximum tensile stress of about 58.6 MPa, tensile strain at yield of about 5.2%, and tensile strain at break of about 101.5%. The variability in the curves (in FIG. 5B) between the specimens, and the large standard deviation in tensile strain at break from Table 2 can be attributed to random internal defects, such as, for example, bubbles that can form during the 3D printing process. FIG. 5C shows an example of differential scanning calorimetry results for the 3D objects. The photopolymer was shown to have a glass transition temperature (Tg) of about 129° C. Samples 3D printed and tested in this example exhibit a unique combination of high stiffness (Modulus >1800 MPa), high ductility (Tensile strain at Break >20%), and high Tg (>120° C.).

targeted dimension, reflecting the accuracy of the resin and printing process. FIG. 6B shows an example of a tensile-strain diagram generated for each specimen 601 when testing on a tensile tester following protocols from ASTM-D638. Table 4 shows the results (including standard deviation (e.g., accuracy)) of the tensile-strain test detailed in FIG. 6B. The specimens had a mean: Young's Modulus of about 1958 megapascals (MPa), maximum tensile stress of about 56 MPa, tensile strain at yield of about 5.9%, and tensile strain at break of about 91.2%. FIG. 6C shows an example of differential scanning calorimetry results for the 3D objects. The photopolymer was shown to have a glass transition temperature (Tg) of about 165° C. Samples 3D printed and tested in this example exhibit a unique combination of high stiffness (Modulus >1800 MPa), high ductility (Tensile strain at Break >20%), and high Tg (>120° C.).

TABLE 1

|  | Thickness [mm] | Width [mm] |
| --- | --- | --- |
| 1 | 3.21 | 3.15 |
| 2 | 3.20 | 3.14 |
| Mean | 3.20 | 3.14 |
| Standard deviation | 0.0 | 0.0 |

TABLE 3

|  | Thickness [mm] | Width [mm] |
| --- | --- | --- |
| 1 | 3.38 | 3.86 |
| 2 | 3.36 | 3.86 |
| Mean | 3.37 | 3.86 |
| Standard deviation | 0.0 | 0.0 |

TABLE 2

|  | Modulus (Young's Tensile stress 0%-3%) [MPa] | Maximum Tensile stress [MPa] | Tensile strain (Strain 1) at Yield (Zero slope) [%] | Tensile strain (Strain 1) at Break (Automatic force drop) [%] |
| --- | --- | --- | --- | --- |
| 1 | 2180.54 | 57.27 | 5.00 | 165.70 |
| 2 | 2181.67 | 59.97 | 5.33 | 37.32 |
| Mean | 2181.11 | 58.62 | 5.17 | 101.51 |
| Standard deviation | 0.8 | 1.9 | 0.2 | 90.8 |

Example B: 81 milligram (mg) of Catalyst B was mixed with 157.5 mg of PAG-A, 157.5 mg of ITX, and 90 g of DCPD solution. Evidence of photocuring was observed, but the degree of curing was not sufficient to yield a self-supporting specimen.

Example C: 27 milligram (mg) of Catalyst C was mixed with a mixture comprising: 157.5 mg of PAG-A, 157.5 mg

TABLE 4

Figure 7A:
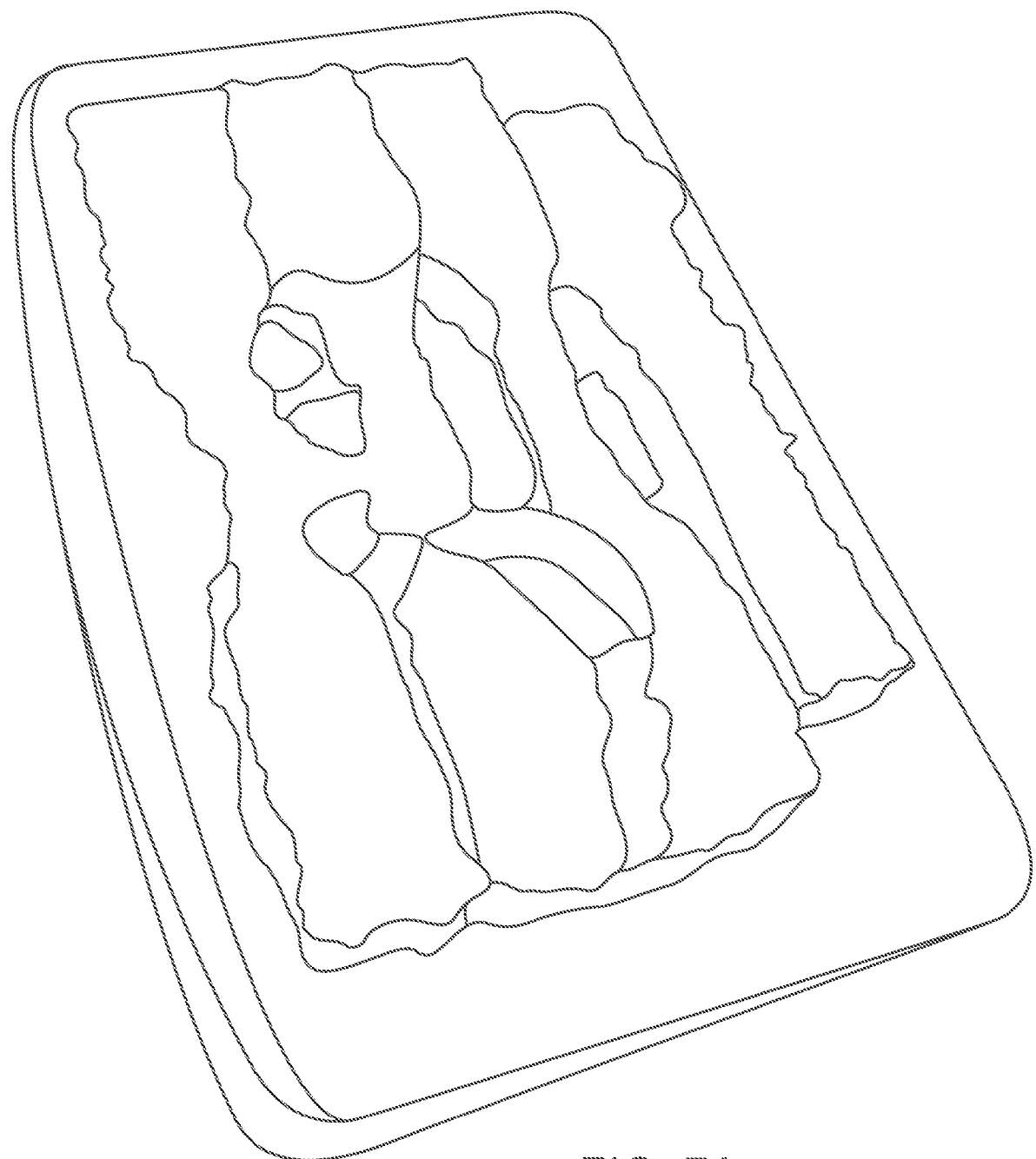
FIG. 7A shows an example of a specimen made using a photopolymer.
Figure 7B:
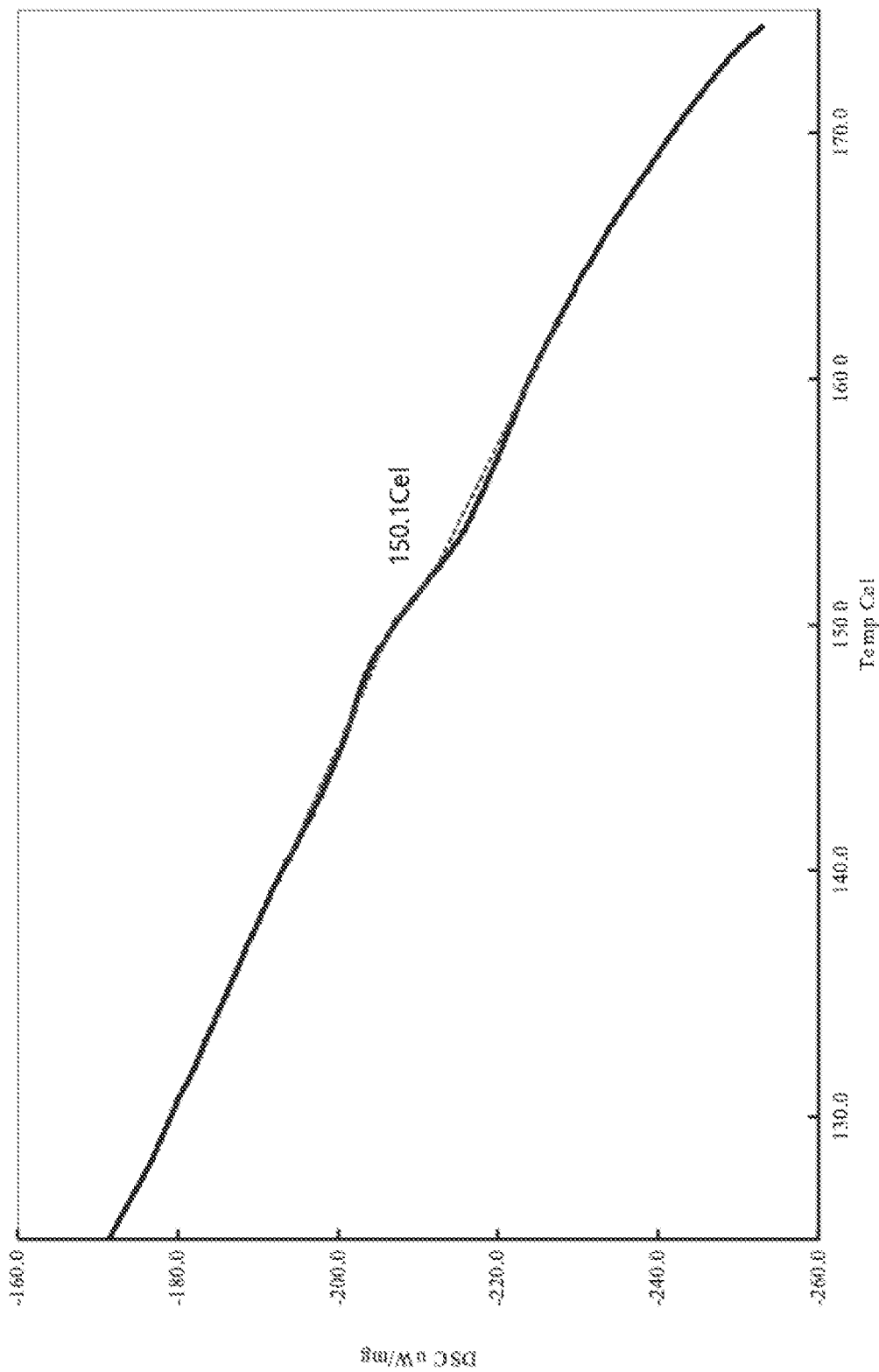
FIG. 7B shows an example of differential scanning calorimetry results of specimen made using a photopolymer.

|  | Modulus (Young's Tensile stress 0%-3%) [MPa] | Maximum Tensile stress [MPa] | Tensile strain (Strain 1) at Yield (Zero slope) [%] | Tensile strain (Strain 1) at Break (Automatic force drop) [%] |
| --- | --- | --- | --- | --- |
| 1 | 1930.55 | 55.69 | 6.10 | 93.25 |
| 2 | 1986.59 | 56.16 | 5.77 | 89.26 |
| Mean | 1958.57 | 55.92 | 5.94 | 91.25 |
| Standard deviation | 39.6 | 0.3 | 0.2 | 2.8 | of ITX, and 90 g of DCPD solution. Specimens were made as described according to protocol A. For post-processing, the specimens were subjected to 160° C. for 2 hours in an oven under nitrogen. FIG. 6A shows examples of two ASTM TypeV tensile "dogbone" specimens 501 and a bend bar specimen 502 printed according to protocol A. Table 3 shows the specimens had a mean thickness of about 3.37 millimeter (mm) and a mean width of about 3.86 mm, both having a standard deviation (e.g., accuracy) of 0.0. The dimensions exhibit a deviation <0.05 mm compared to Example D: 27 milligram (mg) of Catalyst D was mixed with 30 g of a mixture comprising: 157.5 mg of PAG-A, 157.5 mg of ITX, and 90 g of DCPD solution. FIG. 7 shows examples of specimens, made using protocol A, that had melted due to exothermic activity of the material. A post-process was not performed on the specimens. FIG. 7B shows an example of differential scanning calorimetry results for the 3D object. The photopolymer was shown to have a glass transition temperature (Tg) of about 150° C.

Example E: 81 milligram (mg) of Catalyst C, 157.5 mg of PAG-B, 157.5 mg of ITX, and 90 g of DCPD solution. The processed (protocol A) mixture showed evidence of photo-curing, but the degree of curing was not sufficient to yield a self-supporting specimen.

Example 3: Orthodontic Aligner

Protocol B: A mixture used to make specimen described herein comprised a catalyst, a PAG, 2-Isopropylthioxan-thone (ITX), and dicyclopentadiene containing approximately 6% trimer (DCPC). The components were mixed together to form a suspension and degassed with nitrogen before adding to printer. .STL file of an orthodontic aligner (FIG. 8) was sliced into 200 micron thick layers, to form a list of .PNG images, which was sent to a 385 nm DLP printer, with each image corresponding to one slice. The resin formulations above were added to the resin tray of the DLP printer. Parts were printed at room temperature under an inert environment containing 0.0-0.5% oxygen. 700 mJ/cm$^2$ exposure for 200 micron z-slices. The green part (e.g., FIG. 9A-top view and FIG. 9B—side view) was rinsed with isopropyl alcohol, then dried with compressed air before post-processing. Post-processing comprised heating the green part at 120° C. for 2 h on a hotplate inside purge box at 0.0-0.2% oxygen, which can then be trimmed and cleaned to produce an orthodontic aligner (e.g., FIG. 10).

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for generating a dental product or an orthodontic product, comprising:
   (a) providing a mixture comprising (i) a latent ruthenium (Ru) complex; (ii) an initiator; (iii) a sensitizer that sensitizes said initiator; and (iv) at least one polymer precursor; and
   (b) exposing said mixture to electromagnetic radiation to activate said initiator, wherein upon activation, said initiator reacts with said latent Ru complex to generate an activated Ru complex, which activated Ru complex reacts with said at least one polymer precursor to generate at least a portion of a final product of said dental product or said orthodontic product, wherein said at least said portion of said final product of said dental product or said orthodontic product comprises a polymer generated from said at least one polymer precursor.

2. The method of claim 1, wherein said dental product or said orthodontic product is generated using additive manufacturing.

3. The method of claim 1, wherein said sensitizer is configured to transfer or disperse the energy of electromagnetic radiation.

4. The method of claim 1, wherein said mixture is activated at a wavelength from 200-800 nanometers (nm) at a temperature from 0° C. to 100° C. for 1 nanosecond (ns) to 1 week.

5. The method of claim 1, further comprising cleaning said dental product or said orthodontic product.

6. The method of claim 5, wherein said dental product or said orthodontic product is cleaned using a solvent, agitation, sonication, stirring, air drying, air knives, automated washing, or any combination thereof.

7. The method of claim 5, wherein a surface of said dental product or said orthodontic product is smoothed, brightened, coated, sealed, sterilized, or a combination thereof.

8. The method of claim 1, further comprising post-curing said dental product or said orthodontic product.

9. The method of claim 8, wherein said dental product or said orthodontic product is post-cured using ultraviolet radiation, visible light radiation, convection heating, conduction heating, or any combination thereof.

10. A method for generating a dental product or an orthodontic product, comprising:
    (a) providing mixture comprising (i) a latent ruthenium (Ru) complex; (ii) an initiator; and (iii) at least one polymer precursor, wherein said latent Ru complex and said initiator are present at a ratio of said Ru complex to said initiator at a ratio by moles from 0.01:1.0 to 10:1.0; and
    (b) exposing said mixture to electromagnetic radiation to activate said initiator, wherein upon activation, said initiator reacts with said latent Ru complex to generate an activated Ru complex, which activated Ru complex reacts with said at least one polymer precursor to generate at least a portion of a final product of said dental product or said orthodontic product, wherein said at least said portion of said final product of said dental product or said orthodontic product comprises a polymer generated from said at least one polymer precursor.

11. A method for printing a dental product or an orthodontic product, comprising:
    (a) providing a resin comprising (i) a latent ruthenium (Ru) complex, (ii) an initiator, and (iii) at least one polymer precursor; and
    (b) exposing said resin to electromagnetic radiation to activate said initiator, wherein upon activation, said initiator reacts with said latent Ru complex to generate an activated Ru complex, which activated Ru complex reacts with said polymer precursor to print at least portion of a final product of said dental product or said orthodontic product, wherein said at least said portion of said final product of said dental product or said orthodontic product comprises a polymer generated from said at least one polymer precursor.

12. The method of claim 11, further comprising printing said dental product or said orthodontic product adjacent to a support.

13. The method of claim 12, wherein said dental product or said orthodontic product is removed from said support using robot-assistance, sonication, vibration, chemical swelling, chemical etching, laser ablation, laser cutting, blade cutting, or any combination thereof.

* * * * *